US006991602B2

(12) United States Patent
Nakazawa et al.

(10) Patent No.: US 6,991,602 B2
(45) Date of Patent: Jan. 31, 2006

(54) MEDICAL TREATMENT METHOD AND APPARATUS

(75) Inventors: Masaaki Nakazawa, Hachioji (JP); Toshio Nakamura, Hachioji (JP); Hidenobu Kimura, Hachioji (JP); Tatsuya Furukawa, Hachioji (JP); Koji Yamaya, Hachioji (JP); Nobuyuki Matsuura, Hino (JP); Hisao Yabe, Hachioji (JP)

(73) Assignee: Olympus Corporation, Tokyo (JP)

( * ) Notice: Subject to any disclaimer, the term of this patent is extended or adjusted under 35 U.S.C. 154(b) by 166 days.

(21) Appl. No.: 10/334,462

(22) Filed: Dec. 31, 2002

(65) Prior Publication Data

US 2003/0135091 A1     Jul. 17, 2003

(30) Foreign Application Priority Data

Jan. 11, 2002   (JP)   .............................. 2002-005106

(51) Int. Cl.
  *A61B 1/00* (2006.01)
(52) U.S. Cl. ...................... 600/101; 600/113; 600/114; 606/167
(58) Field of Classification Search ................ 600/101, 600/104, 113, 114, 117, 118, 153
   See application file for complete search history.

(56) References Cited

U.S. PATENT DOCUMENTS

| 5,178,130 A | * | 1/1993 | Kaiya ......................... 600/109 |
| 5,545,179 A | | 8/1996 | Williamson, IV |
| 5,797,835 A | * | 8/1998 | Green ........................ 600/106 |
| 6,066,090 A | * | 5/2000 | Yoon ........................... 600/113 |

* cited by examiner

*Primary Examiner*—Beverly M. Flanagan
(74) *Attorney, Agent, or Firm*—Straub & Pokotylo; John C. Pokotylo

(57) ABSTRACT

A medical treatment method comprises orally inserting a first endoscope having a first treatment tool provided thereto into a body cavity, inserting a first insertion member insertion support tool from at least one of abdominal and transdermal cavities into the body cavity, inserting a second endoscope having a second treatment tool provided thereto into the body cavity through the first insertion member insertion support tool, grasping a lesioned part by the second treatment tool inserted into the body cavity by the second endoscope, cutting the lesioned part by the first treatment tool inserted into the body cavity by the first endoscope, and collecting the lesioned part.

33 Claims, 33 Drawing Sheets

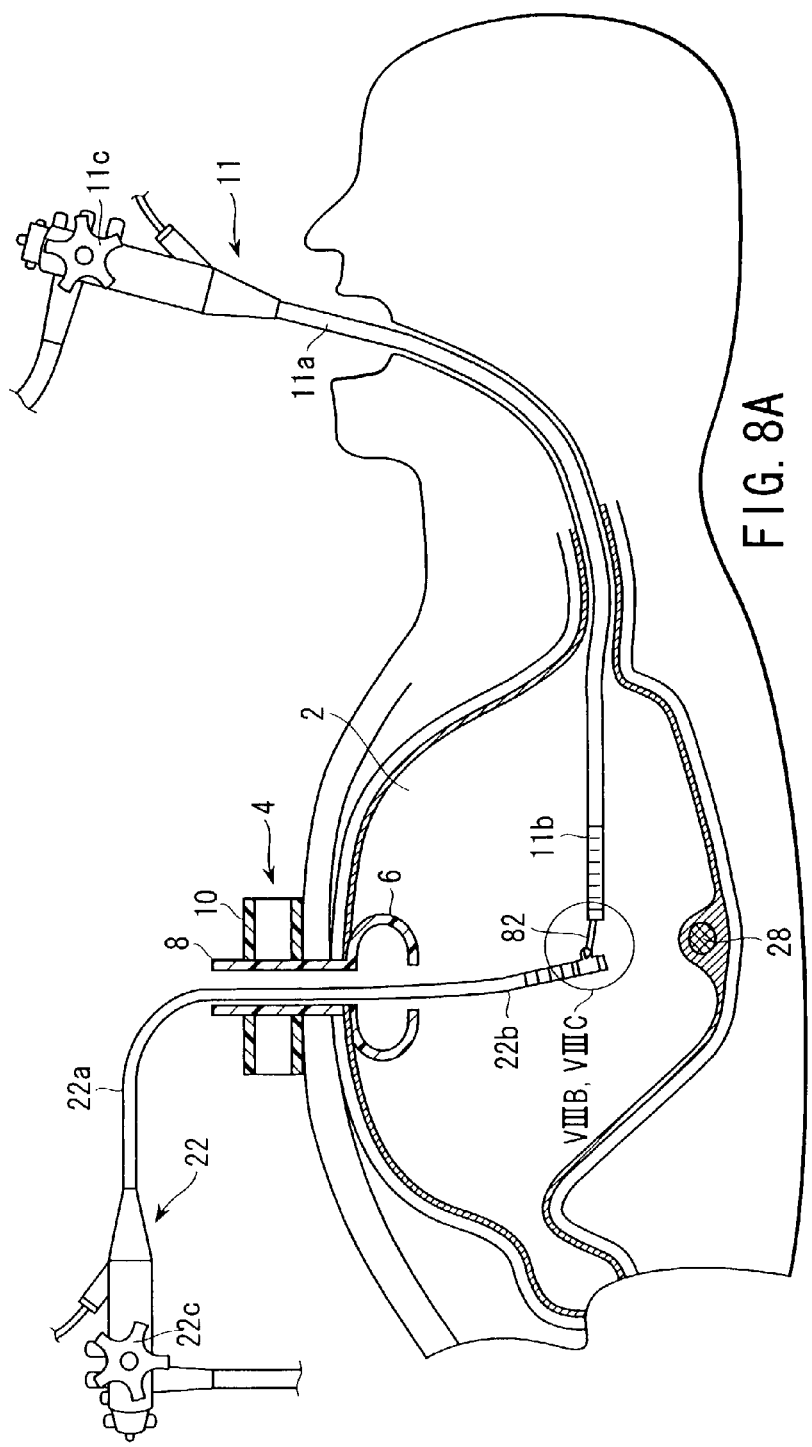
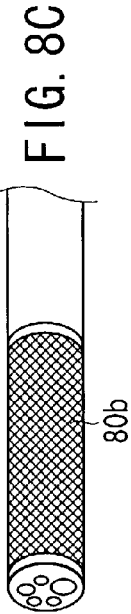
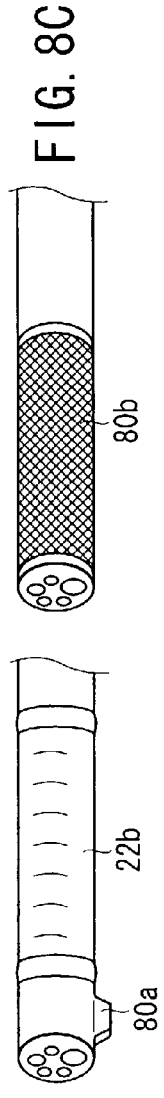
FIG. 8A
FIG. 8C
FIG. 8B

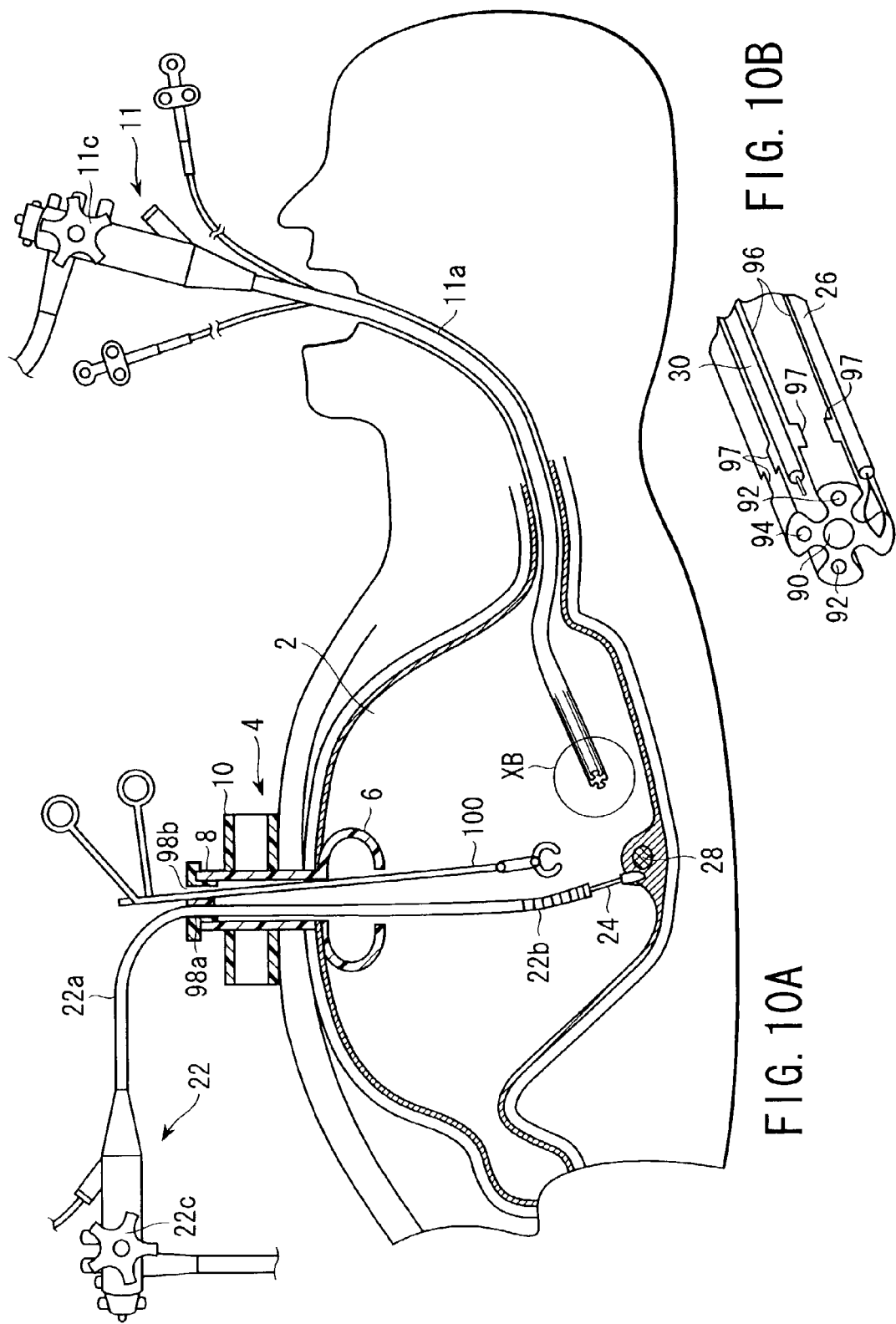

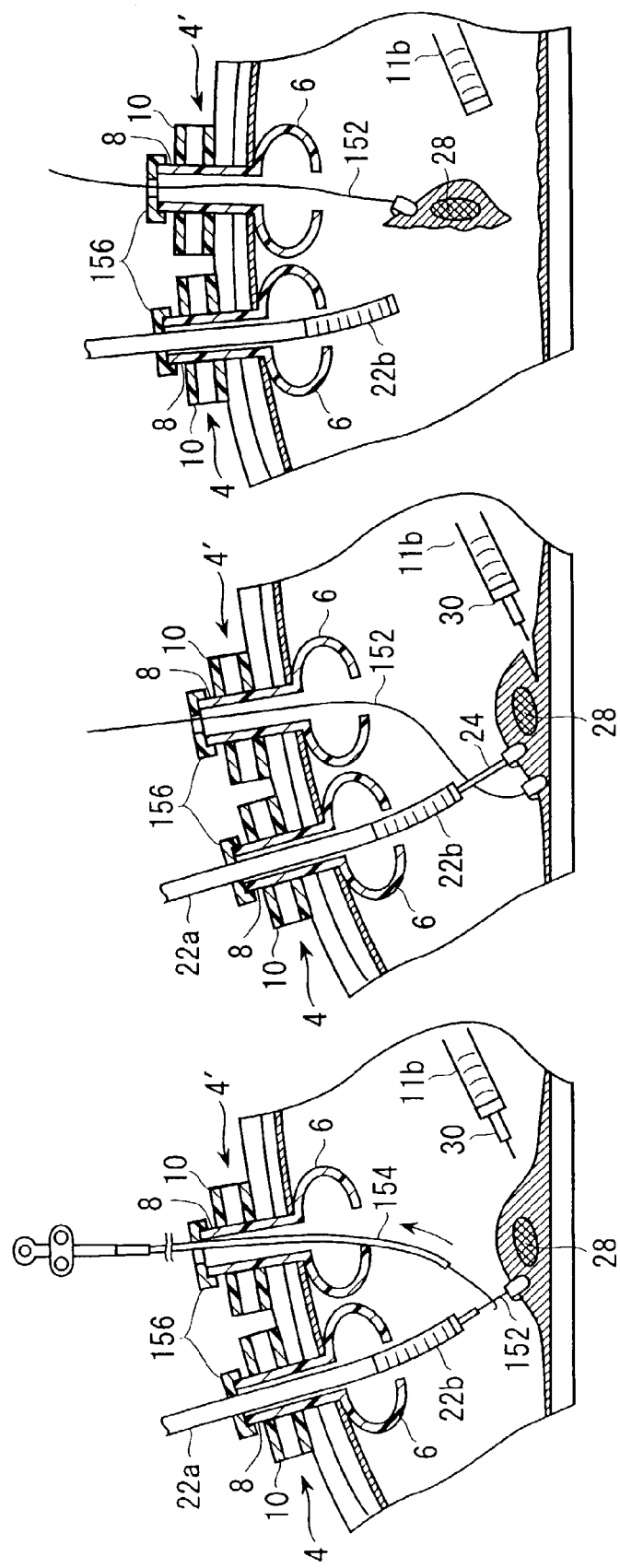

MEDICAL TREATMENT METHOD AND APPARATUS

CROSS-REFERENCE TO RELATED APPLICATIONS

This application is based upon and claims the benefit of priority from the prior Japanese Patent Application No. 2002-005106, filed Jan. 11, 2002, the entire contents of which are incorporated herein by reference.

BACKGROUND OF THE INVENTION

1. Field of the Invention

The present invention relates to a medical treatment method for treating a lesioned part in an organ, and an apparatus using this method.

2. Description of the Related Art

For example, as disclosed in U.S. Pat. No. 5,545,179, in regard to an insertion support tool used to insert an endoscope into a body cavity, an insertion portion of the endoscope is inserted from an insertion opening of this insertion support tool. In this case, the inside of the insertion opening, namely, a balloon portion in the body cavity is inflated and the insertion portion of the endoscope is inserted into the body while being appressed against the balloon portion. The horizontal cross-section of the balloon portion assumes a ring shape, and the seal state in an organ is maintained while maintaining air-tightness of the insertion portion of the endoscope during an operation. Further, this balloon portion is molded by using silicon elastomer and polyurethane, or silicon elastomer and polyethylene, and formed so as to reduce the friction with the insertion portion of the endoscope.

However, a firm pressure must be constantly applied to the balloon portion in order to maintain the air-tightness in the organ during the operation. Inflation of the balloon portion also causes a larger pressure to be applied to the insertion portion of the endoscope. Therefore, although the balloon portion is formed of such a material that has low friction with the insertion portion of the endoscope, a large frictional force is generated between the insertion portion of the endoscope and the balloon portion. Thus, it is sometimes hard to smoothly insert or retract the insertion portion.

Furthermore, there is no established medical treatment for treating a lesioned part of an organ using such an insertion support tool.

BRIEF SUMMARY OF THE INVENTION

The present invention provides a medical treatment method for treating a lesioned part of an organ, and an apparatus using this method.

According to one aspect of the present invention, there is provided a medical treatment method comprising: orally inserting a first endoscope having a first treatment tool provided thereto into a body cavity; inserting a first insertion member insertion support tool from at least one of abdominal and transdermal cavities into the body cavity; inserting a second endoscope having a second treatment tool provided thereto into the body cavity through the first insertion member insertion support tool; grasping a lesioned part by the second treatment inserted into the body cavity by the second endoscope; cutting the lesioned part by the first treatment tool inserted into the body cavity by the first endoscope; and collecting the lesioned part.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8A is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a fifth embodiment;

FIG. 8B is a schematic view showing that a holding portion which can be held by using the grasping forceps protruding from the insertion portion of the first flexile endoscope is provided at the end portion of the second endoscope;

FIG. 8C is a schematic view showing that a blade is arranged at the curved portion of the second endoscope;

FIG. 10A is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a seventh embodiment;

FIG. 10B is a schematic view showing an end portion of the insertion portion of the first flexible endoscope;

FIG. 28A is a schematic view showing a state that a clip with a thread provided in the second endoscope is hooked by a collection treatment tool for collecting the clip with a thread which is led from another gastric fistula formation tube according to a 21st treatment;

FIG. 28B is a schematic view showing a state that the clip with a thread is taken out of a body from the gastric fistula formation tube having the collection treatment tool arranged thereto, the grasping forceps is taken out from the second flexible endoscope and a lesioned part is grasped;

FIG. 28C is a schematic view showing a state that a lesioned part is cut by using the first flexible endoscope, the clip with a thread is pulled and a cut piece is taken out of the body;

DETAILED DESCRIPTION OF THE INVENTION

Preferred embodiments according to the present invention will now be described hereinafter with reference to the accompanying drawings.

A first embodiment will be first explained in connection with FIGS. 1 to 3.

Figure 1:
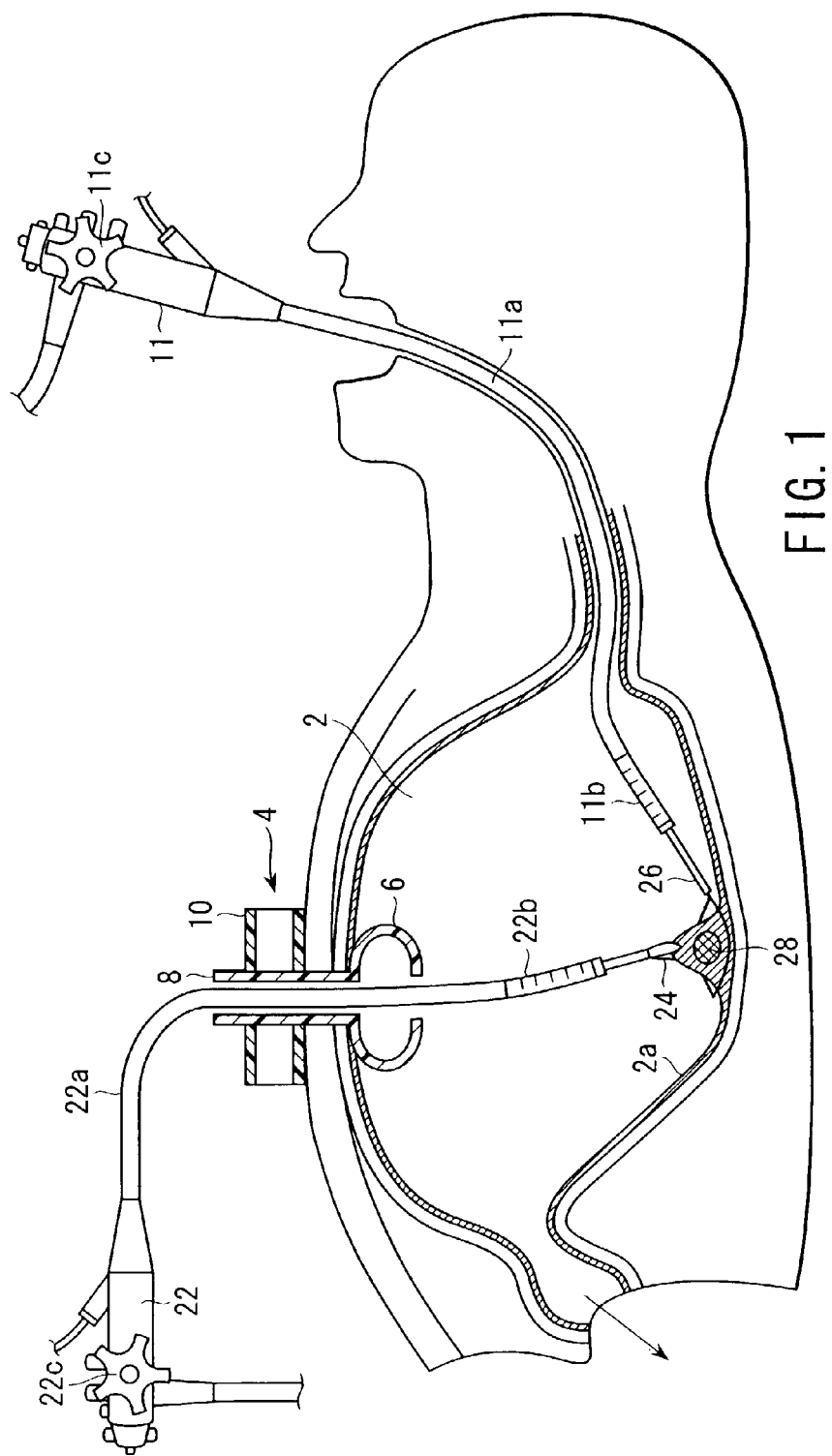
FIG. 1 is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a first embodiment.

As shown in FIG. 1, a treatment apparatus according to this embodiment includes two flexible endoscopes 11 and 22 each having flexible insertion portions 11a and 22a which can be inserted into a body cavity as insertion members. Curved portions 11b and 22b which can be bent are provided at respective ends of the insertion portions 11a and 22a of the flexible endoscopes 11 and 22. The curved portions 11b and 22b are operated by operation portions 11c and 22c respectively provided in main bodies of the endoscopes 11 and 22. Although not shown, at least one of a forceps channel, an air supply/water supply/suction channel and an observation optical system is provided to each of the insertion portions 11a and 22a of the endoscopes 11 and 22. In this embodiment, at least one forceps channel and an observation optical system are provided to each of the insertion portions 11a and 22a of the respective endoscopes 11 and 22.

The insertion portions 11a and 22a of the flexible endoscopes 11 and 22 are inserted into an organ such as a stomach 2. In this case, one endoscope, i.e., a first flexible endoscope 11 is orally inserted into the stomach 2. The other endoscope, i.e., a second flexible endoscope 22 is inserted into the stomach 2 through an inner hole of a gastric fistula formation tube (a tube that communicates the inside and outside of a body) 4 which is an insertion member insertion support tool that communicates the inside of the stomach 2 to the outside of the body. The gastric fistula formation tube 4 has a dome portion 6 which is arranged inside the stomach 2 and has a hollow and substantially dome shape and a tube 8 which is mainly arranged outside the body, whose one end communicates with the vicinity of the top of the dome portion 6 and which is, e.g., integrally formed with the dome portion 6. A stopper 10 is caused to nip at this gastric fistula formation tube 4 from the other end side of the tube 8 on the surface of the skin of a patient and engaged so as not to fall into the stomach 2. It is preferable that the dome portion 6 and the curved tube 8 are formed of, e.g., medical chloroethene, PTFE or a silicon rubber material.

The gastric fistula formation tube 4 is placed and kept as follows, and the inside and the outside of the stomach 2 communicate with each other.

Figure 2A:
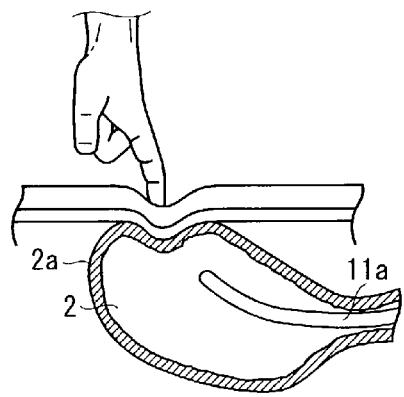
FIG. 2A is a schematic view showing a procedure to keep a gastric fistula formation tube on a body wall.
Figure 3:
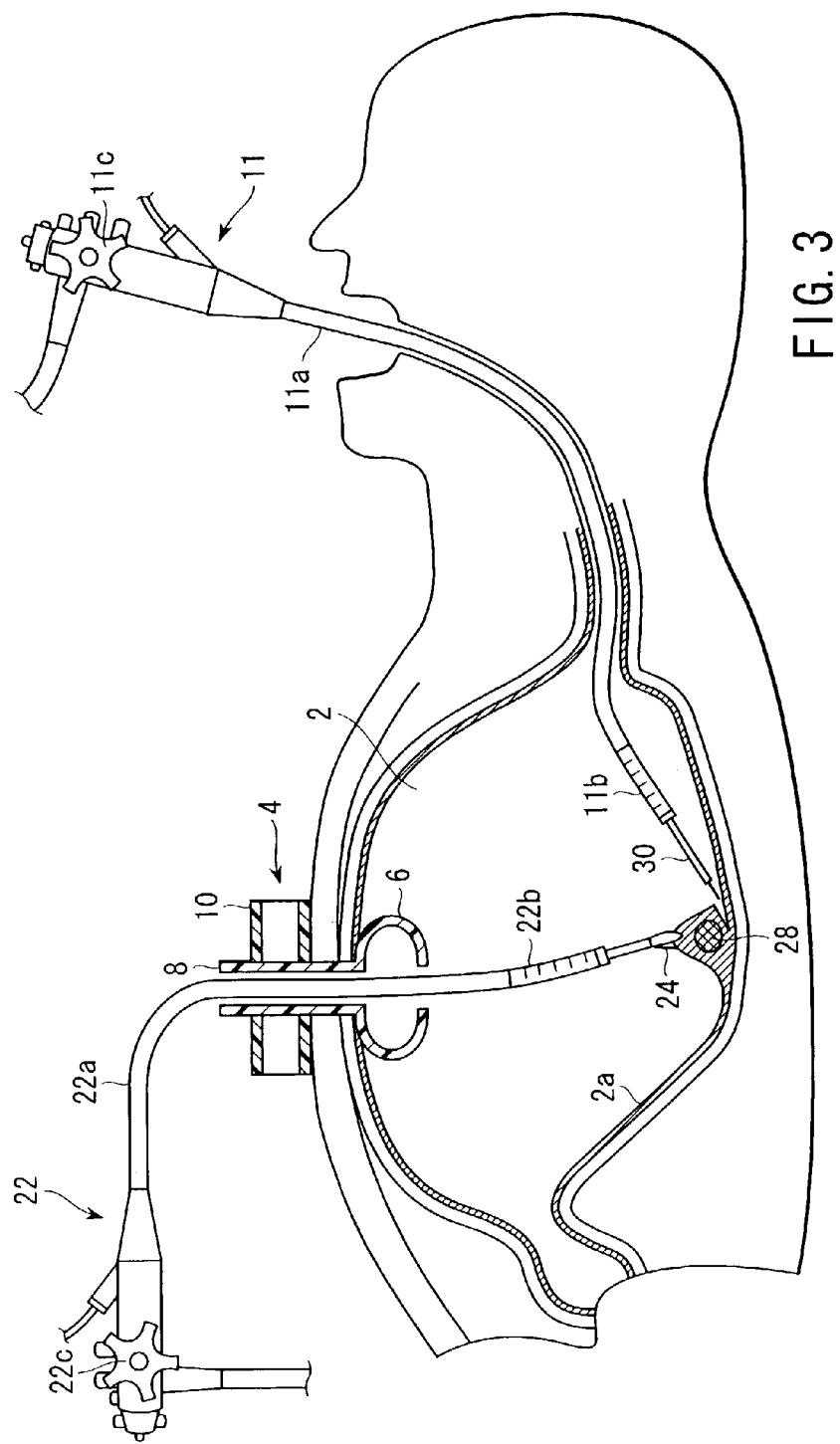
FIG. 3 is a schematic cross-sectional view showing a modification of a treatment apparatus according to the first embodiment.

At first, as shown in FIG. 2A, the insertion portion 11a of the first flexible endoscope 11 is orally inserted into the stomach 2 in advance. In order to select a part where the gastric fistula formation tube 4 is to be positioned, the abdominal wall is pushed with a finger and it is confirmed that a stomach wall 2a protuberates toward the inner cavity side like a submucous tumor. Transmitted light from the end of the insertion portion 11a of the first endoscope 11 is confirmed through the abdominal wall, and setting of a quantity of light of the first endoscope 11 is performed if the transmitted light is weak. A centesis position (insertion support tool formation position) is selected, and this position is marked by using a magic marker and the like.

Figure 2B:
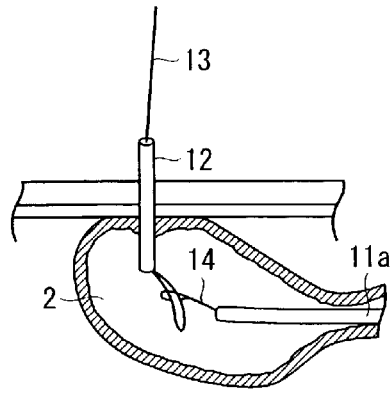
FIG. 2B is a schematic view showing a procedure following that illustrated in FIG. 2B to keep the gastric fistula formation tube on the body wall.

Then, a paracentesis needle with an outer casing (not shown) is pushed to the inside of the stomach 2 from the outside of the body cavity at the selected part, and the paracentesis needle as an inner casing is removed. Subsequently, as shown in FIG. 2B, a loop wire 13 is inserted into the outer casing 12 and held by a polypectomy snare 14 inserted into one of the forceps channels of the first endoscope 11 orally inserted into the stomach 2 in advance.

Figure 2C:
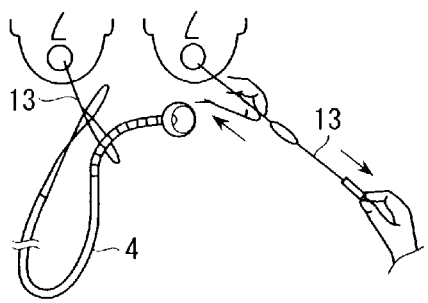
FIG. 2C is a schematic view showing a procedure following that illustrated in FIG. 2B to keep the gastric fistula formation tube on the body wall.

Then, as shown in FIG. 2C, with the loop wire 13 being grasped by the snare 14, the first endoscope 11 is pulled out to the outside the oral cavity. At this moment, the above-described loop wire 13 is further extended to the outside of the body cavity from the outer casing 12.

Figure 2D:
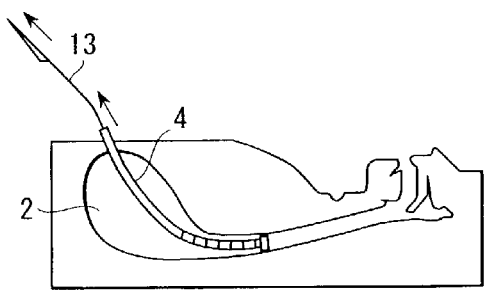
FIG. 2D is a schematic view showing a procedure following that depicted in FIG. 2C to keep the gastric fistula formation tube on the body wall.

Thereafter, the gastric fistula formation tube 4 and the loop wire 13 pulled out of the oral cavity are tied together. That is, the loop wire 13 is removed from the snare 14 of the first endoscope 11, and the loop wire 13 orally extended to the outside of the body cavity and the tube 8 of the gastric fistula formation tube 4 are tied together. As shown in FIG. 2D, the loop wire 13 extended from the body surface part side, i.e., from the outer casing to the body cavity side is pulled. Then, the gastric fistula formation tube 4 is orally led into the stomach 2, and the dome portion 6 is caused to be appressed against the abdominal wall so that the tube 8 is pulled out to the outside of the body cavity.

Figure 2E:
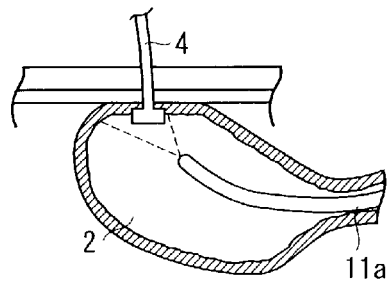
FIG. 2E is a schematic view showing a procedure following that depicted in FIG. 2D to keep the gastric fistula formation tube on the body wall.

Thereafter, as shown in FIG. 2E, the first endoscope 11 is again orally inserted, and the endoscope 11 is used to observe and confirm that the dome portion 6 of the gastric fistula formation tube 4 does not bite into the stomach wall. That is, it is confirmed that the gastric fistula formation tube 4 is appropriately provided.

Then, the tube 8 of the gastric fistula formation tube 4 is cut to a desired length and, as shown in FIG. 1, is nipped by the stopper 10. Stopper 10 is adjusted to be horizontal with respect to the surface of the skin. The inside diameter of the tube 8 is not reduced by the stopper 10 nipping it. Incidentally, when the second endoscope 22 or a fluid material is not led into the stomach 2 by using the gastric fistula formation tube 4, it is preferable that a feeding adapter (not shown), or the like, be fitted to the other end portion of the tube 8 on the outer side of the body cavity, and the inside and the outside of the stomach 2 are blocked.

As shown in FIG. 1, when a lesioned part 28 exists on a gastric mucosa 2a in the stomach 2 on the back side, this lesioned part is treated by the two flexible endoscopes 11 and 22 as follows.

At first, when positioning the gastric fistula formation tube 4, the first endoscope 11 is used to confirm the position or size of the lesioned part. For example, air is supplied into the stomach 2 through the inner hole of the gastric fistula formation tube 4, and the stomach 2 is inflated. The first flexible endoscope 11 is orally inserted into the stomach 2. As a treatment tool (insertion member), for example, a high-frequency snare 26 is arranged in one of the forceps channels of the insertion portion 11a of the endoscope 11. The second flexible endoscope 22 is abdominally or transdermally (percutaneouslly) inserted into the stomach 2 through the inner hole of the gastric fistula formation tube 4. As treatment tools (insertion members), for example, a grasping forceps 24 and a non-illustrated injection needle are respectively inserted into the forceps channels of the insertion portion 22a of the endoscope 22. Then, the lesioned part 28 is reconfirmed by using the first and second endoscopes 11 and 22.

Then, for example, a physiological saline is locally injected under the tissue of the lesioned part 28 by the injection needle inserted into the second endoscope 22, and the lesioned part 28 is caused to protuberate so that is can be readily grasped by the grasping forceps 24 inserted through the second endoscope 22. The high-frequency snare 26 inserted into the first endoscope 11 is arranged around the lesioned part 28. After grasping the lesioned part 28 by using the grasping forceps 24 inserted into the second endoscope 22, the lesioned part 28 is upraised by pulling the forceps 24 toward the center of the stomach 2. After binding the lesioned part which is upraised and caused to protuberate by the previously arranged high-frequency snare 26, a high-frequency current is caused to flow through the high-frequency snare 26, and the lesioned part 28 is cut.

Upon completion of such a cutting treatment, with the cut lesioned part 28 being grasped by the grasping forceps 24, the second flexible endoscope 22 is removed from the inside of the body, the lesioned part 28 is collected, and examination is carried out. As a result of inspection of the lesioned part, cutting of the lesioned part 28 is performed depending on it's depth, size or degree of infiltration, thereby terminating the treatment procedure.

Then, after removing the stopper 10 nipping the tube 8, the dome portion 6 is hooked and held by using the high-frequency snare 26 provided to the first endoscope 11, and the gastric fistula formation tube 4 is orally removed.

It is to be noted that description has been given as to the case where the lesioned part 28 is cut by using the high-frequency snare 26 provided to the first endoscope 11 in this embodiment but the cutting treatment tool is not restricted to the high-frequency snare 26. For example, the lesioned part 28 may be peeled and cut off by using a needle-shaped scalpel 30 shown in FIG. 3 as a treatment tool (insertion member). By using the needle-shaped scalpel 30, a larger cutting range can be assured as compared with the case where the lesioned part 28 is cut by using the high-frequency snare 26 shown in FIG. 1.

Therefore, the following can be said with respect to the first embodiment. By orally, abdominally or transdermally inserting and using the respective flexible endoscope 11 and 22, the operability of the treatment apparatus can be improved. Thus, the lesioned part 28 existing on the mucosa 2a or the stomach wall in the stomach 2 can be further securely cut off, and the possibility that the lesioned part 28 is left behind can be suppressed, thereby reducing the possibility of reoccurrence.

By using the flexible endoscope 11 and 22, not only when the lesioned part exists on the back side but also when the lesioned part 28 exists in the vicinity of the abdominal cavity (insertion support tool), this lesioned part 28 can be likewise cut off by operating the insertion portions 11a and 22a.

The technique can be further assuredly carried out by selecting and using the cutting treatment tool such as the high-frequency snare 26 or the needle-shaped scalpel 30 according to depth, size or infiltration degree of the lesioned part 28.

A second embodiment will now be described with reference to FIGS. 4A to 4F. This embodiment is a modification of the first embodiment, and like reference numerals denote like or corresponding parts, thereby omitting repetitive explanation.

Figure 4A:
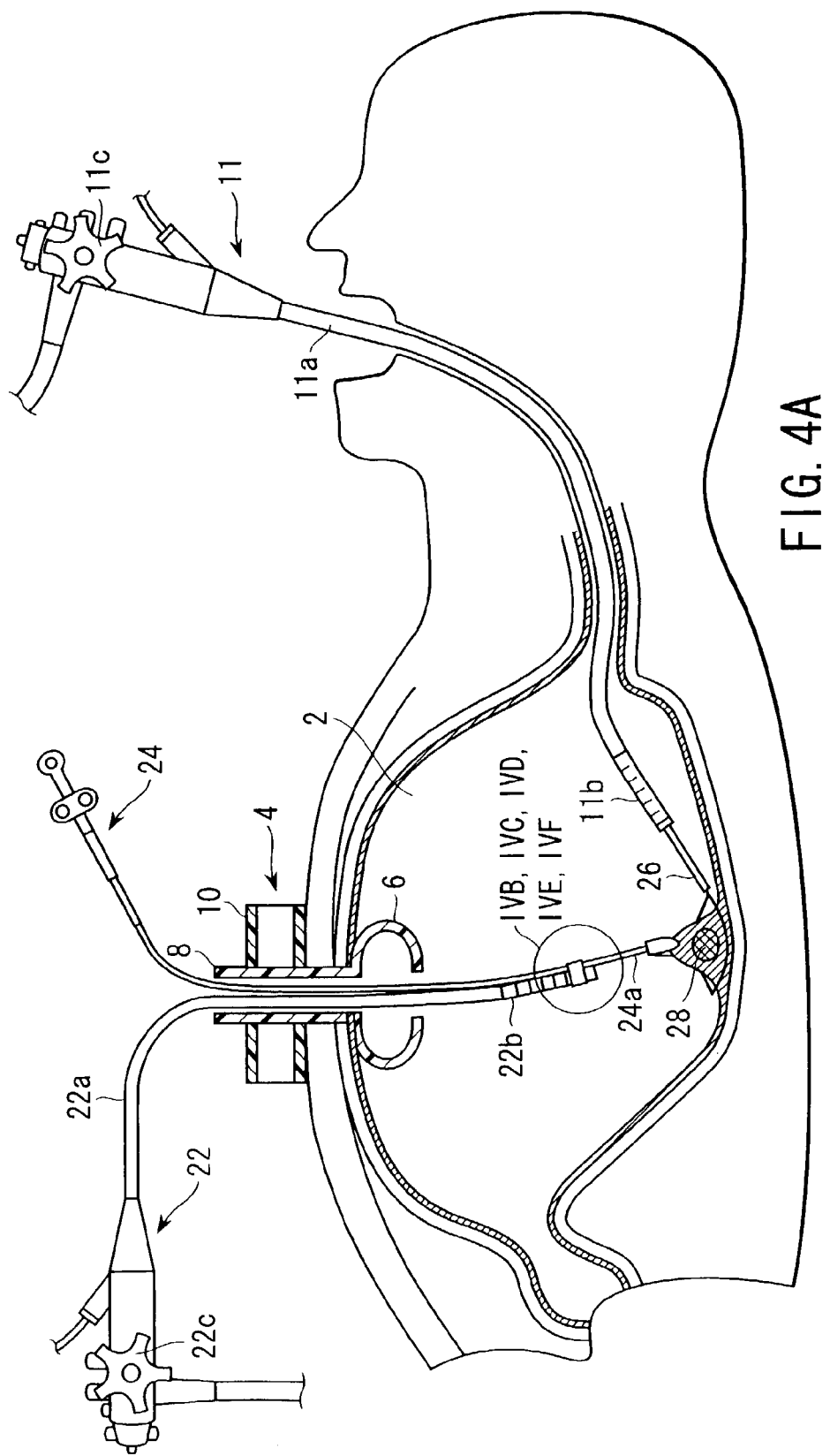
FIG. 4A is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a second embodiment.

As shown in FIG. 4A, in a treatment apparatus according to this embodiment, the first and second flexible endoscopes 11 and 22 are inserted into the stomach 2. Of these endoscopes, an observation optical system is eliminated from the insertion portion 22a of the second flexible endoscope 2, and hence the inside of the stomach 2 cannot be observed using this endoscope 22. Therefore, the second flexible endoscope 22 is used as a lead-in tool which leads a later-described treatment tool (for example, a grasping forceps 24) into the stomach 2. It is to be noted that the insertion portion 22a of the flexible endoscope 22 is formed at least more smaller due to elimination of the observation optical system as compared with the case where the observation optical system is provided.

Figure 4B:
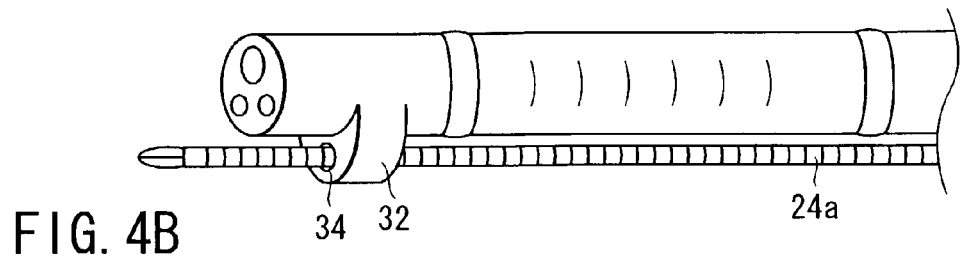
FIG. 4B is a schematic view showing a state that a protrusion portion is provided at an end portion of an insertion portion of the second endoscope, a hole is formed along this insertion portion and a grasping forceps is arranged in this hole.

Moreover, as shown in FIG. 4B, a protrusion portion 32 which protrudes toward the side with respect to the axial direction is provided in the vicinity of the end of the insertion portion 22a of the second flexible endoscope 22. A hole 34 is provided in this protrusion portion 32 in a direction along the axial direction of the insertion portion 22a. The insertion portion 24a of the grasping forceps 24 is inserted into this hole 34.

As shown in FIG. 4A, when the lesioned part 28 exists on the gastric mucosa 2a in the stomach 2 on the back side, this lesioned part 28 is treated by the two flexible endoscopes 11 and 22 as follows.

At first, like the first embodiment, after confirming the position and size of the lesioned part 28 in the stomach 2 by using the first endoscope 11, the gastric fistula formation tube 4 is provided. Then, after inflating the stomach 2 through the gastric fistula formation tube 4, the first flexible endoscope 11 is orally inserted into the stomach 2.

Then, for example, the high-frequency snare 26 is arranged in one of the forceps channels of the insertion portion 11a of the endoscope 11. With the grasping forceps 24 being inserted in the above-described hole 24, the second flexible endoscope 22 is inserted into the stomach 2 through the inner hole of the gastric fistula formation tube 4. Thereafter, the lesioned part 28 is reconfirmed by using the first flexible endoscope 11.

Then, the grasping forceps 24 arranged along the second flexible endoscope 22 is led to the lesioned part 28 by using the first flexible endoscope 11. That is, it is led to the lesioned part 28 while monitoring the end portion of the second endoscope 22 and the end portion of the grasping forceps 24 by using the first endoscope 11. Then, the end portion of the high-frequency snare 26 provided to the first flexible endoscope 11 is arranged so as to surround the lesioned part 28. The lesioned part 28 is grasped by the grasping forceps 24 and pulled toward the center of the stomach 2, the high-frequency snare 26 is tied, and the lesioned part 28 is cut by passing a high-frequency current therethrough. Upon completion of such a treatment, the second flexible endoscope 22 is removed from the body with the cut part being grasped, and the lesioned part is collected. The gastric fistula formation tube 4 is orally removed as described in connection with the first embodiment according to need.

Therefore, the following can be said with respect to this embodiment. Since the observation optical system is removed from the second flexible endoscope 22 and a forceps such as the grasping forceps 24 is arranged outside the insertion portion 22a, the insertion portion 22a itself can be made thinner. In addition, various kinds of forceps with various dimensions (thicknesses) can be used, irrespective of the size of the forceps channel of the endoscope 22.

It is to be noted that the structure of arranging the forceps along the insertion portion 22a is not restricted to the one mentioned above, and the following structures can be adopted, for example.

Figure 4C:
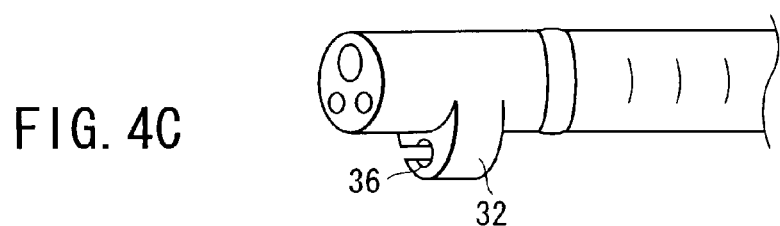
FIG. 4C is a schematic view showing a state that a hook portion is provided to the protrusion portion depicted in FIG. 4B.

As shown in FIG. 4C, a hook portion 36 to which the grasping forceps 24 is latched is provided to the above-described protrusion portion 32, for example. The above-described grasping forceps 24 is latched to the hook portion 36, and the medical treatment may be likewise performed.

Figure 4D:
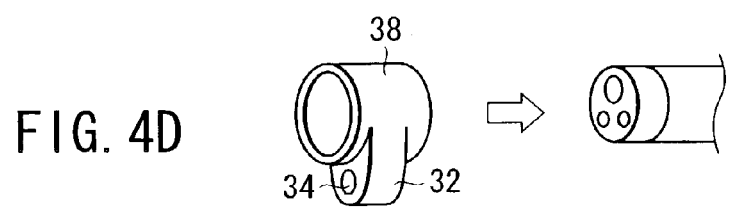
FIG. 4D is a schematic view showing that a cylindrical member which can be fitted is provided at the end portion of the second endoscope and a protrusion portion similar to that depicted in FIG. 4B is provided to this cylindrical member.

Additionally, as shown in FIG. 4D, a cylindrical member 28 is detachably formed at the end portion of the second flexible endoscope 22. A protrusion portion 32 which protrudes toward the side is provided to the cylindrical member 28. A hole 34 in a direction along the insertion portion 24a of the grasping forceps 24 is provided to this protrusion portion 32. The insertion portion 24a of the grasping forceps 24 can be inserted into this hole 34.

Figure 4E:
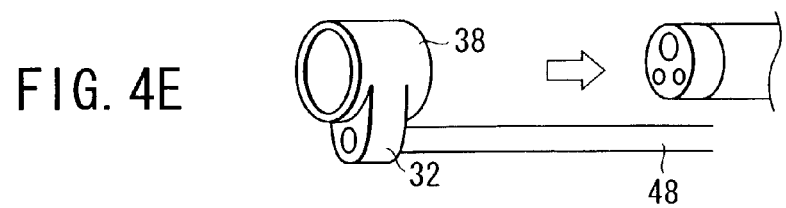
FIG. 4E is a schematic view showing a state that a guide tube is arranged in the hole illustrated in FIG. 4D.

Further, as shown in FIG. 4E, a guide tube 42 extends through the hole 34 provided to the cylindrical member 38 illustrated in FIG. 4D toward the rear side of the insertion portion 22a of the second flexible endoscope 22. A desired treatment tool such as the grasping forceps 24 is inserted into the guide tube 42 and caused to protrude from the end portion of the guide tube 42.

Figure 4F:
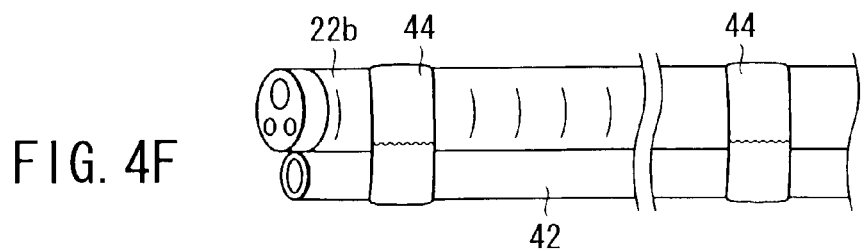
FIG. 4F is a schematic view showing a state that the guide tube is arranged along the insertion portion of the second flexible endoscope by using surgical tape.

Furthermore, as shown in FIG. 4F, the second flexible endoscope 22 and the guide tube 42 are provided along the insertion portion 22a by surgical tape (medical tape) 44. Like FIG. 4E, a desired treatment tool such as the grasping forceps 24 is inserted into the guide tube 42 and caused to protrude from the end portion of the guide tube 42.

It is to be noted that description has been give as to the case where the observation optical system is eliminated and the insertion portion 22a of the second flexible endoscope 22 is formed thin but it is also preferable that the observation optical system is provided as with a regular flexible endoscope and the medical treatment is carried out while observing the lesioned part 28 by using the two endoscopes 11 and 22. Alternatively, the forceps channel may be eliminated, as well as the observation optical system. Moreover, the stomach 2 may be inflated by supplying air into the stomach 2 through the first flexible endoscope 11.

A third embodiment will now be described with reference to FIGS. 5A and 5B. This embodiment is a modification of the first and second embodiments, and like reference numerals denote like or corresponding parts, thereby omitting a detailed explanation.

Figures 5A, 5B:
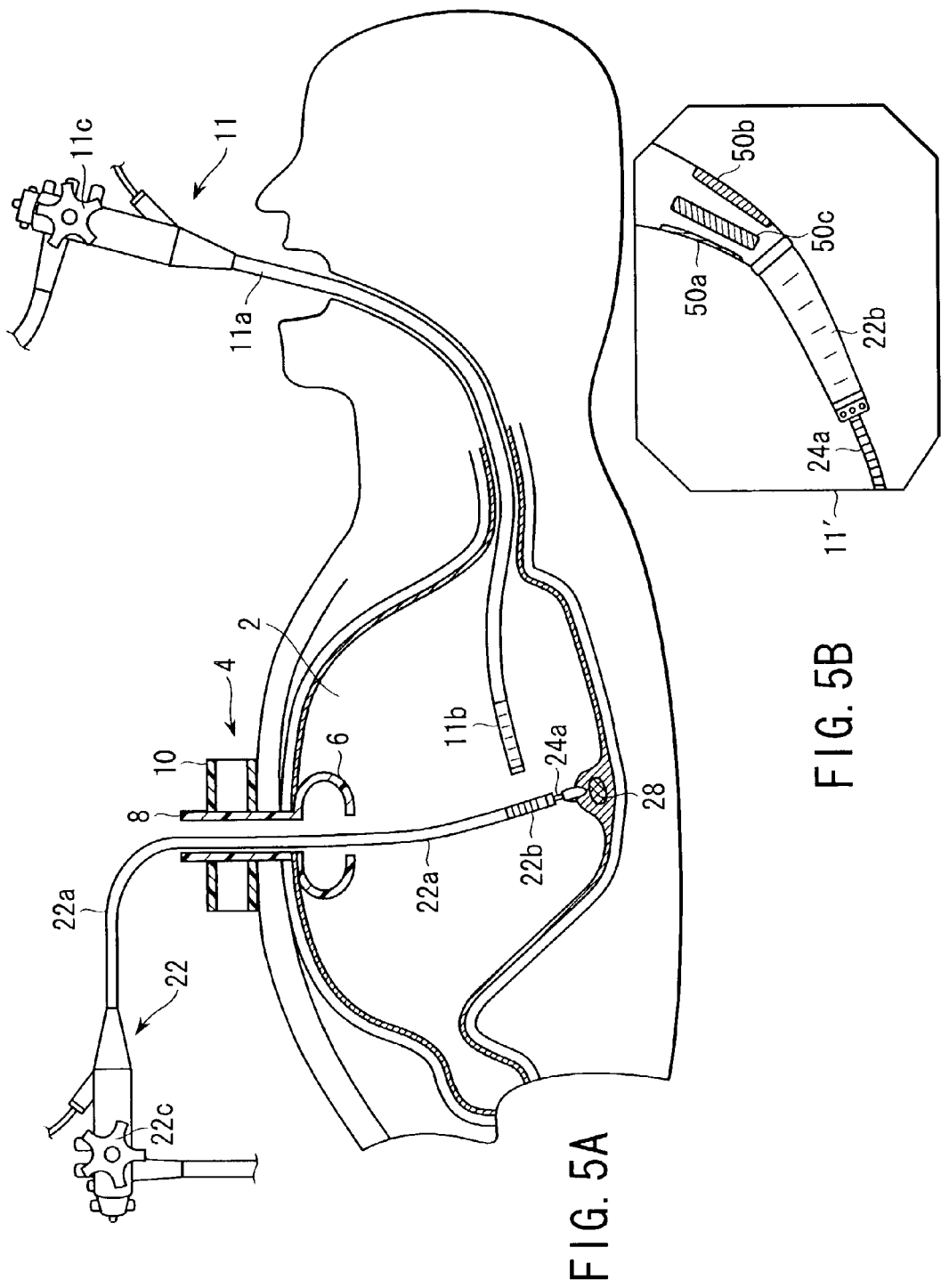
FIG. 5A is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a third embodiment.
FIG. 5B is a schematic view showing the vicinity of a curved portion of the second endoscope by the first flexible endoscope.

As shown in FIG. 5A, in a treatment apparatus according to this embodiment, the first and second flexible endoscopes 11 and 22 are inserted into the stomach 2. In addition, as shown in FIG. 5B, four identification labels 50 are provided in the vicinity of the base end portion of the curved portion 22b of the second flexible endoscope 22. Assuming that the circumferential direction of the second flexible endoscope 22 is divided into four directions, i.e., an up (U) direction 50a, a down (D) direction 50b, a right (R) direction (not shown), and a left (L) direction 50c every 90°, the identification labels 50 are separated by colors, e.g., red, blue, yellow, green or the like. By observing such identification labels 50 by using the first flexible endoscope 11, an operator of the first flexible endoscope 11 can readily instruct an operator of the second flexible endoscope 22 of the direction in which the curved portion 22b of the second flexible endoscope 22 should be moved.

When the lesioned part 28 exists on the gastric mucosa in the stomach 2 on the back side, this lesioned part 28 is treated as follows by the two flexible endoscopes 11 and 22.

At first, like the first embodiment, after confirming the position and dimensions of the lesioned part 28 in the stomach 2 by using the first endoscope 11, the gastric fistula formation tube 4 is positioned. Then, after inflating the stomach 2 through the gastric fistula formation tube 4, the first flexible endoscope 11 is orally inserted into the stomach 2, and the second flexible endoscope 22 having the grasping forceps 24 inserted into the forceps channel is inserted into the stomach 2 through the inner hole of the gastric fistula formation tube 4. Subsequently, the lesioned part 28 is reconfirmed by using the first flexible endoscope 11.

Thereafter, as shown in FIG. 5B, the end portion of the insertion portion 22b of the second flexible endoscope 22 is displayed in a visual field 11' by the observation optical system by using this system provided to the first endoscope 11. The lesioned part 28 is grasped by the grasping forceps 24 by moving or bending the curved portion 22b of the second flexible endoscope 22 toward the lesioned part 28 in accordance with the identification labels 50. That is, the second endoscope is led to a desired position by using the first endoscope 11. Then, with the lesioned part 28 being grasped by the grasping forceps 24 provided to the second endoscope 22 and pulled toward the center of the stomach 2, the lesioned part 28 is cut by using a high-frequency snare (not shown) or the like arranged to the first endoscope 11.

Meanwhile, as to such an identification label 50, a groove having a shape like a plus symbol, a groove having a shape like a minus symbol, a groove having a triangular shape and the like may be provided in the same color at the end portion of the curved portion 22b or the insertion portion 22a, and changed by the both of the shape and color of the identification label 50. Further, separation by color is not restricted to that mentioned above, and any other separation color may be carried out as long as recognition is facilitated by using the observation optical system of the first flexible endoscope 11.

Therefore, the following can be said with respect to this embodiment. When an operator of the first endoscope 11 instructs an operator of the second endoscope 22 of an operation, the operator of the first endoscope 11 can easily recognize the direction in which the curved portion 22b of the second endoscope 22 should be moved. Therefore, the operator of the first endoscope 11 can easily work with the operator of the second endoscope. Accordingly, the medical treatment procedure can be smoothly advanced, thereby shortening the treatment time.

A fourth embodiment will now be described with reference to FIGS. 6 and 7. This embodiment is a modification of the first embodiment, and like reference numerals denote like or corresponding parts, thereby omitting the detailed explanation.

Figure 6:
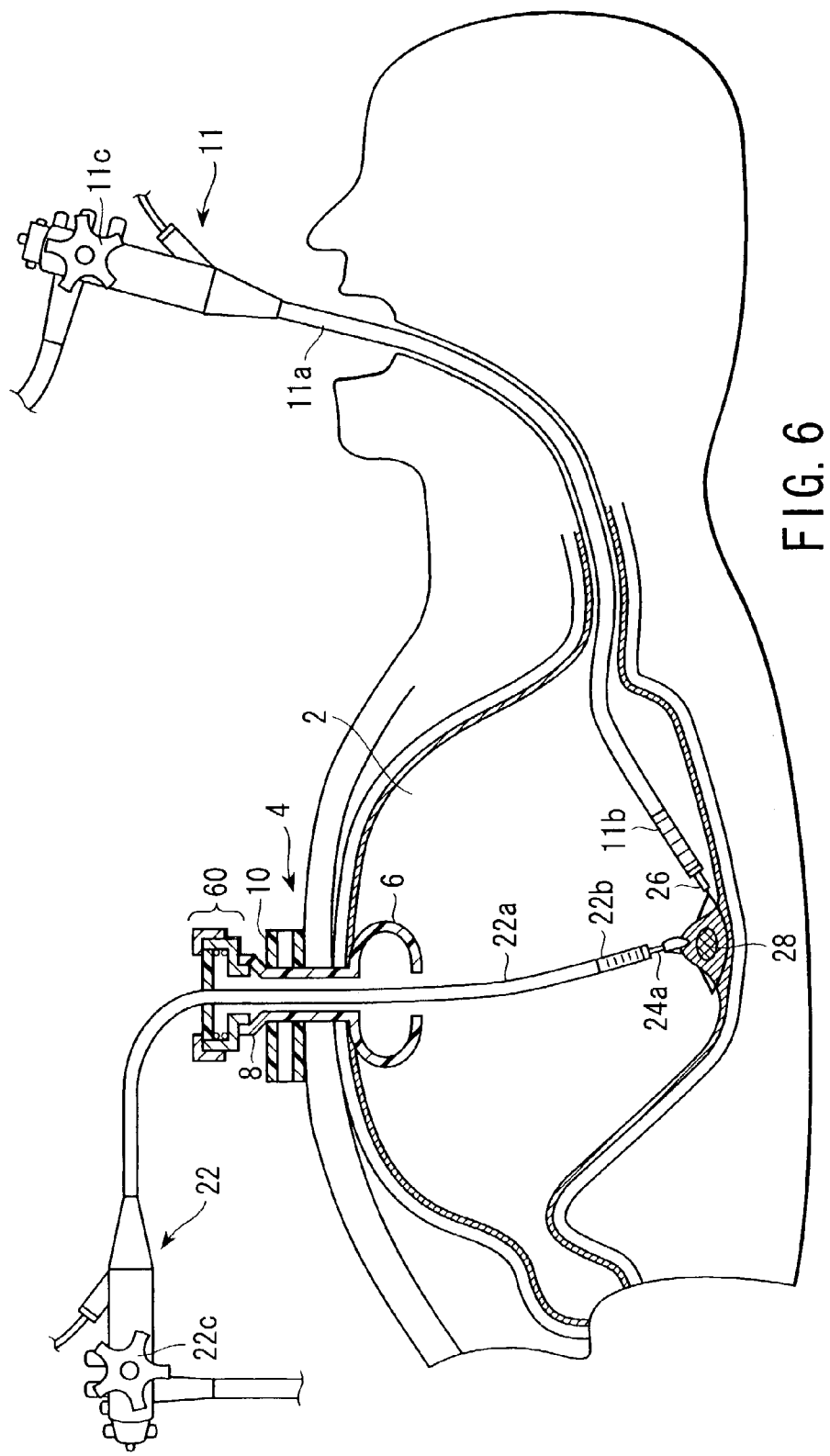
FIG. 6 is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a fourth embodiment.
Figure 7:
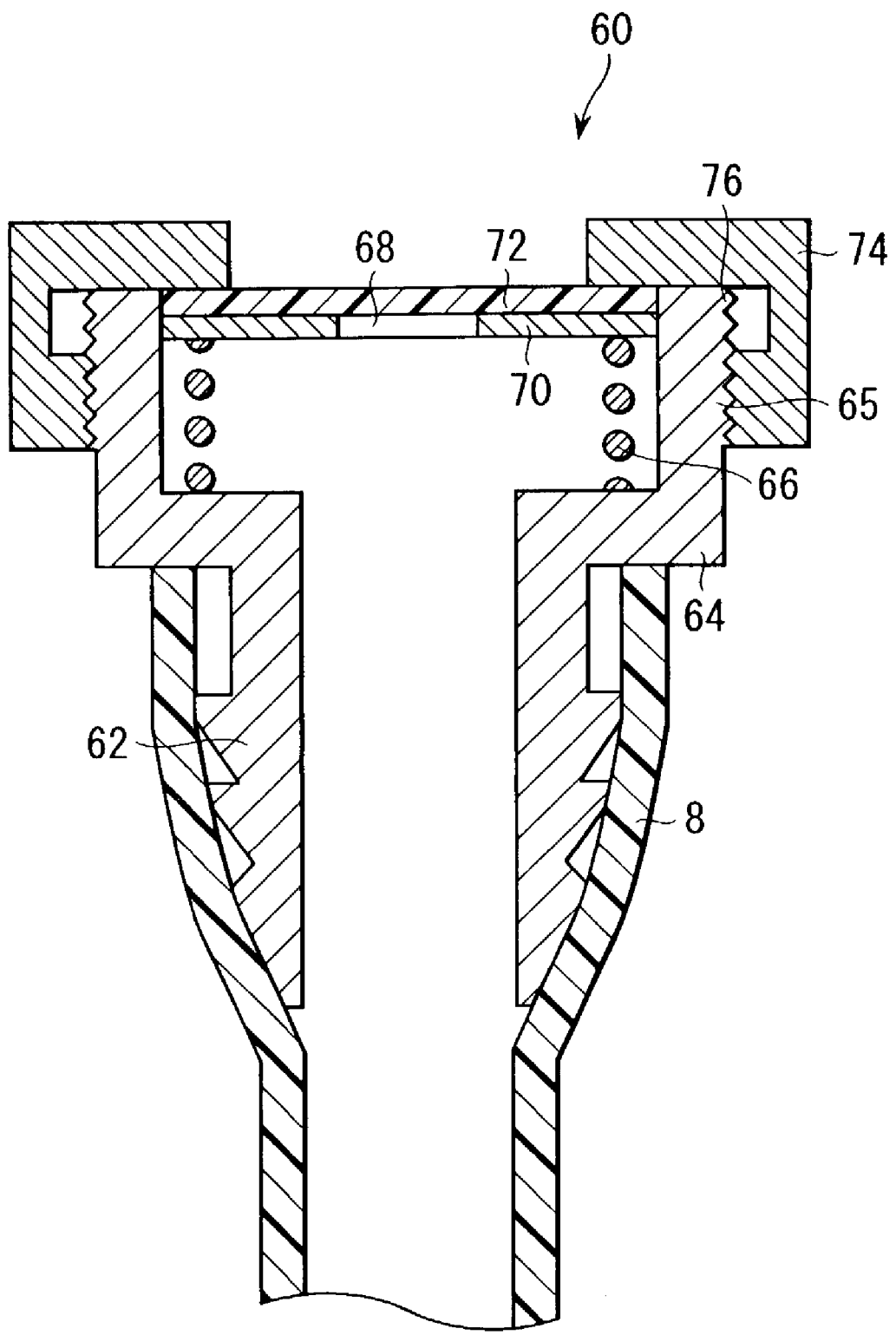
FIG. 7 is a cross-sectional view showing a mouth ring fitted to the gastric fistula formation tube illustrated in FIG. 6.

As shown in FIG. 6, in a treatment apparatus according to this embodiment, the first and second flexible endoscopes 11 and 22 are inserted into the stomach 2.

A mouth ring 60 is attached to the other end portion (open end portion) of the tube 8 of the gastric fistula formation tube 4. As shown in FIG. 7, this mouth ring 60 includes, on the inner periphery of the open end portion of the tube 8, a tubular portion 62 having a protrusion portion with which the outer periphery of the tube 8 on the end portion side is engaged. A flange portion 64 protruding toward the outer periphery of the tubular portion 62 is formed at the base end portion of the tubular portion 62. The open end portion of the tube 8 is in contact with the flange portion 64 from one side.

A cylindrical portion 65 with a larger diameter than that of the tubular portion 62 is formed on the other side of the flange portion 64. Furthermore, an elastic member with a larger diameter than that of the tubular portion 62, e.g., a spring 66 is provided on the inner side of the cylindrical portion 65 in such a manner that one end of this member is in contact with the flange portion 64. To the other end of this spring is provided a rigid support plate 70, such as one made of plastic or metal, with a circular hole 68 at it's center. The hole 68 has a larger diameter than the outside diameter of the insertion portion 22a of the second flexible endoscope 22. This support plate 70 is pressed toward the upper side in FIG. 7 by the spring 66. A seal member 72 consisting of an elastic member, such as a rubber material, is provided on the support plate 70. At the center of the seal member 72 is formed a through hole or slit which has a circular shape, a plus symbol shape or a minus symbol shape with a smaller diameter than the outside diameter of the insertion portion 22a of the second endoscope 22. A screw thread 76 is formed on the outer periphery of the cylindrical portion 65, and a lid 74 is screwed to the screwing portion 76 so as to press the seal member 72 and the support plate 70 against the impetus of the spring 66.

When the insertion portion 22a of the second endoscope 22 is inserted into such a mouth ring 60, the insertion portion 22a is gradually inserted into the stomach 2 with the seal member 72 being appressed against the insertion portion 22a. At this moment, the insertion portion 22a is moved toward the inside of the stomach 2 against the impetus of the spring 66. That is, the insertion portion 22a of the endoscope 22 is pressed in the direction of thrusting from the inside to the outside of the stomach 2 in the state that it is appressed against the seal member 72. Therefore, when the lesioned part 28 is grasped by the grasping forceps 24, the lesioned part 28 is pulled (withdrawn) toward the outside of the stomach 2.

When the lesioned part 28 exists on the gastric mucosa in the stomach 2 on the back side, the lesioned part 28 is treated by the two flexible endoscopes 11 and 22 in the same way as that described in connection with the first embodiment.

Therefore, the following can be said with respect to this embodiment. When the second flexible endoscope 22 is inserted into the stomach 2 through the mouth ring 60, the insertion portion 22a is appressed against the seal member 72. The support plate 70 and the seal member 72 are pressed toward the upper part by the spring 66. Therefore, the insertion portion 22a of the second endoscope 22 is indirectly pressed upwards, and the lesioned part is caused to be pulled upward by only holding the second endoscope 22 with the lesioned part 28 being grasped by the grasping forceps 24. Thus, the lesioned part 28 can be readily cut.

Moreover, when the insertion portion 22a of the endoscope 22 is inserted, the insertion portion is appressed against the outside diameter of the seal member 72, and hence air used to inflate the stomach 2 hardly leaks to the outside.

A fifth embodiment will now be described with reference to FIGS. 8A to 8C. This embodiment is a modification of the first embodiment, and like reference numerals denote like or corresponding parts, thereby omitting the detailed explanation.

As shown in FIG. 8A, in a treatment apparatus according to this embodiment, the first and second flexible endoscopes 11 and 22 are inserted into the stomach 2. As shown in FIG. 8B, a holding portion 80a which protrudes from the vicinity of the end of the insertion portion 22a of the second endoscope 22 toward the side is provided in the vicinity of this end as shown in FIG. 8B. As a treatment tool (insertion member), for example, a grasping forceps 82 is provided to the forceps channel at the end of the insertion portion 11a of the first endoscope 11. When the holding portion 80a as the grasping portion of the second endoscope 22 is grasped by operating the grasping forceps 82, the insertion portion 22a of the second endoscope 22 is guided to a desired position by operating the operation portion 11c of the first endoscope 11.

When the lesioned part 28 exists on the gastric mucosa in the stomach 2 on the back side, the lesioned part 28 is treated by the two flexible endoscopes 11 and 22 as follows.

At first, like the first embodiment, after confirming the position and dimensions of the lesioned part 28 in the stomach 2 by using the first endoscope 11, the gastric fistula formation tube 4 is positioned. Then, after inflating the stomach 2 through the gastric fistula formation tube 4, the first flexible endoscope 11 having the grasping forceps 82 inserted into the forceps channel is orally inserted into the stomach 2, and the second flexible endoscope 22 is inserted into the stomach 2 through the inner hole of the gastric fistula formation tube 4. Subsequently, the lesioned part 28 is reconfirmed by the first flexible endoscope 11.

Thereafter, the holding portion 80a provided at the end portion of the insertion portion 22a of the second flexible endoscope 22 is held by the grasping forceps 82. In this state, the end portion of the insertion portion 22a of the second flexible endoscope 22 is led toward the lesioned part 28 by operating the first flexible endoscope 11. Therefore, in this embodiment, the observation optical system may be eliminated from the second endoscope 22. Thereafter, for example, a high-frequency snare (not shown) or the like is arranged in the first endoscope 11, a grasping forceps (not shown) or the like is arranged in the second endoscope 22, and the lesioned part 28 is cut by joint operation of the endoscopes 11 and 12.

In order to grasp the second endoscope 22 by the grasping forceps 82 of the first endoscope 11 and guide it to a desired position, the tool for such a purpose is not restricted to the holding portion 80a provided at the end portion of the insertion portion 22a of the second endoscope 22. For example, as shown in FIG. 8C, the curved portion 22b may include a blade portion 80b or the like which is formed of metal, the blade portion 80b may be grasped by the grasping forceps 82 or a basket grasping forceps (not shown) provided to the first endoscope 11, and the second endoscope 22 may be guided to a desired position. Since this blade portion 80b is inserted into the stomach 2 through the inner hole of the gastric fistula formation tube 4, it can be inserted into the stomach 2 without damaging the living body.

Therefore, the following can be said with respect to this embodiment. When the lesioned part 28 exists on the abdominal side, since the insertion portion 22a of the second endoscope 22 is also provided at a desired position by moving the insertion portion 11a by manipulating the first endoscope 11, the trouble of operation by an operator can be reduced by half.

In addition, when the observation optical system is eliminated from the second endoscope 22, leading to the lesioned part 28 by using the first endoscope 11 or the like is facilitated.

A sixth embodiment will now be described with reference to FIG. 9. This embodiment is a modification of the first embodiment, and like reference numerals denote like or corresponding parts, thereby omitting the detailed explanation.

Figure 9:
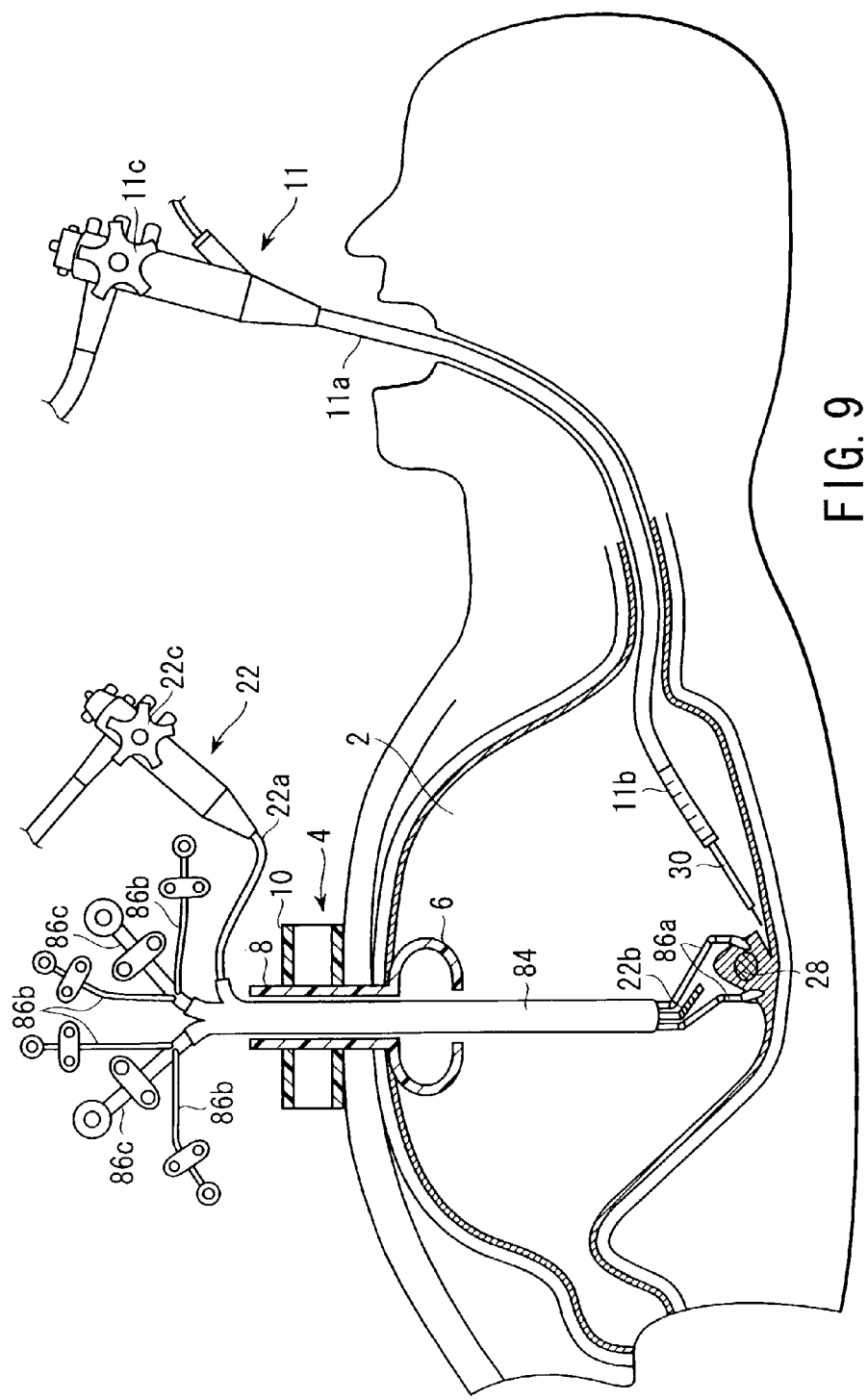
FIG. 9 is a schematic cross-sectional view showing a treatment apparatus which orally leads a first flexible endoscope into an organ, abdominally or transdermally leads a second flexible endoscope into the organ and gives a medical treatment to a lesioned part by using these two flexible endoscopes according to a sixth embodiment.

As shown in FIG. 9, in a treatment apparatus according to this embodiment, the first flexible endoscope 11 is orally inserted into the stomach 2. Further, a tubular body 84 as a catheter is inserted into the gastric fistula formation tube 4. For example, three lumens (not shown) are provided to this tubular body 84. For example, a grasping forceps 86 as a treatment tool (insertion member) having a polyarticular arm is provided to each of the two lumens in these three lumens, and the second endoscope 22 is provided in the remaining lumen. This grasping forceps 86 includes an arm portion 86a protruding from the end of the tubular body 84, and an arm operation portion 86b provided at the base end of the tubular body 84 so as to operate the arm portion 86a. Additionally, this grasping forceps 86 includes, at the base end of the tubular body 84, an opening/closing operation portion 86c which operates to open/close a cup provided at the end of the arm portion 86a. Further, the second endoscope 22 is used as the observation optical system. Therefore, providing only the observation optical system to the insertion portion 22a of the second endoscope 22 can suffice. On the other hand, a needle-shaped scalpel 30 is provided to the insertion portion 11a of the first endoscope 11.

When the lesioned part 28 exists on the gastric mucosa in the stomach 2 on the back side, this lesioned part is treated by the two flexible endoscopes 11 and 22 as follows.

At first, like the first embodiment, after confirming the position and dimensions of the lesioned part 28 in the stomach 2 by using the first endoscope 11, the gastric fistula formation tube 4 is positioned. Then, the stomach 2 is inflated through the gastric fistula formation tube 4. Thereafter, the first flexible endoscope 11 is orally inserted into the stomach 2, and the tubular body 84 is inserted into the stomach 2 through the gastric fistula formation tube 4. Then, the lesioned part 28 is reconfirmed by using the first flexible endoscope 11.

Then, the two grasping forcipes 86 and the second flexible endoscope 22 are respectively inserted into the non-illustrated lumens of the tubular body 84. The lesioned part 28 is grasped and lifted up using the two grasping forcipes 86 by manipulating the arm operation portion 86b and the opening/closing operation portion 86c while confirming the lesioned part 28 by the second endoscope 22. The lesioned part 28 lifted up is cut by using the needle-shaped scalpel 30 provided to the first endoscope 11.

Therefore, the following can be said with respect to this embodiment. By inserting the two grasping forcipes 86 through one hole (gastric fistula formation tube 4), the lesioned part 28 can be extensively lifted up when the lesioned part 28 is wide. Thus, the lesioned part 28 can be readily cut by using the first endoscope 11.

A seventh embodiment will now be described with reference to FIGS. 10A and 10B. This embodiment is a modification of the first embodiment, and like reference numerals denote like or corresponding parts, thereby omitting the detailed description.

As shown in FIG. 10A, in a treatment apparatus according to this embodiment, the first and second flexible endoscopes 11 and 22 are inserted into the stomach 2. Further, a seal member 98 is fitted to the upper end portion of the gastric fistula formation tube 4 which leads the second flexible endoscope 22 into the stomach 2. This seal member 98 includes, e.g., two holes or slits 98a and 98b. The insertion portion 22a of the endoscope 22 and a grasping forceps 100 which is, e.g., a rigid treatment tool (insertion member) are respectively inserted into the holes 98a and 98b. The insertion portion 22a of the second endoscope 22 and the insertion portion of the rigid grasping forceps 100 are appressed against the seal member 98 so that and air in the stomach 2 hardly leaks to the outside of the body.

Furthermore, as shown in FIG. 10B, an object lens 90 is provided at the central part of the insertion portion 11a of the first endoscope 11. A pair of light guides 92 are provided on the sides of the object lens 90. Moreover, an air supply/water supply nozzle 94 is provided to the insertion portion 11a. Then, a treatment tool guide groove 96 is formed between each light guide 92 and the air supply/water supply nozzle 94. In addition, the treatment tool guide grooves 96 are also provided at positions which are symmetrical to the object lens 90 at the center. For example, a high-frequency snare 26 or a needle-shaped scalpel 30 is provided in each of these treatment tool guide grooves 96. The high-frequency snare 26 or the needle-shaped scalpel 30 is selectively led out and used from the groove portion opening portion 97 toward the direction of the end of the insertion portion 11a.

When the lesioned part 28 exists on the gastric mucosa in the stomach 2 on the back side, this lesioned part 28 is treated by the two flexible endoscopes 11 and 22 as follows.

At first, like the first embodiment, after confirming the position and dimensions of the lesioned part 28 by using the first endoscope 11, the gastric fistula formation tube 4 is positioned. Then, after inflating the stomach 2 through the gastric fistula formation tube 4, the first flexible endoscope 11 is orally inserted into the stomach 2, and the second flexible endoscope 22 having the grasping forceps 24 inserted therethrough and the rigid grasping forceps 100 are inserted into the stomach 2 through the inner hole of the gastric fistula formation tube 4. Subsequently, the lesioned part 28 is confirmed by using the first flexible endoscope 11.

Thereafter, the lesioned part 28 is grasped by using the grasping forceps 24 while confirming the lesioned part 28 by the second flexible endoscope 22, and it is also grasped by the rigid grasping forceps 100. The lesioned part 28 is lifted up in the grasped state. Then, any one of the high-frequency snare 26 and the needle-shaped scalpel 30 provided in the treatment tool guide grooves 96 of the first flexible endoscope 11 is selected in accordance with the dimensions of the lesioned part 28, and the lesioned part 28 is cut. Thereafter, the grasping forceps 24 provided in the second flexible endoscope 22 or the rigid grasping forceps 100 is used to collect the cut lesioned part 28, and examination is carried out.

Therefore, the following can be said with respect to this embodiment. When the treatment tool guide grooves 96 are provided along the insertion portion 11a of the first flexible endoscope 11 and some treatment tools are provided in the treatment tool guide grooves 96, the treatment tool is selected and used in accordance with the size of the lesioned part 28.

An eighth embodiment will now be described with reference to FIGS. 11A and 11B. This embodiment is a modification of the seventh embodiment, and like reference numerals denote like or corresponding parts, thereby omitting the detailed explanation.

Figures 11A, 11B:
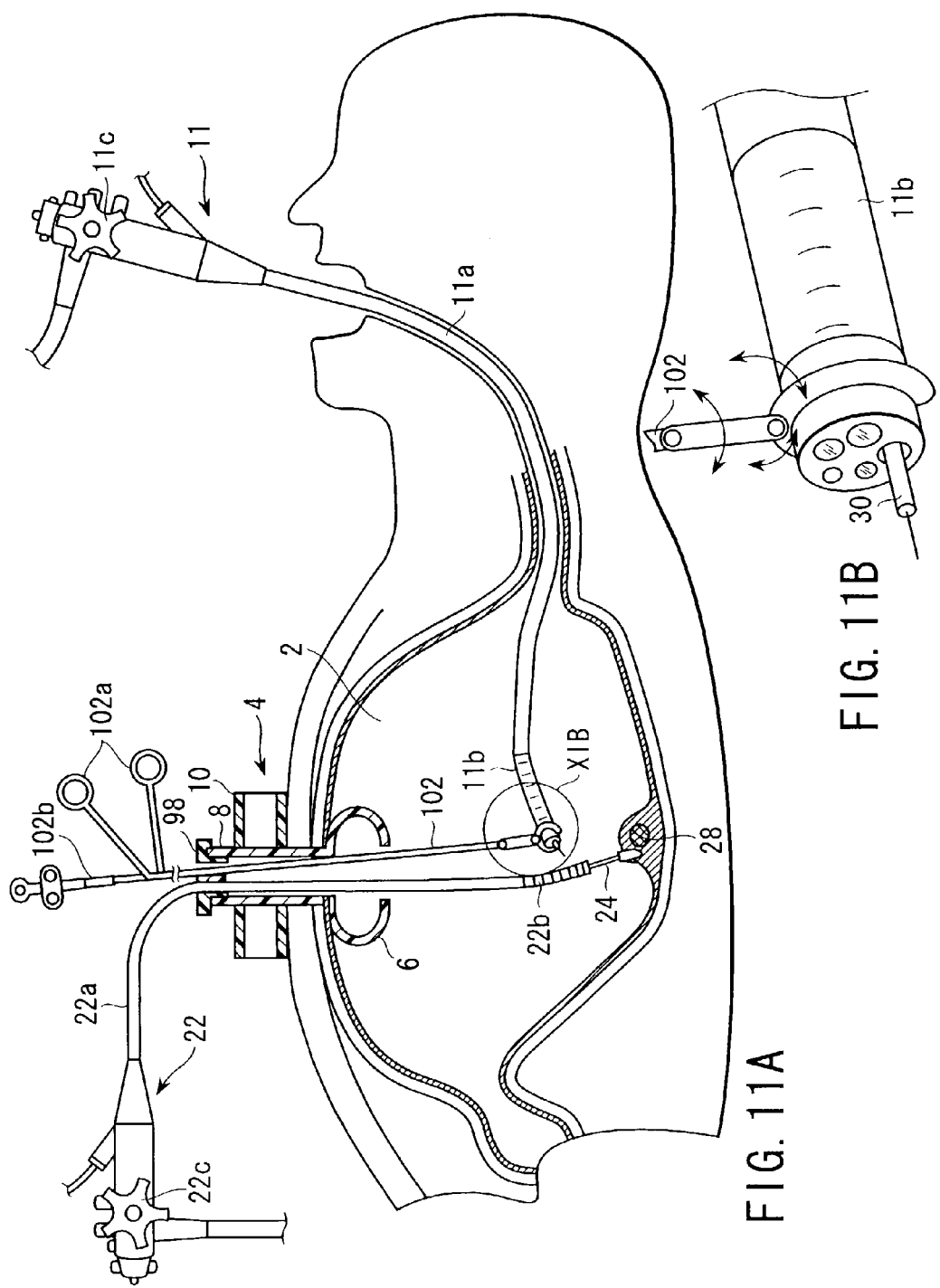
FIG. 11A is a schematic cross-sectional view showing a treatment apparatus which orally leads a first flexible endoscope into an organ, abdominally or transdermally leads a second flexible endoscope and a rigid grasping forceps into the organ and gives a medical treatment to a lesioned part by using these two flexible endoscopes and the rigid grasping forceps according to an eighth embodiment.
FIG. 11B is a schematic view showing that the curved portion can be led in a desired direction by grasping the first flexible endoscope by the rigid grasping forceps.

As shown in FIG. 11A, in a treatment apparatus according to this embodiment, the first and second flexible endoscopes 11 and 22 are inserted into the stomach 2. The needle-shaped scalpel 30 is provided in the insertion portion 11a of the first endoscope 11 so as to be operable.

Moreover, like the seventh embodiment, the seal member 98 is fitted to the upper end portion of the gastric fistula formation tube 4. Into respective holes or slits 98a and 98b of the seal member 98 are inserted the insertion portion 22a of the second endoscope 22 and the grasping forceps 102 which is a rigid treatment tool (insertion member), respectively. An opening/closing operation portion 102a and a swiveling operation portion 102b are provided to the rigid grasping forceps 102 and, as shown in FIG. 11B, the end of this grasping forceps is formed so as to be capable of being opened/closed and swiveling.

When the lesioned part 28 exists on the gastric mucosa in the stomach 2 on the back side, the lesioned part 28 is treated by the two flexible endoscopes 11 and 22 as follows.

Like the first embodiment, after confirming a position and a size of the lesioned part 28 in the stomach 2 by using the first endoscope 11, the gastric fistula formation tube 4 is positioned. Then, after inflating the stomach 2 through the gastric fistula formation tube 4, the first flexible endoscope 11 is orally inserted into the stomach 2, and the second flexible endoscope 22 and the grasping forceps 102 are inserted into the stomach 2 through the inner hole of the gastric fistula formation tube 4.

Then, the lesioned part 28 is confirmed by using the second endoscope 22 and grasped and lifted up by the grasping forceps 24. By manipulating the opening/closing operation portion 102a and the swiveling operation portion 102b of the rigid grasping forceps 102, the end portion of the insertion portion 11a of the first endoscope 11 is grasped as shown in FIG. 11B and led toward the lesioned part 28. Then, the lesioned part 28 lifted up by using the second endoscope 22 is cut out by using the needle-shaped scalpel 30 provided to the first endoscope 11. Thereafter, the lesioned part 28 grasped by the grasping forceps 24 of the second endoscope is collected, and examination is carried out.

It is to be noted that description has been given as to the case where the first endoscope 11 is grasped in this embodiment but a part in the vicinity of the end of the insertion portion 22a of the second endoscope 22 may be grasped and likewise led to a desired position.

Therefore, the following can be said with respect to this embodiment. By leading the first endoscope 11 toward the lesioned part 28 by using the rigid grasping forceps 102, an operator of the second endoscope 22 can easily give an instruction to an operator of the first endoscope 11.

Figure 13:
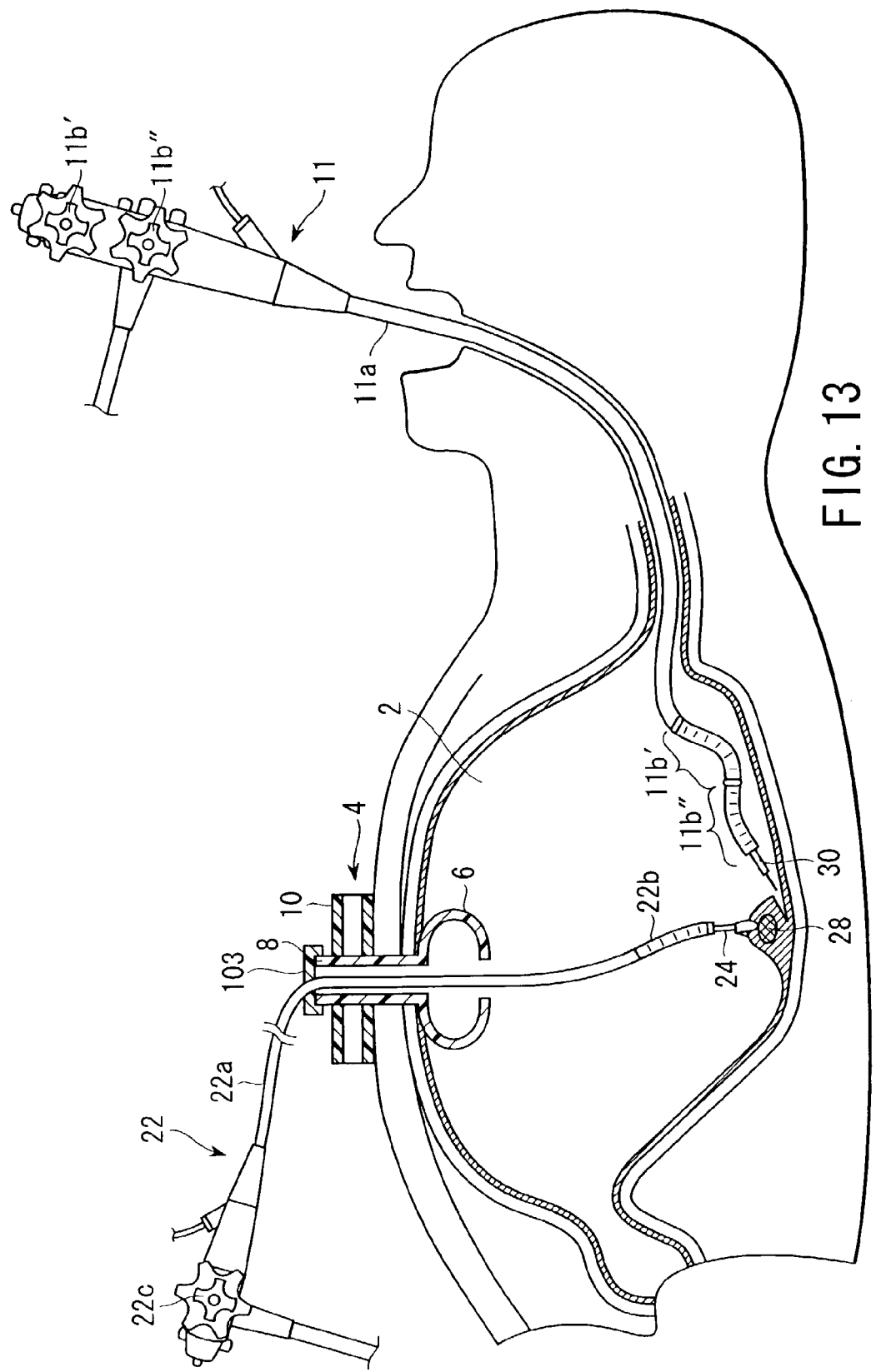
FIG. 13 is a schematic cross-sectional view showing a modification of the treatment apparatus according to the ninth embodiment.
Figure 14:
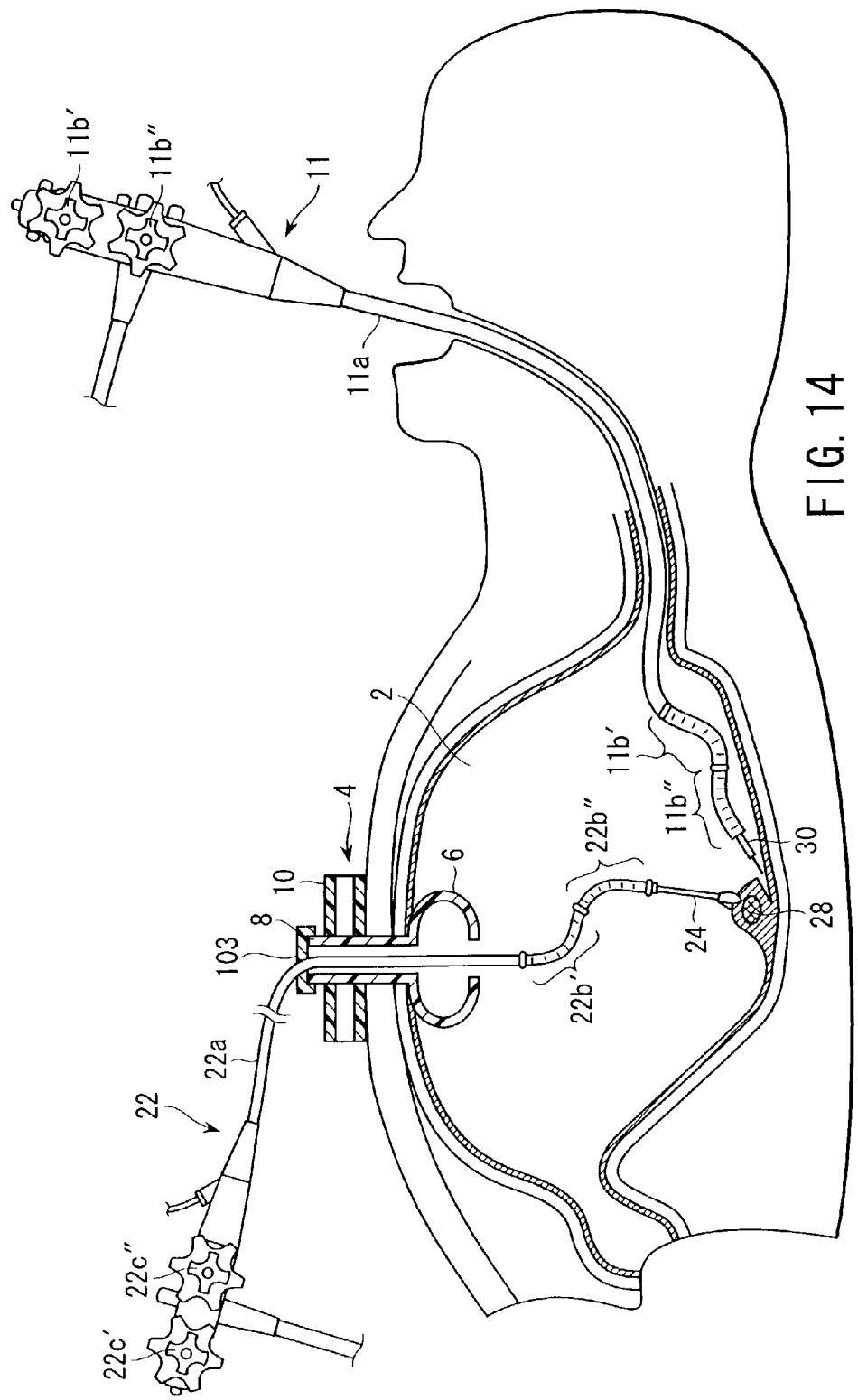
FIG. 14 is a schematic cross-sectional view showing the modification of the treatment apparatus according to the ninth embodiment.

A ninth embodiment will now be described with reference to FIGS. 12 to 14. This embodiment is a modification of the first embodiment, and like reference numerals denote like or corresponding parts, thereby omitting the detailed explanation.

Figure 12:
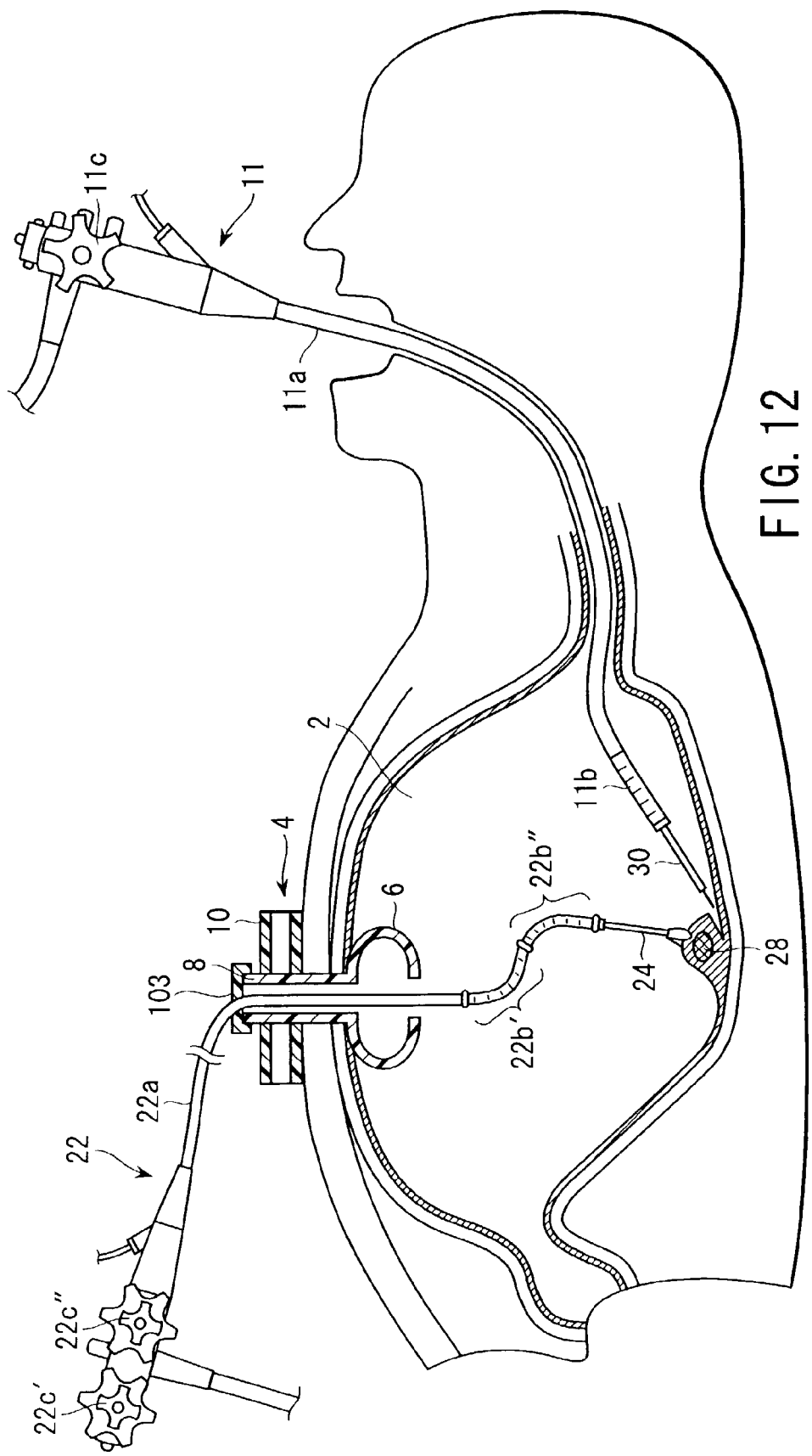
FIG. 12 is a schematic cross sectional view showing a treatment apparatus which orally leads a first flexible endoscope into an organ, abdominally or transdermally leads a second flexible endoscope into the organ and gives a medical treatment to a lesioned part by using these two flexible endoscopes according to a ninth embodiment.

As shown in FIG. 12, in a treatment apparatus according to this embodiment, the first and second flexible endoscopes 11 and 22 are inserted into the stomach 2. The curved portion 22b of the second endoscope 22 is formed to have two curved portions 22b' and 22b" which can be bent in four directions (for example, up, down, left, right) connected thereto. In addition, to this endoscope 22 are provided two operation portions 22c' and 22c" corresponding to the respective curved portions 22b' and 22b". The curved portion 22b" on the end side of the insertion portion 22a is operated by the operation portion 22c", and the curved portion 22b' on the rear end side is operated by the operation portion 22c' on the rear end side.

When the lesioned part 28 exists on the gastric mucosa in the stomach 2 on the back side, this lesioned part 28 is treated by the two flexible endoscopes 11 and 22 as follows.

At first, like the first embodiment, after confirming the position and dimensions of the lesioned part 28 in the stomach 2 by using the first endoscope 11, the gastric fistula formation tube 4 is positioned. Then, after inflating the stomach 2 through the stomach fistula formation tube 4, the first flexible endoscope 1 is orally inserted into the stomach 2, and the second flexible endoscope 22 is inserted into the stomach 2 through the inner hole of the gastric fistula formation tube 4. Then, the lesioned part 28 is reconfirmed by using the first flexible endoscope 11.

Thereafter, the curved portions 22b' and 2b" are bent in desired directions by respectively operating the operation portions 22c' and 22c" of the second flexible endoscope 22, and the lesioned part 28 is grasped and lifted up by using the grasping forceps 24. The needle-shaped scalpel 30 provided to the first endoscope 11 is used to cut the lifted-up lesioned part 28. The cut lesioned part 28 is collected by using the grasping forceps 24, and examination is carried out.

It is to be noted that the curved portions 22b' and 22b" which can be bent in four directions are provided to the curved portion 22b of the second flexible endoscope 22 in this embodiment but the present invention is not restricted to such a curved portion 22b. For example, as shown in FIG. 13, curved portions 11b' and 11b" which can be bent in four directions may be respectively provided to the curved portion 11b of the first flexible endoscope 11 and operation portions 11c' and 11c" which respectively operate the curved portions 11b' and 11b" in the main body of the endoscope 11 may be provided. Additionally, for example, as shown in FIG. 14, curved portions 11b', 11b", 22b' and 22b" which can be bent in four directions may be respectively provided to the curved portions 11b and 22b of the first and second endoscopes 11 and 22, and two operation portions 11c', 11c" and 22c' and 22c" may be provided to the main bodies of the endoscopes 11 and 22.

Further, the number of directions in which the curved portions 11b and 22b of the endoscopes 11 and 22 are formed is not restricted to four, and two directions or three directions may be adopted.

Therefore, the following can be said with respect to this embodiment. Although description has been given as to the case where the lesioned part 28 on the back side is treated in this embodiment, a desired treatment can be readily given to the lesioned part 28 in the vicinity of the abdominal cavity, where the treatment is hardly carried out, by providing a plurality of curved portions 22b' and 22b".

A 10th embodiment will now be described with reference to FIGS. 15A to 15D. This embodiment is a modification of the first embodiment, and like reference numerals denote like or corresponding parts, thereby omitting the detailed explanation.

Figure 15D:
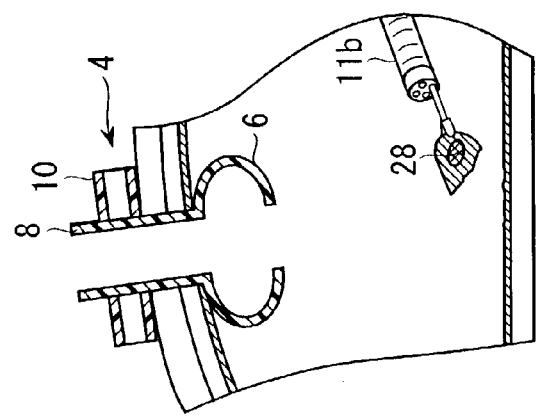
FIG. 15D is a schematic view showing that the lesioned part is collected by using the first flexible endoscope after cutting the lesioned part by using a high-frequency snare illustrated in FIGS. 15A to 15C.
Figure 15C:
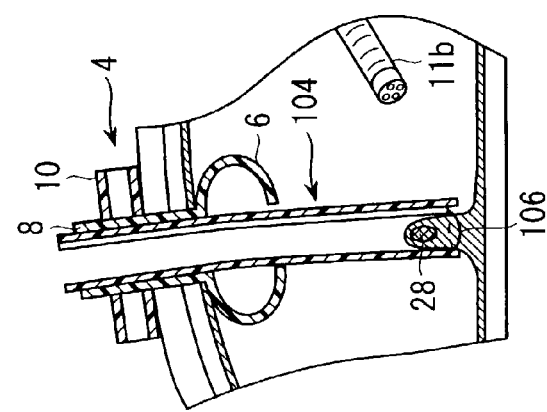
FIG. 15C is a schematic view showing a state that the lesioned part is sucked into the cover tube.
Figure 15A:
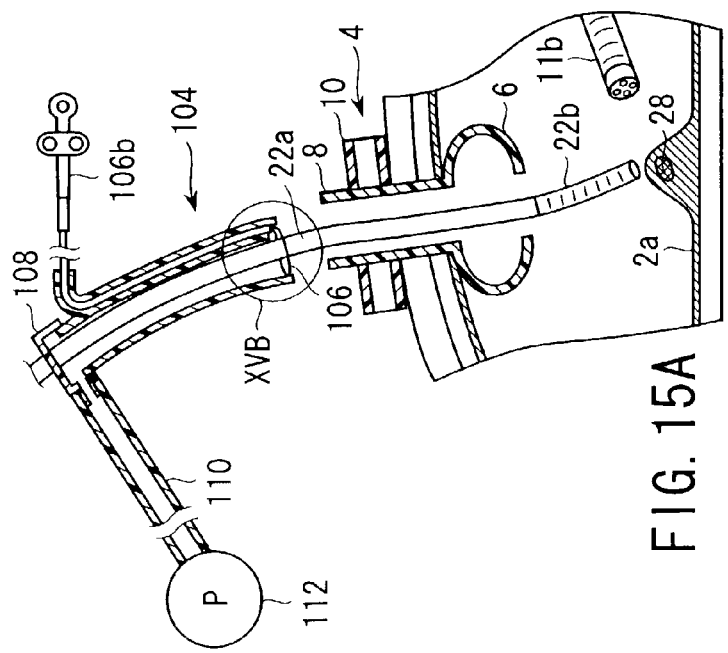
FIG. 15A is a schematic view showing a state that a cover tube is put on the second flexible endoscope according to a tenth embodiment.
Figure 15B:
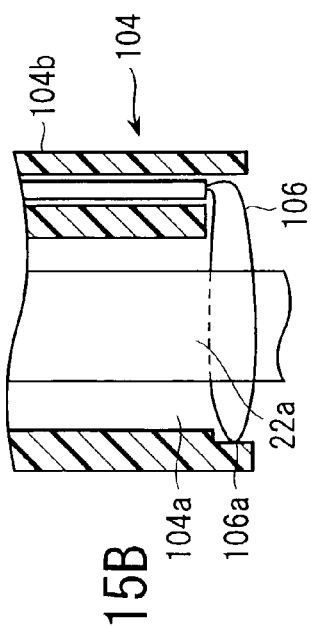
FIG. 15B is a schematic view showing a structure of an end portion of the cover tube illustrated in FIG. 15A.

As shown in FIG. 15A, in a treatment apparatus according to this embodiment, the first and second flexible endoscopes 11 and 22 are inserted into the stomach 2. In the second endoscope 22 is provided a cover tube 104 as a transparent treatment tool (insertion member) whose diameter is larger than that of the insertion portion 22a of the endoscope 22 and which has flexibility. Further, as shown in FIG. 15C, the gastric fistula formation tube 4 is formed to have a larger inside diameter than the outside diameter of the cover tube 104. As shown in FIG. 15B, a scope insertion lumen 104a and a treatment tool channel 104b are provided in the cover tube 104. A high-frequency snare 106 as a treatment tool (insertion member) is provided in the treatment tool channel 104b. Furthermore, a step is provided at the end of the cover tube 104, and a snare holding groove 106a of the high-frequency snare 106 is formed so that the high-frequency snare 106 can extend the diameter at a predetermined position.

As shown in FIG. 15A, a seal member 108 is provided at the other end portion of the cover tube 104, namely, the upper end portion of the scope insertion lumen 104a. This seal member 108 enables the insertion portion 22a of the endoscope 22 to be inserted into the scope insertion lumen 104a, and is appressed against the insertion portion 22a. Furthermore, an opening is formed on the side portion of the seal member 108. One end portion of a suction tube 110 having an aspirator 112 provided at the other end portion is connected to this opening. It is to be noted that the operation portion 106b of the high-frequency snare 106 is provided so as to protrude from the side of the cover tube 104.

When the lesioned part 28 exists on the gastric mucosa in the stomach 2 on the back side, this lesioned part 28 is treated by the two flexible endoscopes 11 and 22 as follows.

At first, for example, air is supplied into the stomach 2 through the gastric fistula formation tube 4, and the stomach 2 is inflated. Then, as shown in FIG. 15A, with the cover tube 104 being put on the second endoscope 22, the second endoscope 22 is inserted into the gastric fistula formation tube 4. The end portion of the cover tube 104 is moved closer to the lesioned part 28 while observing the lesioned part 28 by using the first and second endoscopes 11 and 22. As shown in FIG. 15C, the end portion of the cover tube 104 is appressed against the gastric mucosa 2a, and the high-frequency snare 106 is arranged at a position where it surrounds the lesioned part 28. Then, the aspirator 112 connected to the scope insertion lumen 104a in the cover tube 104 is operated to suck the lesioned part 28. In the suction state, the high-frequency snare 106 is operated and the lesioned part 28 is tied and cut out. Thereafter, as shown in FIG. 15D, the lesioned part 28 is grasped by using the grasping forceps 82 provided to the first endoscope 11 and collected, and examination is carried out.

Therefore, the following can be said with respect to this embodiment. The cover tube 104 is provided around the insertion portion 22a of the second endoscope 22, and the lesioned part 28 is upraised by using the cover tube 104. Therefore, with the lesioned part 28 being upraised in this manner, the lesioned part 28 is cut out by using the high-frequency snare 106 provided in the cover tube 10, thereby facilitating the operation.

It is to be noted that the lesioned part 28 is collected by using the first endoscope 11 in this embodiment but the lesioned part 28 may be sucked and collected by using the aspirator 112 of the cover tube 104.

An 11th embodiment will now be described with reference to FIG. 16. This embodiment is a modification of the first embodiment, and like reference numerals denote like or corresponding parts, thereby omitting the detailed explanation.

Figure 16:
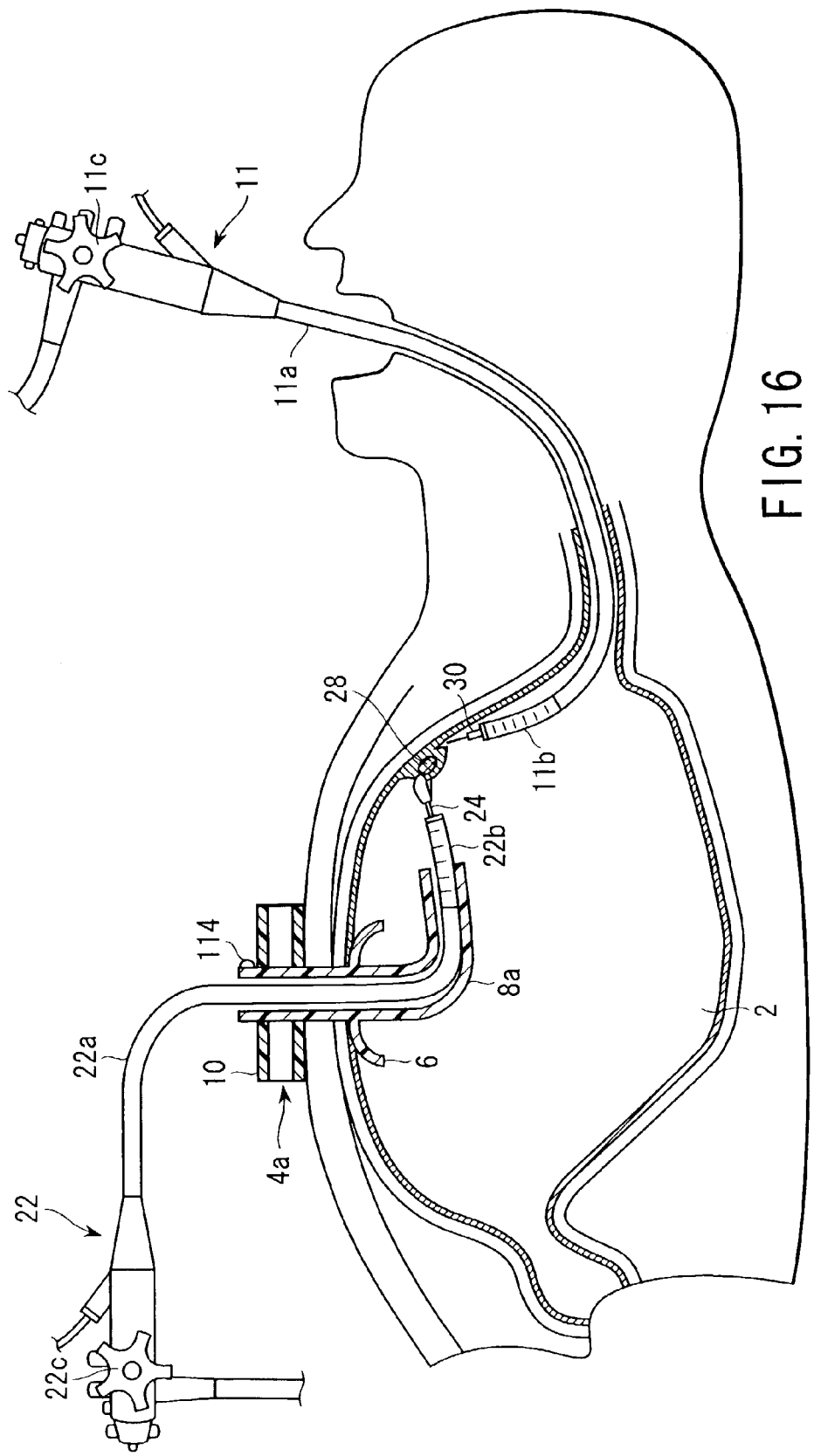
FIG. 16 is a schematic cross-sectional view showing a treatment apparatus which orally leads a first flexible endoscope into an organ, abdominally or transdermally leads a second flexible endoscope into the organ by using a curved gastric fistula formation tube in the stomach and gives a medical treatment to a lesioned part existing on the abdominal wall side by using these two flexible endoscopes according to an 11th embodiment.

As shown in FIG. 16, in a treatment apparatus according to this embodiment, the first and second flexible endoscopes 11 and 22 are inserted into the stomach 2. When inserting the second endoscope 22 into the stomach 2, it is inserted through the inner hole of the stomach fistula formation tube 4a. This gastric fistula formation tube 4a is constituted by a dome portion 6 and a curved tube 8a as a catheter piercing the dome portion 6. This curved tube 8a is substantially straight outside the body cavity and bent in an arbitrary direction in the stomach 2. Furthermore, a mark 114 is attached to the upper end portion of the curved tube 8a outside the body in the direction in which the curved tube 8a is bent. Therefore, the direction of the curved tube 8a can be readily recognized by an operator. It is to be noted that the curve shape is not restricted to the one illustrated in FIG. 16. An operator can easily form a desired shape by hot shaping and the like. In addition, it is preferable that the mark 114 consists of a marking, a notch or the like.

Since this gastric fistula formation tube 4a is positioned and kept in place like the gastric fistula formation tube 4 described in connection with the first embodiment, explanation is emitted. Additionally, when a lesioned part 28 exists on the gastric mucosa in the stomach 2 on the abdominal cavity side, the lesioned part 28 is treated by the two flexible endoscopes 11 and 22 as follows.

At first, when positioning the gastric fistula formation tube 4a, the dimensions of the lesioned part 28 are confirmed by using the first endoscope 11. Then, for example, air is supplied into the stomach 2 through the gastric fistula formation tube 4a, and the stomach 2 is inflated. Subsequently, the first flexible endoscope 11 is orally inserted into the stomach 2, and the second flexible endoscope 22 is inserted into the stomach 2 through the inner hole of the gastric fistula formation tube 4a. Then, the lesioned part 28 is reconfirmed by using the first flexible endoscope 11.

Thereafter, the location of the mark 114 is confirmed, and the insertion portion 22a of the second flexible endoscope 22 is led in the direction of the lesioned part 28 through the gastric fistula formation tube 4a. Then, the curved portion 22b is bent toward the lesioned part 28, and the lesioned part 28 is grasped by using the grasping forceps 24 and lifted up toward the central part of the stomach 2. The needle-shaped scalpel 30 provided to the first endoscope 11 is used to cut the upraised lesioned part 28. Subsequently, the cut lesioned part 28 is collected by using the grasping forceps 24, and examination is carried out.

Therefore, the following can be said with respect to this embodiment. Using the gastric fistula formation tube 4a as such a leading portion which is bent in an organ and leads the insertion portion 22a of the second endoscope 22 to a desired position can facilitate giving a medical treatment to the lesioned part 28 at a position close to the abdominal cavity. Furthermore, by providing the mark 114 at the upper end portion of the tube 8a of the gastric fistula formation tube 4a, an operator can instantaneously recognize the direction in which the insertion portion 22a of the endoscope 22 is led.

A 12th embodiment will now be described with reference to FIG. 17. This embodiment is a modification of the first embodiment, and like reference numerals denote like or corresponding parts, thereby omitting the detailed explanation.

Figure 17:
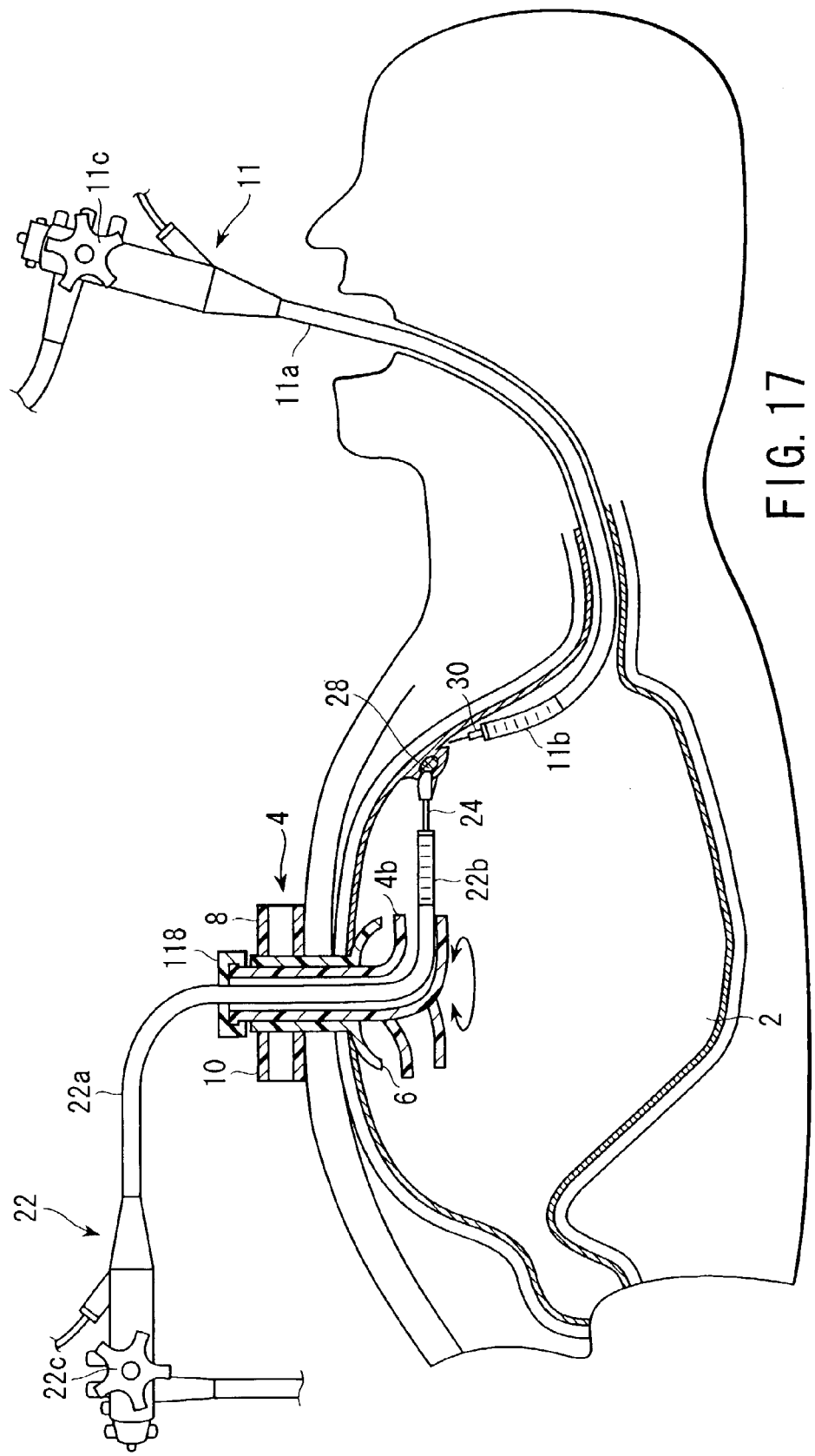
FIG. 17 is a schematic cross-sectional view showing a treatment apparatus which orally leads a first flexible endoscope into an organ, abdominally or transdermally leads a second flexible endoscope into the organ by using a curved gastric fistula formation tube in the stomach and gives a medical treatment to a lesioned part existing on the abdominal wall side by using these two flexible endoscopes according to a 12th embodiment.

As shown in FIG. 17, in a treatment apparatus according to this embodiment, the first and second flexible endoscopes 11 and 22 are inserted into the stomach 2. An insertion support tool 4b as a curved catheter is provided in the gastric fistula formation tube 4. This insertion support tool 4b can be directly inserted into the gastric fistula formation tube 4 from the outside of the body. A seal member 118 is provided at the upper end portion of the insertion support tool 4b in such a manner that the support tool 4b does not fall into the stomach 2. This insertion support tool 4b is provided so as to be capable of rotating and sliding in the gastric fistula formation tube 4. It is preferable that the insertion support tool 4b is formed of, e.g., a metal pipe or a hard resin material (elastomer). Moreover, this insertion support tool 4b may be semi-rigid and pre-formed into a desired shape before being inserted in the gastric fistula formation tube 4 by an operator. Like the 11th embodiment, a mark or a notch may be provided in the curved direction.

When the lesioned part 28 exists on the gastric mucosa in the stomach 2 on the abdominal cavity side, this lesioned part 28 is treated by the two flexible endoscopes 11 and 22 as follows.

At first, when positioning the gastric fistula formation tube 4, the dimensions of the lesioned part 28 are confirmed by using the first endoscope 11. Then, for example, air is supplied into the stomach 2 through the inner hole of the gastric fistula formation tube 4, and the stomach 2 is inflated. Subsequently, the first flexible endoscope 11 is orally inserted into the stomach 2, and the second flexible endoscope 22 is inserted into the stomach 2 through the inner hole of the insertion support tool 4b provided in the gastric formation tube 4. Then, the lesioned part 28 is reconfirmed by the first flexible endoscope 11.

Thereafter, the support tool 4b of the gastric fistula formation tube 4b is rotated around the gastric fistula formation tube 4, and the insertion portion 22a of the second flexible endoscope 22 is led in the direction of the lesioned part 28. The curved portion 22b is bent toward the lesioned part 28, and the lesioned part 28 is grasped and upraised by using the grasping forceps 24. In addition, the needle-shaped scalpel 30 provided to the first endoscope 11 is used to cut the upraised lesioned part 28. Thereafter, the cut lesioned part 28 is collected by using the grasping forceps 24, and examination is carried out.

Therefore, the following can be said with respect to this embodiment. By using the gastric fistula formation tube 4 which has such a insertion support tool 4b which is bent in an organ, the insertion support tool 4b acts as a leading portion which leads the insertion portion 22a of the second endoscope 22 to a desired position. Therefore, a medical treatment can be easily given to the lesioned part 26 at a position close to the abdominal cavity.

A 13th embodiment will now be described with reference to FIGS. 19A and 19B. This embodiment is a modification of the first embodiment, and like reference numerals denote like or corresponding parts, thereby omitting the detailed explanation.

Figure 18:
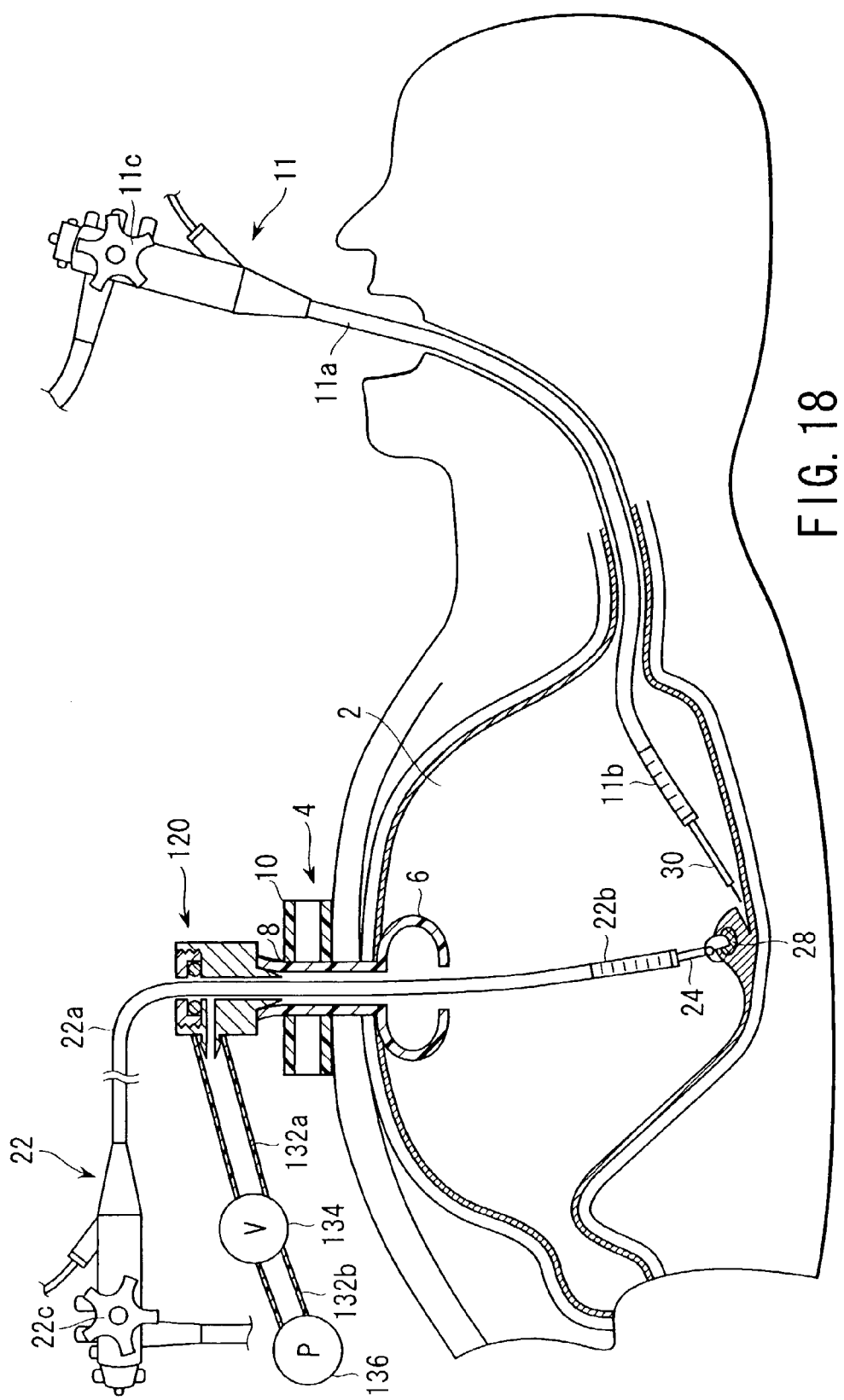
FIG. 18 is a schematic cross-sectional view showing a treatment apparatus which orally leads a first flexible endoscope into an organ, abdominally or transdermally leads a second flexible endoscope into the organ through an insertion support tool provided at the upper end of a gastric fistula formation tube and gives a medical treatment to a lesioned part by using these two flexible endoscopes according to a 13th embodiment.

As shown in FIG. 18, in a treatment apparatus according to this embodiment, the first and second flexible endoscopes 11 and 22 are inserted into the stomach 2. A fluid control device 120 for the gastric fistula formation tube 4 is provided at the other end of the tube 8 of the gastric fistula formation tube 4. This fluid control device 120 is used to smoothen insertion of the insertion portion 22a of the endoscope 22.

Figure 19A:
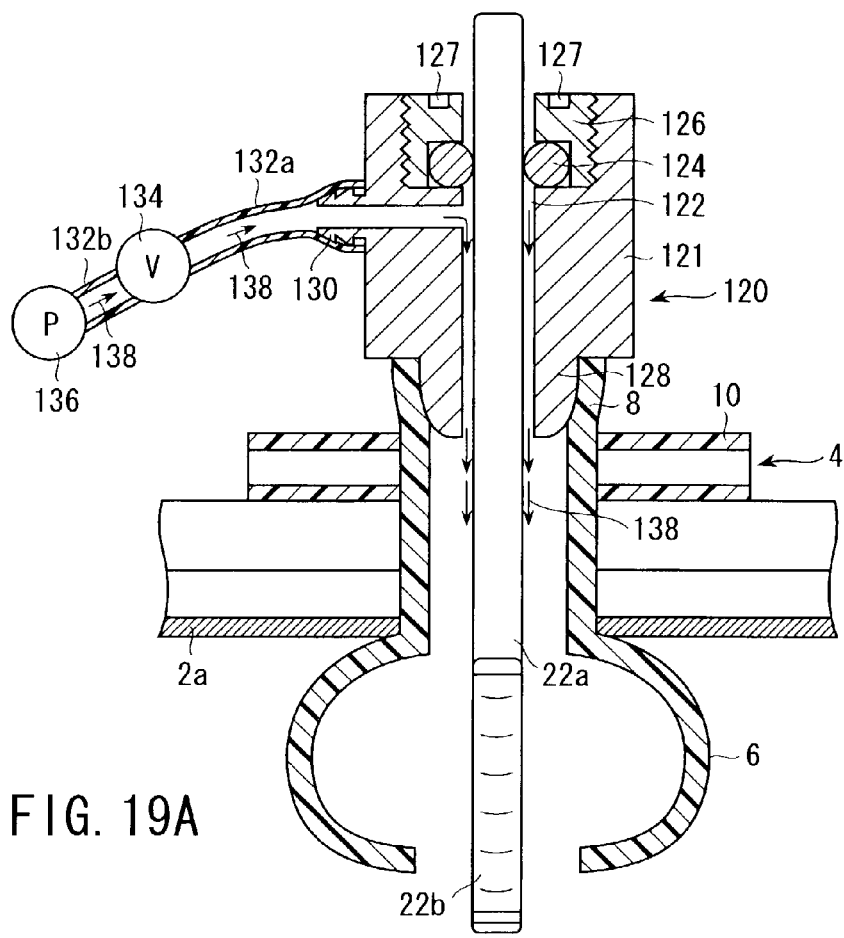
FIG. 19A is a schematic cross-sectional view showing the insertion support tool of the endoscope provided at the upper end portion of the gastric fistula formation tube illustrated in FIG. 18.

As shown in FIG. 19A, this fluid control device 120 includes a main body 121, and a through hole 122 through which the insertion portion 22a of the endoscope 22 can be inserted, is made in the main body 121. The diameter of the through hole 122 is formed slightly larger than the diameter of the insertion portion 22a of the endoscope 22 so that the insertion portion 22a can be inserted into the through hole 122. A seal member 124 consisting of, e.g., an O ring is provided in the vicinity of the upper end portion of the through hole 122. This seal member 124 is fixed from the upper end portion of the fluid control device 120 by a fixture 126. This fixture 126 is screwed to the main body 121. Additionally, this fixture 126 includes a slotted hole 127 used to attach/detach the fixture 126 to/from the insertion support tool main body 120. A connection portion 128 fitted to the upper end portion of the tube 8 of the gastric fistula formation tube 4 is formed at the lower end portion of the main body 121.

Further, an air supply mouth ring 130 as an air lead-in duct having a hole communicating with the through hole 122 is provided preferably in a direction orthogonal to the through hole 122 of the main body 121. An excessive pressure rise prevention valve (pressure control valve) 134 is provided by the air supply mouth ring 130 via an air supply hose 132a, and an air supply pump 136 is provided to the excessive pressure rise prevention valve 134 via an air supply hose 132b.

Figure 19B:
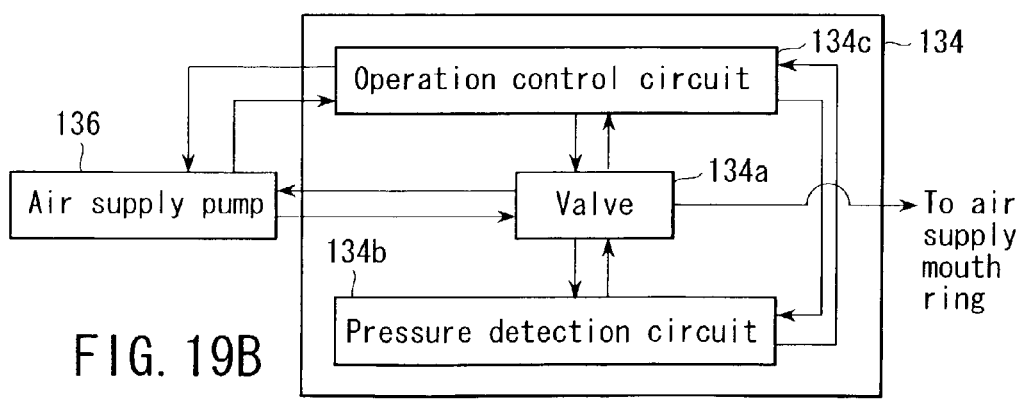
FIG. 19B is a block diagram showing structures of an excessive pressure rise prevention valve and an air supply pump illustrated in FIG. 19A.

Furthermore, as shown in FIG. 19B, the excessive pressure rise prevention valve 134 includes a valve 134*a*, a pressure detection circuit 134*b* and an operation control circuit 134*c*. The pressure detection circuit 134*b* detects the pressure in the stomach 2 and pressure of air supplied from the air supply pump 136 through the valve 134*a* at predetermined intervals of, e.g. 0.5 seconds. Moreover, the operation control circuit 134*c* controls opening/closing of the valve 134*a* and the operation of the air supply pump 136 by using the pressure detected by the pressure detection circuit 134*b*. Therefore, when the inside of the stomach 2 reaches a predetermined pressure, the operation control circuit 134*c* acts to stop the operation of the air supply pump 136 and close the valve 134*a*. When supplying air into the stomach 2, the pressure on the stomach 2 side is detected. When the inside of the stomach 2 is yet to reach a predetermined pressure, the air supply pump 136 is actuated, the valve 134*a* is opened, and air is supplied into the stomach 2. In this manner, a fluid supply mechanism is formed.

When such a fluid control device 120 is provided at the upper end portion of the tube 8 of the stomach fistula formation tube 4 and the insertion portion 22*a* of the endoscope 22 is inserted into the stomach 2 through the through hole 122 of the fluid control device 120 and caused by the sliding insertion portion 22*a*, the following effect can be obtained.

At first, air 138 is supplied from the air supply pump 136 and fed into the main body 121 of the fluid control device 120 through the air supply hose 132*b*, the excessive pressure rise prevention valve 134, the air supply hose 132*a* and the air supply mouth ring 130. The insertion portion 22*a* of the endoscope 22 is inserted into the through hole 122 while continuing air supply. Inserting the insertion portion 22*a* of the endoscope 22 supplies into the stomach 2 the air fed from the air supply pump 136. In addition, when the insertion portion 22*a* is inserted, the friction coefficient between the through hole 122 and the insertion portion 22*a* is lowered by the flow effect of the air 138 supplied between the through hole 122 of the fluid control device 120 and the insertion portion 22*a* of the endoscope 22. Therefore, the insertion portion 22*a* of the endoscope 22 is caused to smoothly slide in the through hole 122.

Incidentally, when the pressure detection mechanism 134*b* provided to the excessive pressure rise prevention valve 134 detects that the inside of the stomach 2 has reached a predetermined pressure, data indicating this is supplied to the operation control device 134*c*, the operation of the air supply pump 136 is stopped, and the valve 134*a* is closed.

Therefore, when this fluid control device 120 is used, the air 138 is supplied by the air supply pump 136 via the through hole 122 until the inside of the stomach 2 reaches a desired pressure, and the flow of the air 138 provides a smoothing effect between the through hole 122 and the insertion portion 22*a* of the endoscope 22.

It is to be noted that it is preferable that a sensor (not shown) which detects sliding of the insertion portion 22*a* of the endoscope 22 be attached to the fluid control device 120 according to this embodiment. It is preferable that sliding of this insertion portion 22*a* is detected by the sensor, the air supply pump 136 is operated, start of air supply and stop of air supply are automatically controlled and the inside of the stomach 2 is held at a desired pressure.

When the lesioned part 28 exists on the gastric mucosa in the stomach 2 on the back side, this lesioned part 28 is treated by the two flexible endoscopes 11 and 22 as follows.

As shown in FIG. 18, the fluid control device 120 is fitted to the upper end of the gastric fistula formation tube 4. Then, the first flexible endoscope 11 is orally inserted into the stomach 2. Additionally, the air supply pump 136 is operated, the insertion portion 22*a* of the second endoscope 22 is inserted into the through hole 122 of the fluid control device 120 while supplying air 138 into the fluid control device 120, and the insertion portion 22*a* is inserted into the stomach 2 through the inner hole of the gastric fistula formation tube 4. In this state, air 138 is supplied into the stomach 2, and the inflated state is obtained. Then, the lesioned part 28 is reconfirmed by using the first and second endoscopes 11 and 22.

Thereafter, after grasping the lesioned part 28 by using the grasping forceps 24 inserted into the second endoscope 22, the grasping forceps 24 is pulled to upraise the lesioned part 28. This lesioned part 28 is cut by using the needle-shaped scalpel 30. Upon completion of such a treatment, the second flexible endoscope 22 is removed from the living body while grasping the cut part, and the lesioned part 28 is collected, and examination is carried out.

Therefore, the following can be said with respect to this embodiment. The fluid control device 120 is provided to the gastric fistula formation tube 4. Therefore, the stomach 2 is controlled to be inflated so as to maintain a desired pressure therein during an operation, and insertion (sliding) of the insertion portion 22*a* of the endoscope 22 is smoothened during the operation.

Since the insertion portion 22*a* has substantially the same diameter as that of the through hole 122 so as to be capable of sliding, wobble of the insertion portion 22*a* of the endoscope 22 is minimized.

A 14th embodiment will now be described with reference to FIGS. 20 and 21. This embodiment is a modification of the first embodiment, and like reference numerals denote like or corresponding parts, thereby omitting the detailed explanation.

Figure 20:
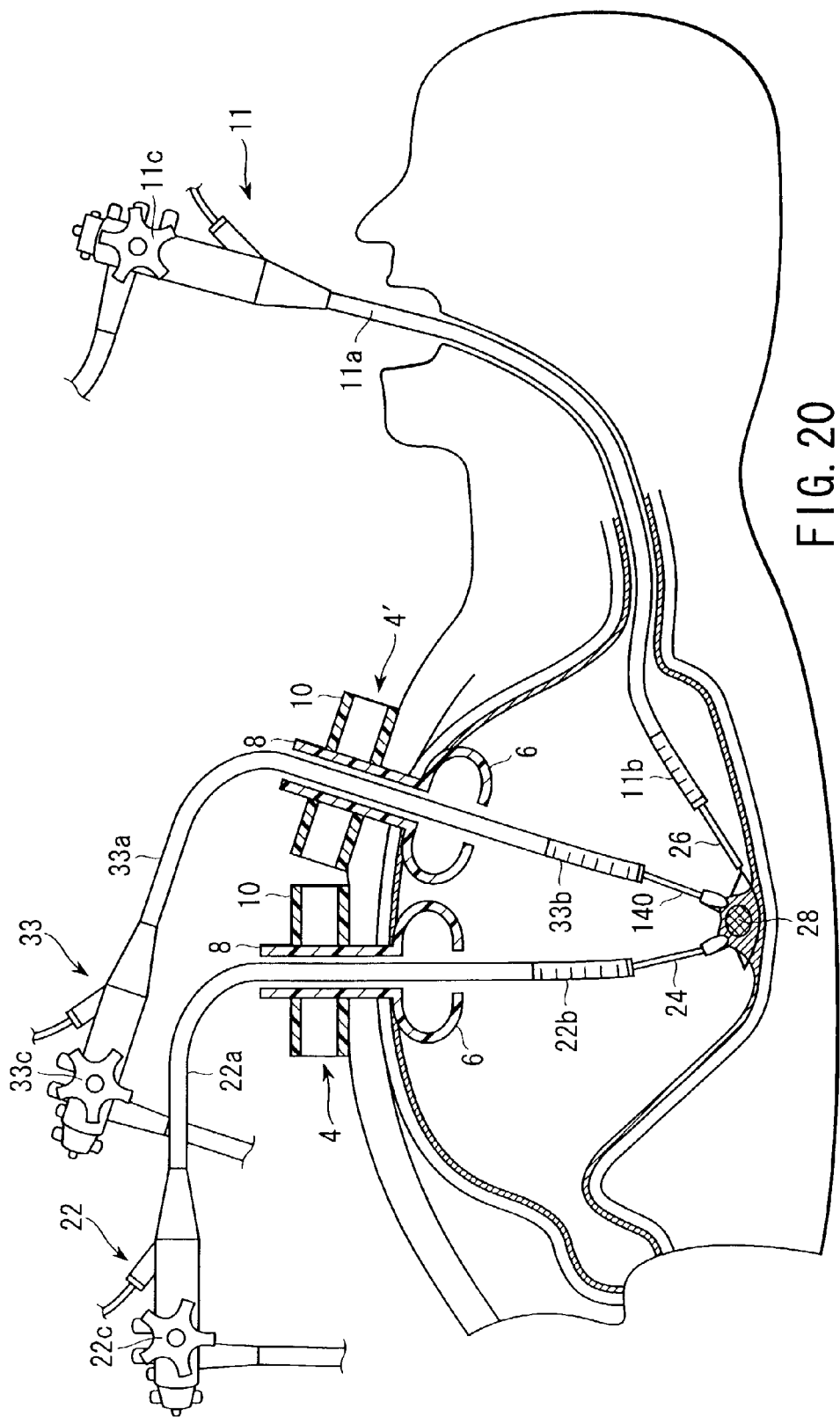
FIG. 20 is a schematic cross-sectional view which orally leads a first flexible endoscope into an organ, abdominally or transdermally leads second and third flexible endoscopes into the organ and gives a medical treatment to a lesioned part by using these three flexible endoscopes according to a 14th embodiment.
Figure 21:
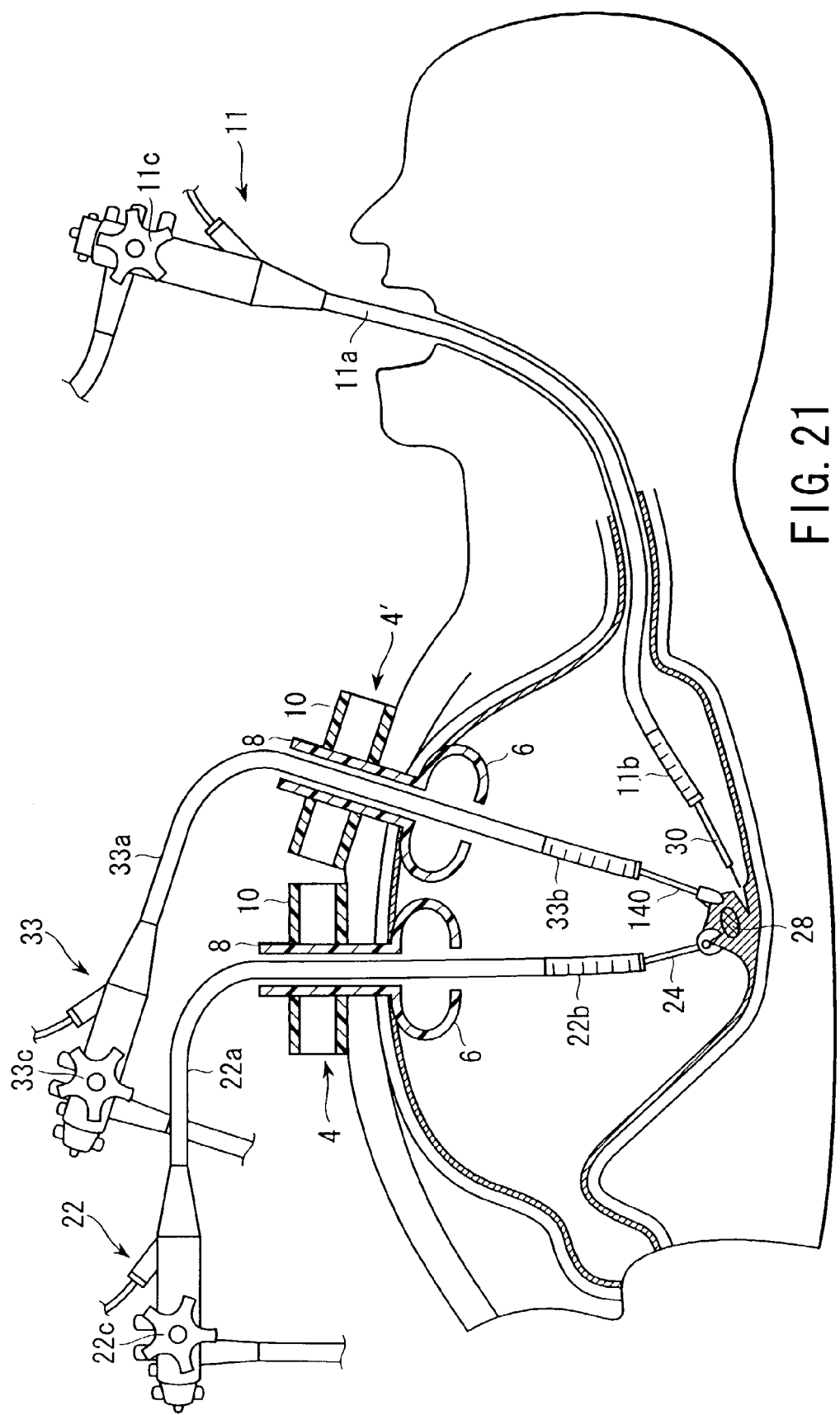
FIG. 21 is a schematic cross-sectional view showing a modification of the treatment apparatus according to the 14th embodiment.

As shown in FIG. 20, in a treatment apparatus according to this embodiment, the first and second flexible endoscopes 11 and 22 are inserted into the stomach 2. Further, in this treatment apparatus, like the gastric fistula formation tube 4 (which will be referred to as a first gastric fistula formation tube) described in connection with the first embodiment, a gastric fistula formation tube 4' (which will be referred to as a second gastric fistula formation tube) is placed and kept in the abdominal cavity as an insertion member insertion support tool.

A third flexible endoscope 33 is provided to the second gastric fistula formation tube 4'. This third flexible endoscope 33 includes an insertion portion 33*a*, a curved portion 33*b* provided at an end portion of the insertion portion 33*a*, and an operation portion 33*c* provided at a base end portion of the insertion portion 33*a*. At least a forceps channel (not shown) is provided to the insertion portion 33*a* and, for example, a grasping forceps 140 is provided to this forceps channel as a treatment tool (insertion member).

When the lesioned part 28 exists on the gastric mucosa in the stomach 2 on the back side, the lesioned part 28 is treated by the three flexible endoscopes 11, 22 and 33 as follows.

At first, as described in connection with the first embodiment, the first and second gastric fistula formation tubes 4 and 4' are positioned. At this moment, the dimensions of the lesioned part 28 are confirmed by using the first endoscope 11. For example, air is supplied into the stomach 2 through the inner hole of the first gastric fistula formation tube 4, and the stomach 2 is inflated. The first flexible endoscope 11 is orally inserted into the stomach 2. A high-frequency snare 26 is arranged in one channel of the insertion portion 11a of the endoscope 11. The second and third flexible endoscopes 22 and 23 are respectively inserted into the stomach 2 through inner holes of the gastric fistula formation tubes 4 and 4'. Furthermore, the grasping forcipes 24 and 140 are respectively inserted into one channel of each of the insertion portions 22a and 33a of these endoscopes 22 and 33. Then, the lesioned part 28 is reconfirmed by using the first to third endoscopes 11, 22 and 33.

Thereafter, the high-frequency snare 26 inserted into the first endoscope 11 is arranged around the lesioned part 28. After grasping the lesioned part 28 by using the grasping forcipes 24 and 140 inserted into the second and third endoscopes 22 and 33, the grasping forcipes 24 and 140 are pulled to upraise the lesioned part 28. A high-frequency current is passed through the previously arranged high-frequency snare 26, and the upraised lesioned portion 28 is cut. Upon completion of such a treatment, the second flexible endoscope 22 and the third flexible endoscope 33 are removed from the living body while grasping the cut part by, e.g., the grasping forcipes 24 of the second flexible endoscope 22, the lesioned part 28 is collected, and examination is carried out.

It is to be noted that description has been given as to the case where the lesioned part 28 is cut by using the high-frequency snare 26 in this embodiment, but the cutting treatment tool is not restricted to a high-frequency snare 26. For example, the lesioned part 28 may be cut by using a needle-shaped scalpel 30 shown in FIG. 21. By using this needle-shaped scalpel 30, a larger cutting range can be obtained as compared with the case where the lesioned part 28 is cut by using the high-frequency snare 26 illustrated in FIG. 20.

Furthermore, the third endoscope 33 does not have to be flexible, and it may be a rigid endoscope. The observation optical system may be removed from at least one of the insertion portion 22a and 33a of the second and third endoscopes 22 and 33.

Therefore, the following can be said with respect to this embodiment. Since the operability of the treatment apparatus is improved by using the three flexible endoscopes 11, 22 and 33, the lesioned part 28 existing on the mucosa in the stomach 2 can be assuredly cut. Thus, the lesioned part 28 is no longer left behind, and the possibility of reoccurrence can be suppressed.

In particular, since the lesioned part 28 is grasped by using the two endoscopes 22 and 33, the treatment can be further securely carried out. Moreover, since a cutting treatment tool such as the high-frequency snare 26 or the needle-shaped scalpel 30 is selected and used in accordance with a dimension of the lesioned part 28, the technique can be further assuredly carried out.

A 15th embodiment will now be described with reference to FIG. 22. This embodiment is a modification of the 14th embodiment, and like reference numerals denote like or corresponding parts, thereby omitting the detailed explanation.

Figure 22:
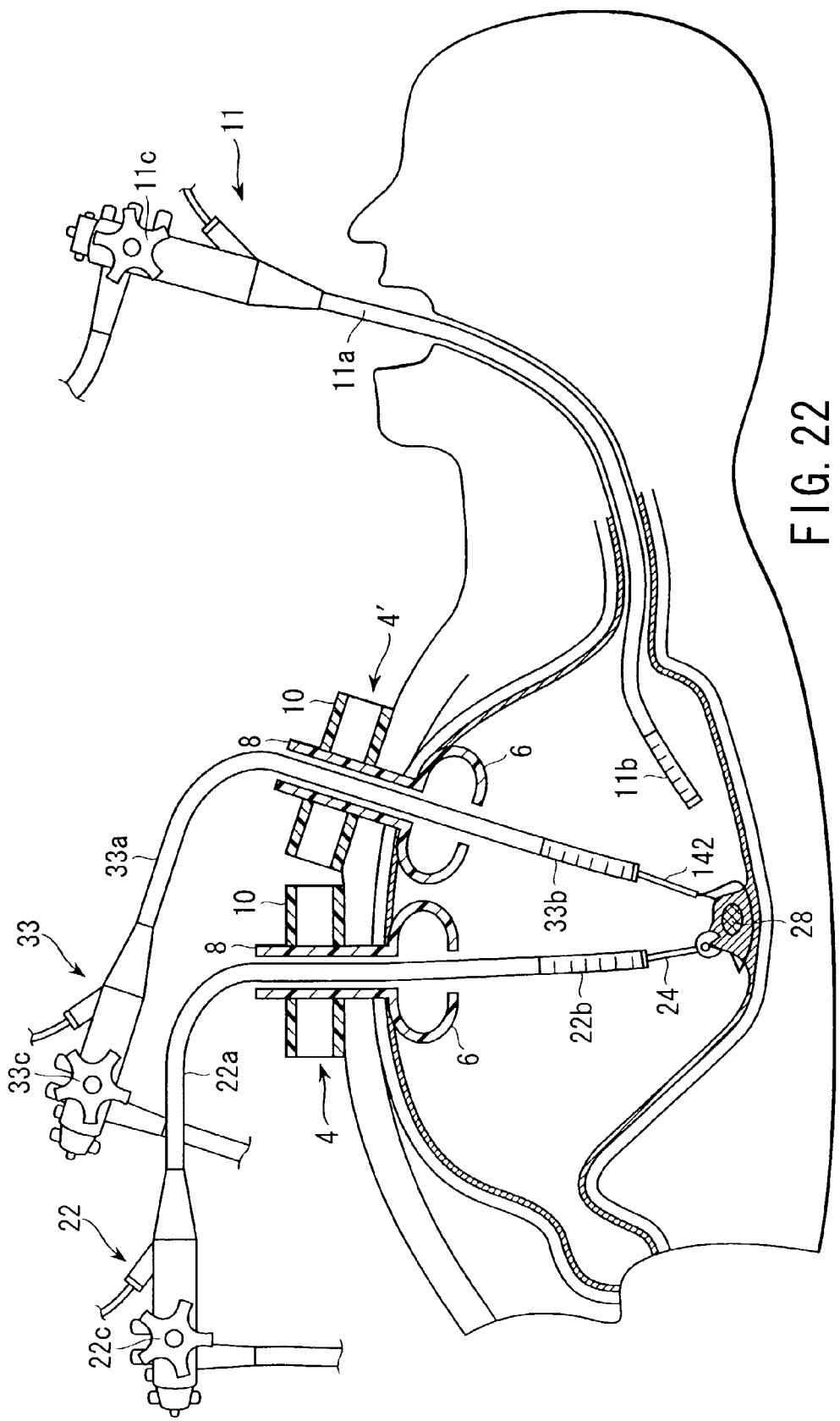
FIG. 22 is a schematic cross-sectional view showing a treatment apparatus which orally leads a first flexible endoscope into an organ, abdominally or transdermally leads second and third flexible endoscopes into the organ and gives a medical treatment to a lesioned part by using these three flexible endoscopes according to a 15th embodiment.

As shown in FIG. 22, in a treatment apparatus according to this embodiment, the first to third flexible endoscopes 11, 22 and 33 are inserted into the stomach 2. For example, a high-frequency snare 142 is provided as a treatment tool (insertion member) to a forceps channel provided to the insertion portion 33a of the third flexible endoscope 33.

When the lesioned part 28 exists on the gastric mucosa in the stomach 2 on the back side, this lesioned part 28 is treated by these three flexible endoscopes 11, 22 and 33 as follows.

At first, when positioning the first and second gastric fistula formation tubes 4 and 4', the dimensions of the lesioned part 28 are confirmed by using the first endoscope 11. For example, air is supplied into the stomach 2 through the first gastric fistula formation tube 4, and the stomach 2 is inflated. The first flexible endoscope 11 is orally inserted into the stomach 2. The second and third flexible endoscopes 22 and 33 are respectively inserted into the stomach 2 through inner holes of the gastric fistula formation tubes 4 and 4'. The grasping forceps 24 is inserted into one channel of the insertion portion 22a of the second flexible endoscope 22. The high-frequency snare 142 is inserted into one channel of the insertion portion 33a of the third flexible endoscope 33. Then, the lesioned part 28 is reconfirmed by using the first to third endoscopes 11, 22 and 33.

Thereafter, the high-frequency snare 142 inserted into the third endoscope 33 is arranged around the lesioned part 28 while performing observation of the curved portions 22b and 33b of the second and third flexible endoscopes 22 and 33 or the grasping forceps 24 and the high-frequency snare 142 arranged at the insertion portions 22a and 33a by using the first flexible endoscope 11. After grasping the lesioned part 28 by using the grasping forceps 24 inserted into the second endoscope 22, the grasping forceps 24 is pulled and the lesioned part 28 is lifted up. A high-frequency current is passed through the previously arranged high-frequency snare 142, and the upraised lesioned part 28 is cut. Upon completion of such a treatment, the second flexible endoscope 22 is removed from the living body while grasping the cut part by using the grasping forceps of the second flexible endoscope 22, the lesioned part 28 is collected, and examination is carried out.

Therefore, the following can be said with respect to this embodiment. Since a medical treatment is given to the lesioned part 28 by using the second and third endoscopes 22 and 33 while confirming the operation of the second and third endoscopes 22 and 33 by using the first endoscope 11, the technique can be further assuredly carried out.

A 16th embodiment will now be described with reference to FIG. 23. This embodiment is a modification of the 14th embodiment, and like reference numerals denote like or corresponding parts, thereby omitting the detailed explanation.

Figure 23:
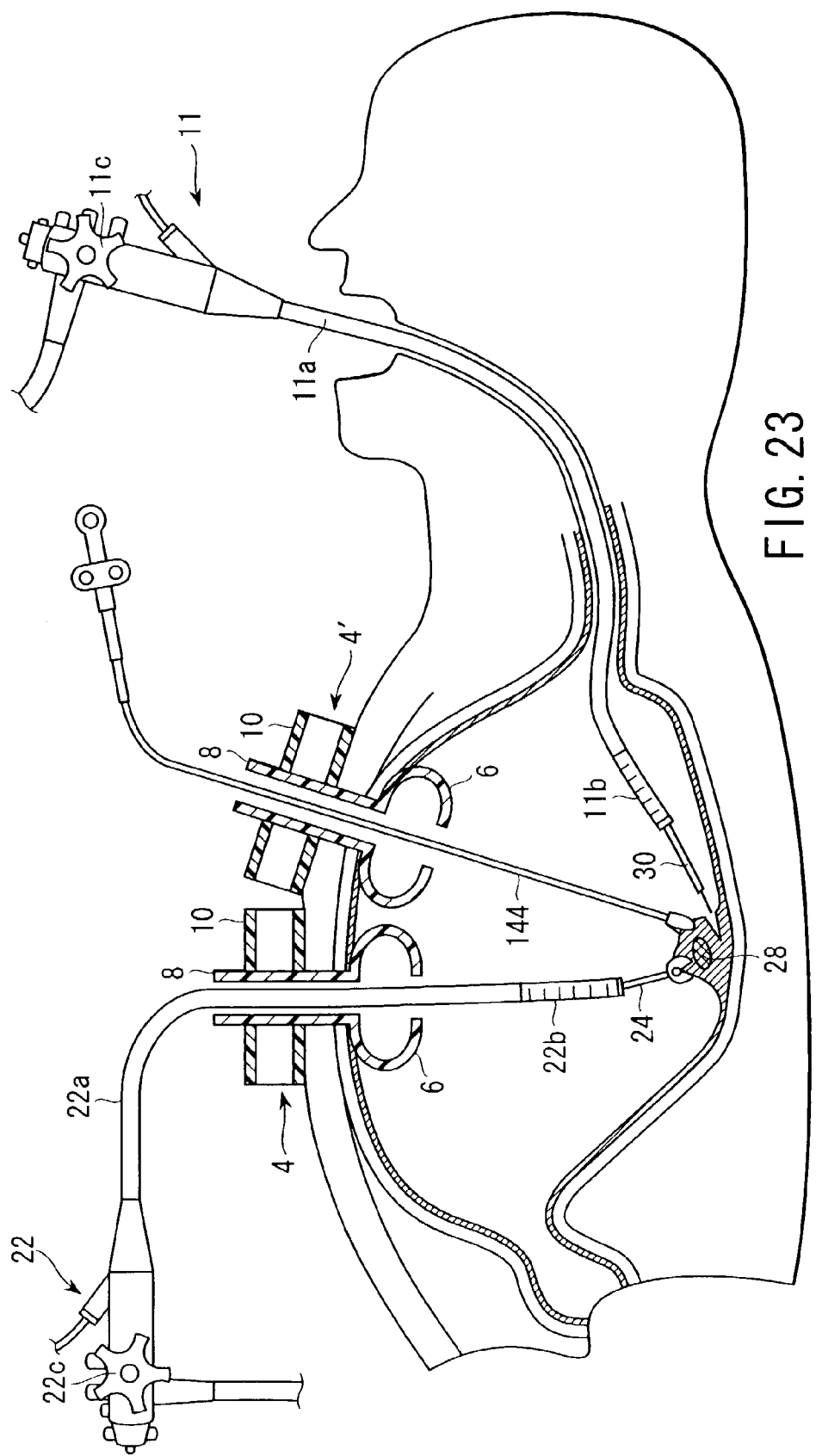
FIG. 23 is a schematic cross-sectional view showing a treatment apparatus which orally leads a first flexible endoscope into an organ, abdominally or transdermally leads a second flexible endoscope into the organ, abdominally or transdermally leads a treatment tool into the organ from another abdominal wall, and gives a medical treatment to a lesioned part by using these two flexible endoscopes and one treatment tool according to a 16th embodiment.

As shown in FIG. 23, in a treatment apparatus according to this embodiment, the first and second flexible endoscopes 11 and 22 are inserted into the stomach 2. Further, for example, a grasping forceps 144 as a treatment tool (insertion member) having flexibility is inserted into the stomach 2 through the second gastric fistula formation tube 4'.

When the lesioned part 28 exists on the gastric mucosa in the stomach 2 on the back side, the lesioned part 28 is treated by these two flexible endoscopes 11 and 22 and the grasping forceps 144 as follows.

At first, when positioning the first and second gastric fistula formation tubes 4 and 4', the first endoscope 11 is used to confirm the dimensions of the lesioned part 28. For example, air is supplied into the stomach 2 through the first gastric fistula formation tube 4, and the stomach 2 is inflated. The first flexible endoscope 11 is orally inserted into the stomach 2. For example, a needle-shaped scalpel 30 is arranged in one channel of the insertion portion 11a of the endoscope 11. The second flexible endoscope 22 is inserted into the stomach 2 through the inner hole of the first gastric fistula formation tube 4. The grasping forceps 24 is inserted into one channel of the insertion portion 22a of this endoscope 22. The grasping forceps 144 is abdominally or transdermally inserted into the stomach 2 through the second gastric fistula formation tube 4'. A part in the vicinity of the end portion of the grasping forceps 144 is grasped by the grasping forceps 24 provided to the second endoscope 22 and led to a desired position. Then, the lesioned part 28 is reconfirmed by using the first and second endoscopes 11 and 22.

Subsequently, after grasping the lesioned part 28 by using the grasping forceps 24 provided to the second endoscope 22 and the grasping forceps 144 provided to the second gastric fistula formation tube 4', the grasping forcipes 24 and 144 are pulled to lift up the lesioned part 28 so that the lesioned part 28 is upraised. The upraised lesioned part 28 is cut by using the needle-shaped scalpel 30. Upon completion of such a treatment, the grasping forceps 144 and the second flexible endoscope 22 are removed from the living body while grasping the cut portion by, e.g., the grasping forceps 144, the lesioned part 28 is collected, and examination is carried out.

It is to be noted that description has been given as to the case where a treatment is given by inserting the grasping forceps 144 having flexibility into the second gastric fistula formation tube 4' in this embodiment, but a rigid treatment tool, such a rigid grasping forceps, may be used. In addition, the present invention is not restricted to the grasping forceps 144, and a high-frequency snare or a needle-shaped scalpel may be provided instead.

Therefore, the following can be said with respect to this embodiment. In the case of inserting the grasping forceps 144 into the stomach 2, it does not have to be inserted through the forceps channel or the like of the second flexible endoscope 22, and hence there is used a treatment tool which is hard to be inserted into the forceps channel of the endoscope 22 such as a treatment tool with a large diameter or a treatment tool with a large end.

Figure 24A:
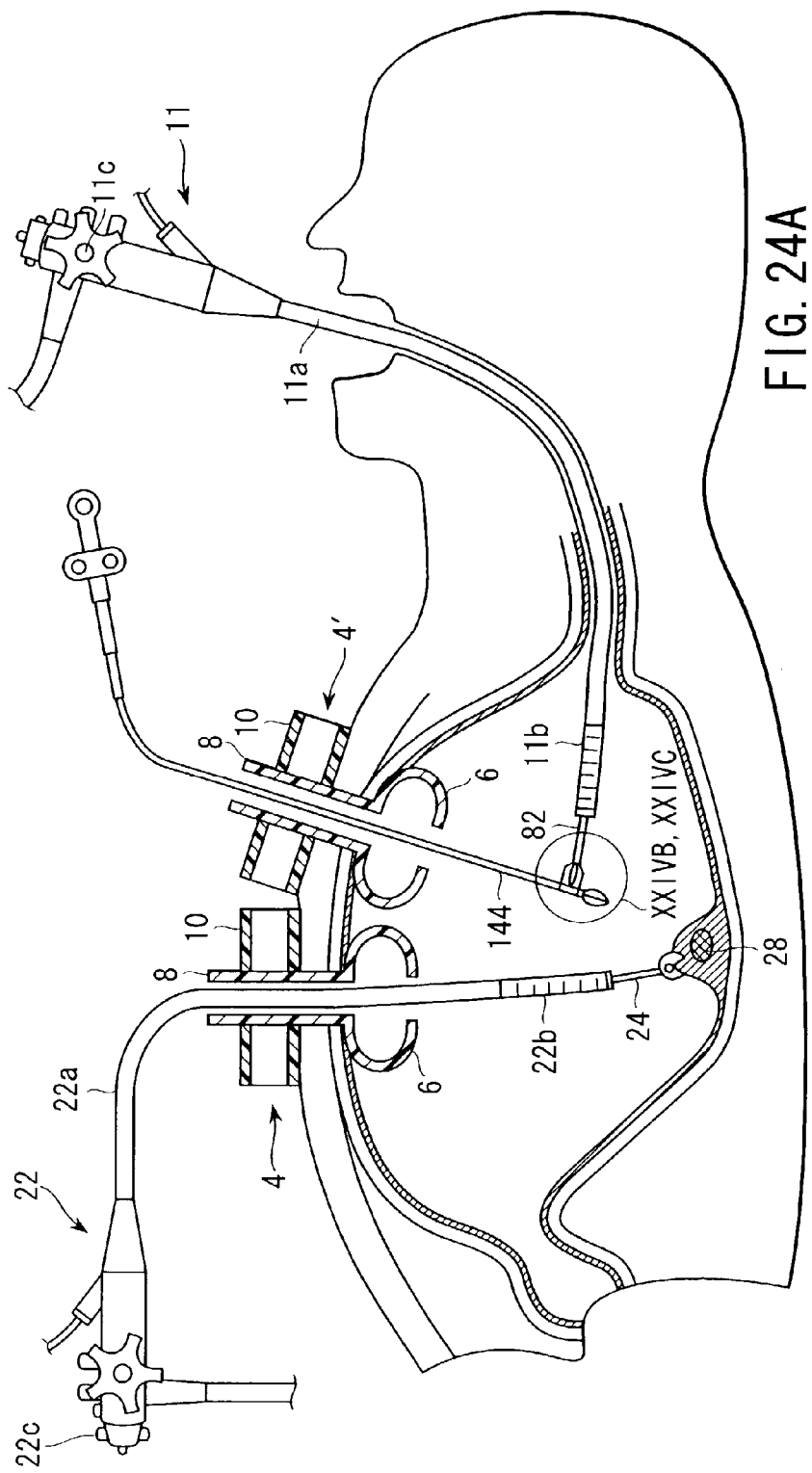
FIG. 24A is a schematic cross-sectional view showing a treatment apparatus which grasps an end portion of a treatment tool abdominally or transdermally led into an organ by using a first flexible endoscope orally led into the organ, and gives a medical treatment in the organ in cooperation with a second flexible endoscope abdominally or transdermally led into the organ according to a 17th embodiment.

A 17th embodiment will now be described with reference to FIGS. 24A to 24C, this embodiment is a modification of the 16th embodiment, and like reference numerals denote like or corresponding parts, thereby omitting the detailed explanation.

Figure 24C:
FIG. 24C is a schematic view showing that the end portion of the above-described treatment tool has a flange member.
Figure 24B:
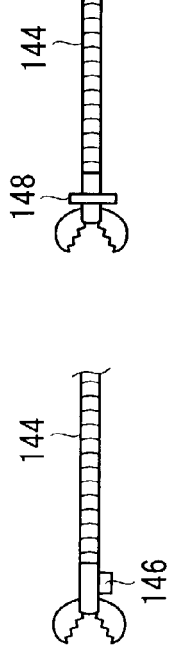
FIG. 24B is a schematic view showing that an end portion of the above-described treatment tool has a holding portion.

As shown in FIG. 24, in a treatment apparatus according to this embodiment, the first and second flexible endoscopes 11 and 22 are inserted into the stomach 2. Further, in this treatment apparatus, a grasping forceps 144 having flexibility is provided to the second gastric fistula formation tube 4'. As shown in FIG. 24B, this grasping forceps 144 has a plate type tab 146 which extends in a longitudinal direction provided in the vicinity of the end of the insertion portion 144a.

When the lesioned part 28 exists on the gastric mucosa in the stomach 2 on the back side, this lesioned part 28 is treated by the two flexible endoscopes 11 and 22 and the grasping forceps 144 as follows.

At first, when positioning the first and second gastric fistula formation tubes 4 and 4', the dimensions of the lesioned part 28 are confirmed by using the first endoscope 11. For example, air is supplied into the stomach 2 through the first gastric fistula formation tube 4, and the stomach 2 is inflated. The first flexible endoscope 11 is orally inserted into the stomach 2. For example, a grasping forceps 82 is arranged in one channel of the insertion portion 11a of the endoscope 11. The second flexible endoscope 22 is inserted into the stomach 2 through the inner hole of the first gastric fistula formation tube 4. The grasping forceps 24 is inserted into one channel of the insertion portion 22a of the endoscope 22. Furthermore, the grasping forceps 144 is inserted into the stomach 2 through the inner hole of the second gastric fistula formation tube 4'. The tab 146 as a grasping portion provided in the vicinity of the end portion of the grasping forceps 144 is grasped by the grasping forceps 82 provided to the first endoscope 11 and led to a desired position. Then, the lesioned part 28 is reconfirmed by the first and second endoscopes 11 and 22.

Then, after grasping this lesioned part 28 by using the grasping forceps 24 provided to the second endoscope 22 and the grasping forceps 144 provided to the second gastric fistula formation tube 41, the grasping forcipes 24 and 144 are pulled to lift up the lesioned part 28 so that the lesioned part 28 is upraised. For example, a non-illustrated needle-shaped scalpel is provided to the first endoscope 11, and the upraised lesioned part 28 is cut by using this needle-shaped scalpel. Upon completion of such a treatment, the grasping forceps 144 and the second flexible endoscope 22 are removed from the living body while grasping the cut part by using, e.g., the grasping forceps 144, the lesioned part 28 is collected, and examination is performed.

It is to be noted that description has been given as to the case where the plate type tab 146 is provided in the vicinity of the end portion of the grasping forceps 144 in this embodiment but the present invention is not restricted to such a tab 146 and, for example, as shown in FIG. 24C, a circular flange portion 148 may be provided in the vicinity of the end portion of the grasping forceps 144.

Therefore, the following can be said with respect to this embodiment. When inserting the grasping forceps 144 into the stomach 2, since it does not have to be inserted through the forceps channel of the flexible endoscope, a large treatment tool is used. Moving the grasping forceps 114 to the lesioned part 28 is facilitated.

An 18th embodiment will now be described with reference to FIGS. 25A and 25B. This embodiment is a modification of the 16th embodiment, and like reference numerals denote like or corresponding parts, thereby omitting the detailed explanation.

Figures 25A, 25B:
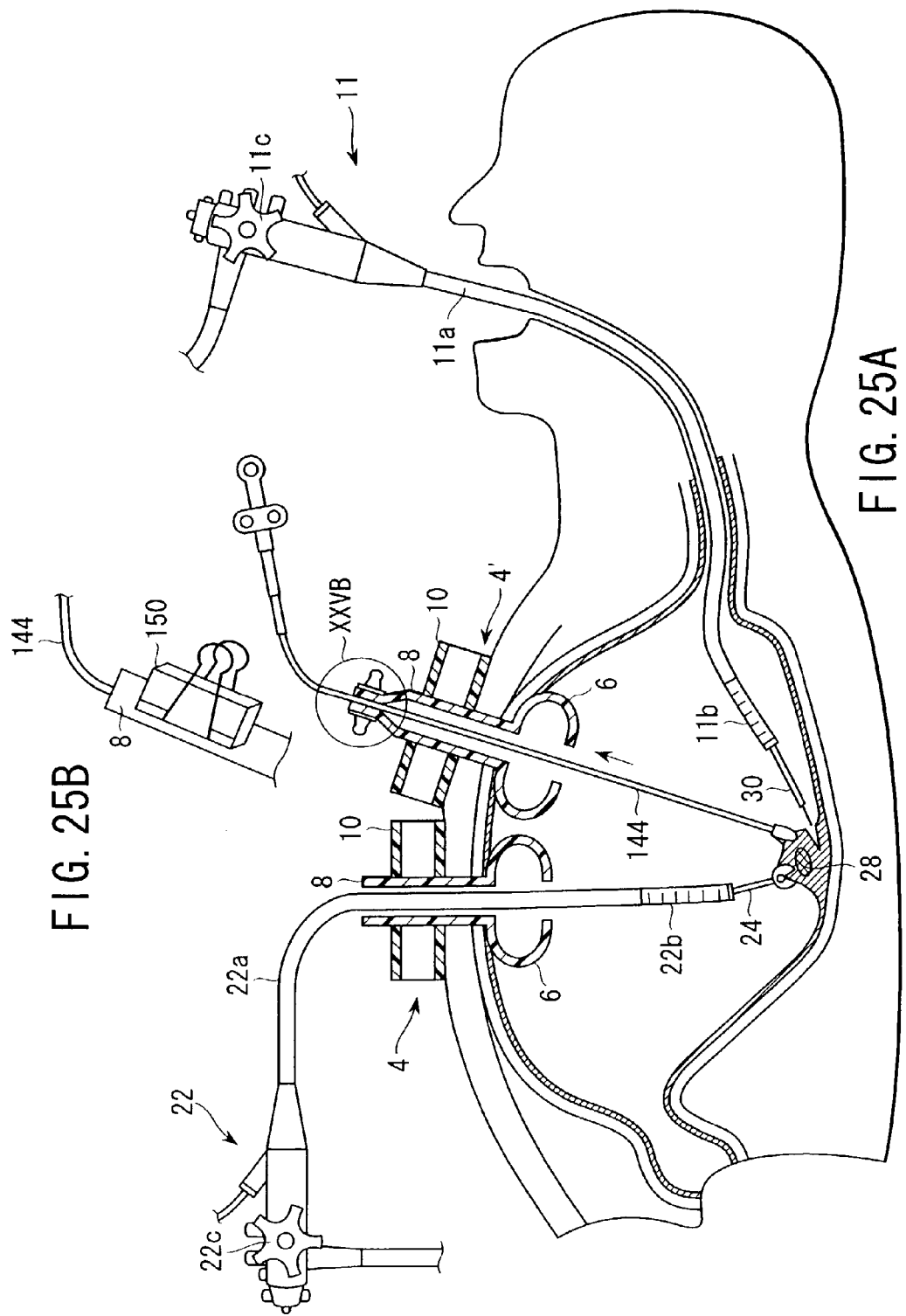
FIG. 25A is a schematic cross-sectional view showing a treatment apparatus which orally leads a first flexible endoscope into an organ, abdominally or transdermally leads a second flexible endoscope into the organ, abdominally or transdermally leads a treatment tool into the organ from another abdominal wall, and can maintain a state that a lesioned part is grasped and lifted up by using the treatment tool according to an 18th embodiment.
FIG. 25B is a schematic view showing a clip provided at the upper end portion of the gastric fistula formation tube in order to maintain the state illustrated in FIG. 25A.

As shown in FIG. 25A, in a treatment apparatus according to this embodiment, the first and second flexible endoscopes 11 and 22 are inserted into the stomach 2. Moreover, in this treatment apparatus, a grasping forceps 144 having flexibility is provided to the second gastric fistula formation tube 4'.

When the lesioned part 28 exists on the gastric mucosa in the stomach 2 on the back side, this lesioned part 28 is treated by these two flexible endoscopes 11 and 22 and the grasping forceps 144 as follows.

At first, when positioning the first and second gastric fistula formation tubes 4 and 4', the dimensions of the lesioned part 28 are confirmed by using the first endoscope 11. For example, air is supplied into the stomach 2 through the inner hole of the first gastric fistula formation tube 4, and the stomach 2 is inflated. The first flexible endoscope 11 is orally inserted into the stomach 2. For example, a needle-shaped scalpel 30 is arranged in one channel of the insertion portion 11a of the endoscope 11. The second flexible endoscope 22 is inserted into the stomach 2 through the inner hole of the first gastric fistula formation tube 4. The grasping forceps 24 is inserted into one channel of the insertion portion 22a of this endoscope 22. The grasping forceps 144 is inserted into the stomach 2 through the inner hole of the second gastric fistula formation tube 4'. A part in the vicinity of the end portion of this grasping forceps 144 is grasped by the grasping forceps 24 provided to the second endoscope 22 and led to a desired position. Then, the lesioned part 28 is reconfirmed by using the first and second endoscopes 11 and 22.

Subsequently, after grasping the lesioned part 28 by using the grasping forceps 24 provided to the second endoscope 22 and the grasping forceps 144 provided to the second gastric fistula formation tube 4', the grasping forcipes 24 and 144 are pulled to lift up the lesioned part 28 so that the lesioned part is upraised. Then, in this state, the upper end portion of the tube 8 of the second gastric fistula formation tube 4' is fastened by a clip 150 as shown in FIG. 25B. The upraised lesioned part 28 is cut by using the needle-shaped scalpel 30. Upon completion of such a treatment, the grasping forceps 144 and the second flexible endoscope 22 are removed from the living body while grasping the cut part by using, e.g., the grasping forceps 144, the lesioned part 28 is collected, and examination is carried out.

It is to be noted that the grasping forceps 144 described in connection with this embodiment may be, e.g., a rigid sheath which is bent and formed into a desired shape in advance. It may be a treatment tool which is semi-rigid and can be pre-formed into a desired shape.

Therefore, the following can be said with respect to this embodiment. With the lesioned part 28 being upraised by using the grasping forceps 144, the grasping forceps 144 is kept at a desired position. Therefore, a technique to cut off the lesioned part 28 can be operated by manipulating only the first and second endoscopes 11 and 22, thereby improving the operability.

A 19th embodiment will now be described with reference to FIGS. 26A and 26B. This embodiment is a modification of the seventh and 16th embodiments, and like reference numerals denote like or corresponding parts, thereby omitting the detailed explanation.

Figures 26A, 26B:
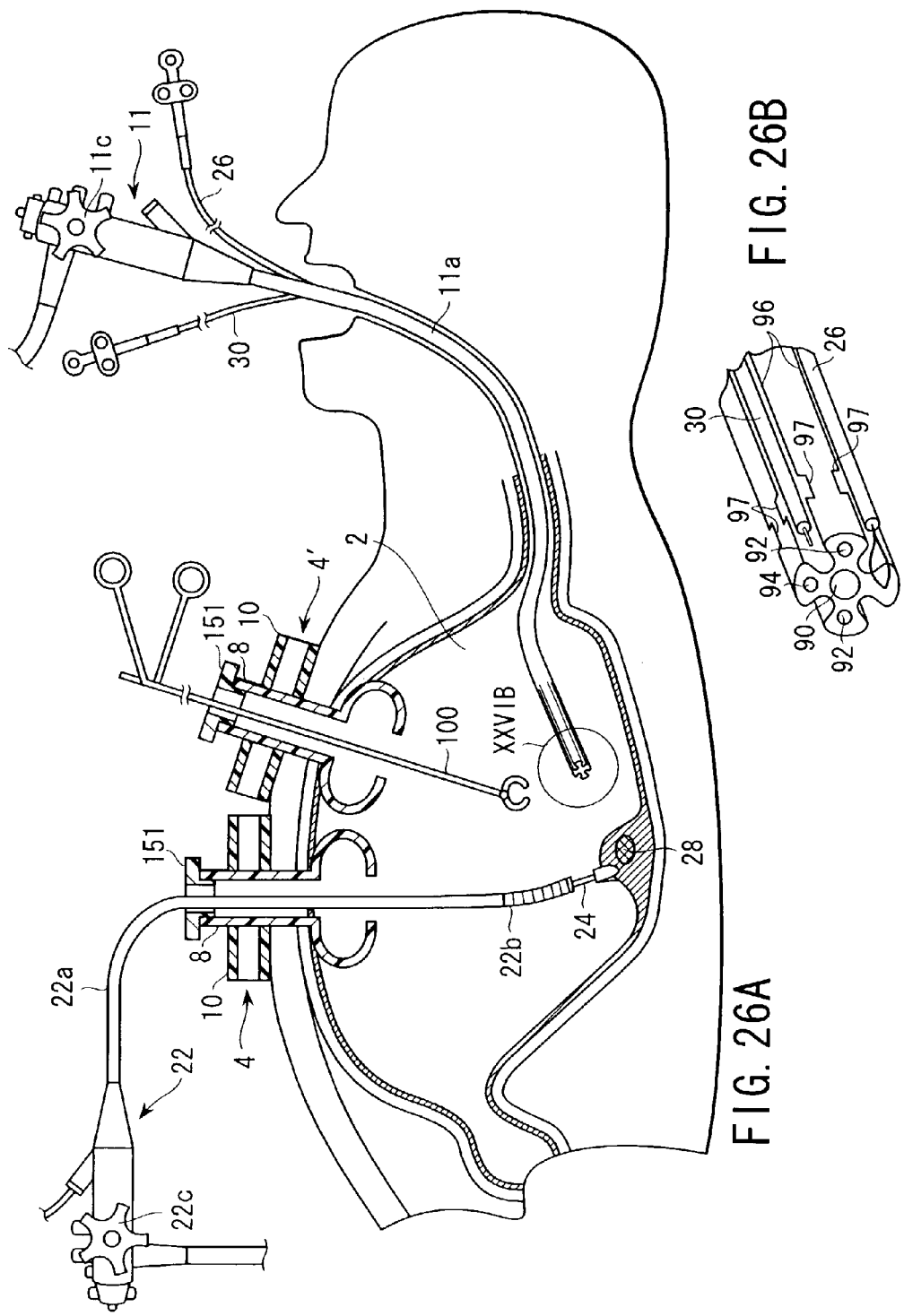
FIG. 26A is a schematic cross-sectional view showing a treatment apparatus which orally leads a first flexible endoscope into an organ, abdominally or transdermally leads a second flexible endoscope into the organ, abdominally or transdermally leads a treatment tool from another abdominal wall, and gives a medical treatment to a lesioned part according to a 19th embodiment.
FIG. 26B is a schematic view showing an end portion of the insertion portion of the first flexible endoscope.

As shown in FIG. 26A, in a treatment apparatus according to this embodiment, the first and second flexible endoscopes 11 and 22 are inserted into the stomach 2. The rigid grasping forceps 100 is inserted into the stomach 2 through the inner hole of the gastric fistula formation tube 4'.

In addition, as shown in FIG. 26B, an object lens 90 is provided at the central part of the insertion portion 11a of the first endoscope 11. A pair of light guides 92 are provided on the sides of the object lens 90. An air supply/water supply nozzle 94 is provided to this insertion portion 11a. Treatment tool guide grooves 96 are respectively provided between the light guides 92 and the air supply/water supply nozzle 94. These treatment tool guide grooves 96 are also provided at positions symmetrical with the object lens 90 at the center. For example, a high-frequency snare 26 or a needle-shaped scalpel 30 is provided in the treatment tool guide grooves 96.

When the lesioned part 28 exists on the gastric mucosa in the stomach 2 on the back side, this lesioned part 28 is treated by the two flexible endoscopes 11 and 22 in the same way as that described in the seventh embodiment.

Therefore, the following can be said with respect to this embodiment. By providing the treatment tool guide grooves 96 along the insertion portion 11a of the first flexible endoscope 11 and arranging some treatment tools in these treatment tool guide grooves 96, the treatment tool is selected and used in accordance with the dimensions of the lesioned part 28.

A 20th embodiment will now be described with reference to FIGS. 27A and 27B. This embodiment is a modification of the eighth and 16th embodiments, and like reference numerals denote like or corresponding parts, thereby omitting the detailed explanation.

Figures 27A, 27B:
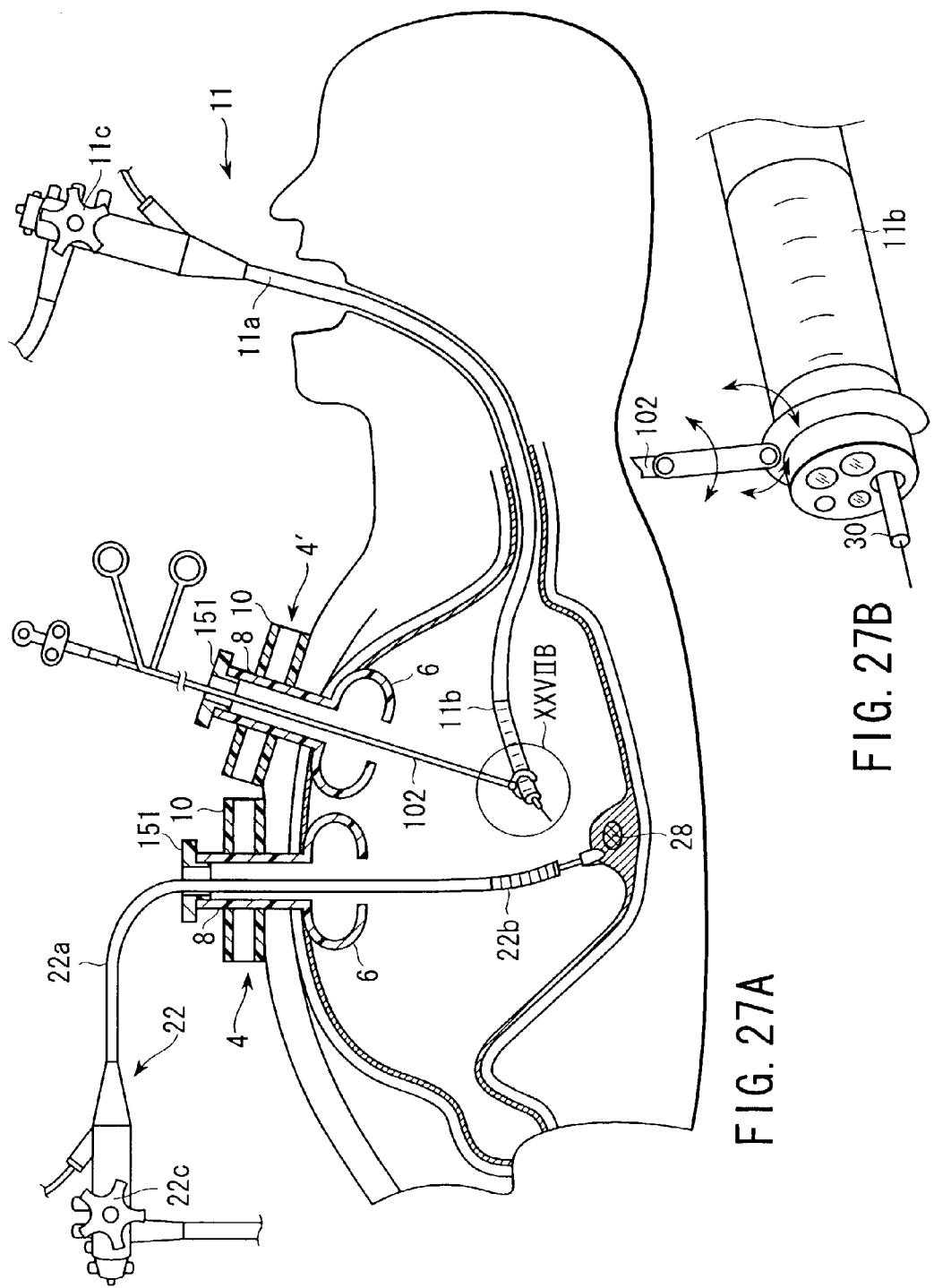
FIG. 27A is a schematic cross-sectional view showing a treatment apparatus which orally leads a first flexible endoscope into an organ, abdominally or transdermally leads a second flexible endoscope into the organ, abdominally or transdermally leads a treatment tool from another abdominal wall, and gives a medical treatment to a lesioned part according to a 20th embodiment.
FIG. 27B is a schematic view showing that the first flexible endoscope can be grasped by a rigid grasping forceps and a curved portion can be led in a desired direction.

As shown in FIG. 27A, in a treatment apparatus according to this embodiment, the first and second flexible endoscopes 11 and 22 are inserted into the stomach 2. A needle-shaped scalpel 30 is caused to protrude from the insertion portion 11a of the first endoscope 11, and it can be operated.

Additionally, a rigid grasping forceps 102 is inserted into the second gastric fistula formation tube 4'. An opening/closing operation portion 102a and a swiveling operation portion 102b are provided to this rigid grasping forceps 102 and, as shown in FIG. 27B, this rigid grasping forceps 102 is formed in such a manner that the end thereof can be operated to be opened/closed and to swivel.

When the lesioned part 28 exists on the gastric mucosa in the stomach 2 on the back side, the same medical treatment as that described in connection with the eighth embodiment is given to the lesioned part 28 by these two flexible endoscopes 11 and 22.

Therefore, the following can be said with respect to this embodiment. By leading the first endoscope 11 toward the lesioned part 28 by using the rigid grasping forceps 102, an operator of the second endoscope 22 can readily issue an instruction to an operator of the first endoscope 11.

A 21st embodiment will now be described with reference to FIGS. 28A to 28C. This embodiment is a modification of the 16th embodiment, and like reference numerals denote like or corresponding parts, thereby omitting the detailed explanation.

As shown in FIG. 28A, in a medical treatment apparatus according to this embodiment, the first and second flexible endoscopes 11 and 22 are inserted into the stomach 2. A clip with a thread 152 is arranged to this second flexible endoscope 22. A thread of this clip 152 has at least a length such that it is drawn to the outside of the body through the inner hole of the second gastric fistula formation tube 4'. As a treatment tool (insertion member), for example a collection treatment tool 154 whose end is formed into a hook-like shape is provided to the second gastric fistula formation tube 4'.

Further, a seal member 156 consisting of an elastic member such as silicon is attached to the upper end of the tube 8 of each of the two gastric fistula formation tubes 4 and 4'. These seal members 156 are appressed against the insertion portion 22a of the second endoscope 22 and the insertion portion of the collection treatment tool 154 and formed in such a manner that air in the stomach 2 hardly leaks to the outside of the body. A hole or slit having, e.g., a circular shape, a plus symbol shape, a minus symbol shape and the like is formed at the central part of each of these seal members 156.

When the lesioned part 28 exists on the gastric mucosa in the stomach 2 on the back side, a medical treatment is given to this lesioned part 28 by these two flexible endoscopes 11 and 22 and the collection treatment tool 154 as follows.

At first, for example, air is supplied into the stomach 2 through the first gastric fistula formation tube 4, and the stomach 4 is inflated. The first flexible endoscope 11 is orally inserted into the stomach 2. For example, a needle-shaped scalpel 30 is arranged in one channel of the insertion portion 11a of the endoscope 11. Then, as shown in FIG. 28A, the second flexible endoscope 22 is inserted into the stomach 2 through the inner hole of the first gastric fistula formation tube 4. A clip with a thread 152 is inserted into one channel of the insertion portion 22a of the endoscope 22 and caused to grasp the vicinity of the lesioned part 28. The collection treatment tool 154 is inserted into the stomach 2 through the inner hole of the second gastric fistula formation tube 4'. A thread portion of the clip with a thread 152 is hooked by the collection treatment tool 154 and, as shown in FIG. 28B, it is pulled out toward the outside of the second gastric fistula formation tube 4' (outside of the body).

With the tread portion of the clip with a thread 152 being held outside the body, the grasping forceps 24 is taken out from the second endoscope 22 to grasp the vicinity of the lesioned part 28 and it is pulled to upraise the lesioned part 28. The upraised lesioned part 28 is cut by using the needle-shaped scalpel 30. Upon completion of such a treatment, as shown in FIG. 28C, the clip with a thread 152 is removed from the living body while grasping the cut portion with the clip with a thread 152, the lesioned part 28 is collected, and examination is carried out.

On the other hand, the first and second flexible endoscopes 22 search for another lesioned part (not shown) and perform a similar treatment. For example, the collection treatment tool 154 is inserted from the second gastric fistula formation tube 4', the clip with a thread 152 is inserted into the second endoscope 22, the treatment like one mentioned above is carried out.

Incidentally, in the case of collectively cutting the large lesioned part 28, this lesioned part 28 is lifted up and upraised by using a plurality of the clips with a thread 152.

Therefore, the following can be said with respect to this embodiment. If a plurality of the lesioned parts 28 exist in the stomach 2, there is provided a treatment apparatus which obviates insertion/removal of endoscopes 11 and 22 when collecting the lesioned parts 28. That is, even if the cut piece (lesioned part 28) is large, the endoscopes 11 and 22 do not have to be removed to the outside of the body. Therefore, the treatment can be continuously carried out, thereby shortening the time required for the technique.

Although it is preferable to give a medical treatment with the stomach 2 being inflated by air supply, the supplied air does not leak to the outside of the body, due to the seal member 156.

A 22nd embodiment will now be described with reference to FIGS. 29 and 30. This embodiment is a modification of the first embodiment, and like reference numerals denote like or corresponding parts, thereby omitting the detailed explanation.

Figure 29:
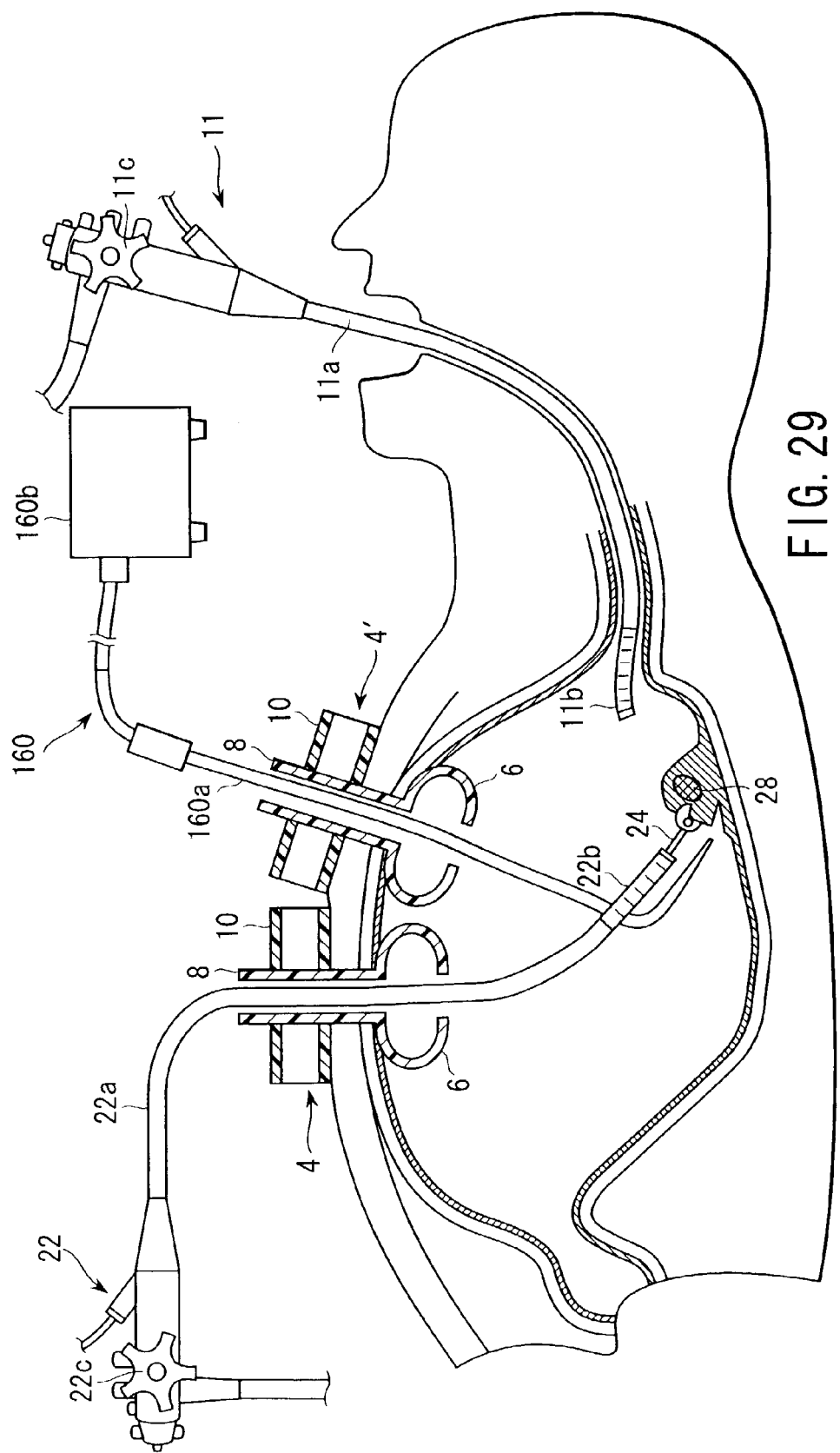
FIG. 29 is a schematic cross-sectional view showing a treatment apparatus which orally leads a first flexible endoscope into an organ, abdominally or transdermally leads a second flexible endoscope into the organ, abdominally or transdermally leads an ultrasonic treatment tool into the organ from another abdominal wall, a and gives a medical treatment to a lesioned part by using these two flexible endoscopes and one ultrasonic treatment tool according to a 22nd embodiment.

As shown in FIG. 29, in a treatment apparatus according to this embodiment, the first and second flexible endoscopes 11 and 22 are inserted into the stomach 2. In the second gastric fistula formation tube 4' is provided an ultrasonic treatment tool such as an ultrasonic coagulotomy device 160, an ultrasonic suction device or a cutting suture as a treatment tool (insertion member). The ultrasonic coagulotomy device 160 will be taken as an example and described next.

This ultrasonic coagulotomy device 160 has a treatment device 160a which can be inserted into a body cavity, and a base end portion, and a treatment control device 160b is provided outside the body. This device 160b controls on/off of device 160a. Further, the end portion of the treatment device 160a is formed to be bent at a desired angle.

If the lesioned part 28 exists on the gastric mucosa in the stomach 2 on the back side, this lesioned part 28 is treated by these two flexible endoscopes 11 and 22 and the ultrasonic coagulotomy device 160 as follows.

At first, for example, air is supplied into the stomach 2 of the first gastric fistula formation tube 4, and the stomach 2 is inflated. The first flexible endoscope 11 is orally inserted into the stomach 2. This first endoscope 11 is used for observing the lesioned part 28. The second flexible endoscope 22 is inserted into the stomach 2 through the inner hole of the first gastric fistula formation tube 4. The grasping forceps 24 is inserted into one channel of the insertion portion 22a of this endoscope 22, and a part in the vicinity of the lesioned part 28 is grasped and upraised.

The treatment device 160a of the ultrasonic coagulotomy device 160 is inserted through the inner hole of the second gastric fistula formation tube 4'. Since the end of this treatment device 160a is bent, it can be easily inserted under the upraised lesioned part 28. In this state, the treatment control device 160b is driven and operated, and the lesioned part 28 is cut.

Therefore, the following can be said with respect to this embodiment. The end portion of the treatment device 160a is bent, and the upraised lesioned part 28 can be readily cut.

Figure 30:
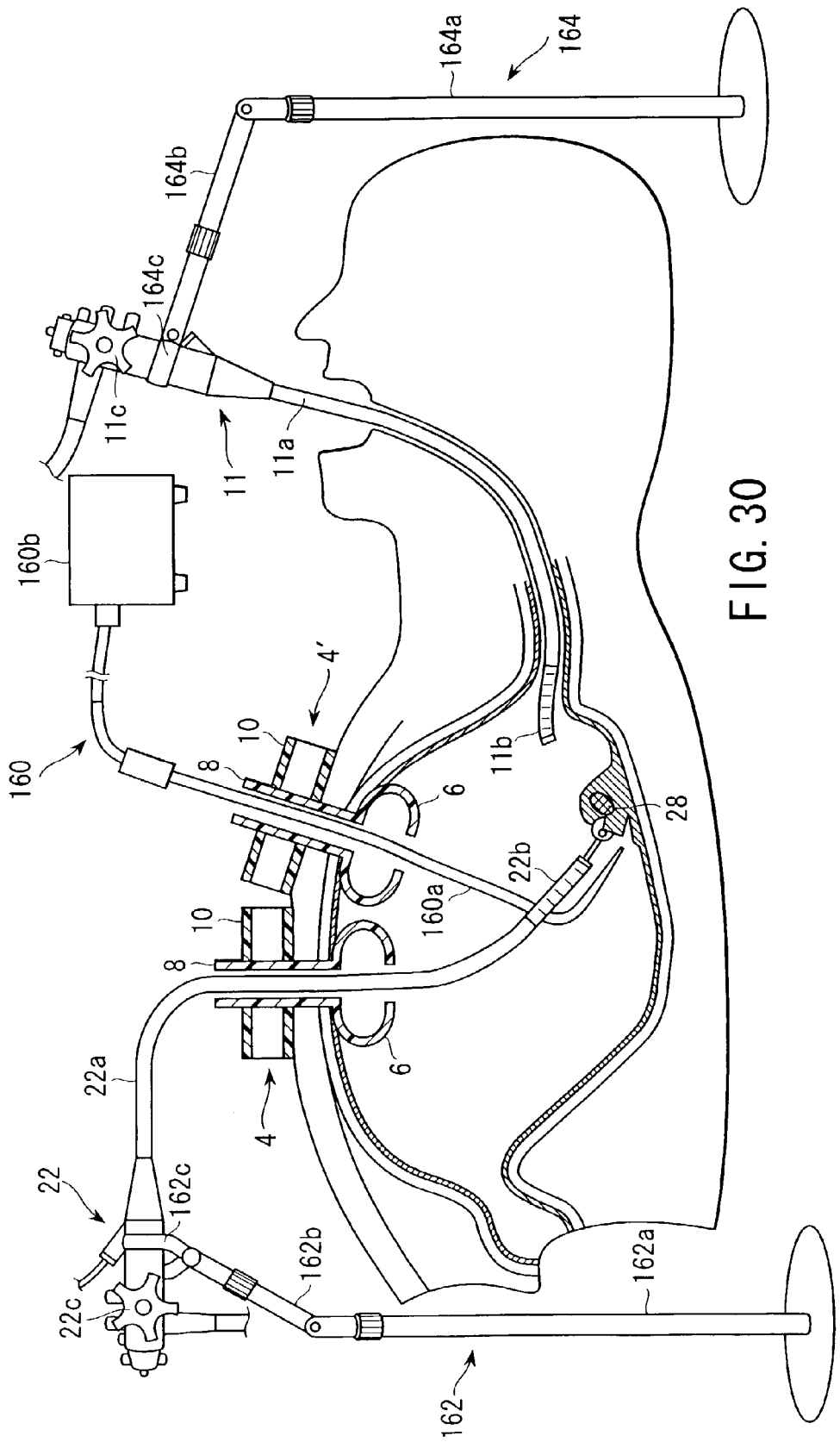
FIG. 30 is a schematic cross-sectional view showing a modification of a treatment apparatus according to the 22nd embodiment.

It is to be noted that stands 162 and 164 for an endoscope are provided to the first and second flexible endoscopes 11 and 22 according to this embodiment, as shown in FIG. 30. Leg portions 162a and 164a are provided to these stands 162a and 164a. Base end portions of bent arms 162b and 164b are pivoted on the leg portions 162a and 164a so as to be capable of swiveling. Endoscope main body holding portions 162c and 164c are attached at the end portions of the bent arms 162b and 164b. The first endoscope 11 is held by the endoscope main body holding portions 162c and 164c at a desired position where the lesioned part 28 can be observed. The second endoscope 22 is held by the endoscope main body holding portions 162c and 164c with the lesioned part 28 being grasped.

Therefore, since the first and second endoscopes 11 and 22 are held at desired positions, the operations needed by an operator can be reduced. By holding the two endoscopes 11 and 22 at desired positions in this manner, for example, the treatment device 160a of the ultrasonic coagulotomy device 160 can be inserted from the second gastric fistula formation tube 4', and one person can give a medical treatment to the lesioned part 28.

Moreover, such stands 162 and 164 may be provided for the ultrasonic coagulotomy device 160 or the like.

A 23rd embodiment will now be described with reference to FIG. 31. This embodiment is a modification of the 22nd embodiment, and like reference numerals denote like or corresponding parts, thereby omitting the detailed explanation.

Figure 31:
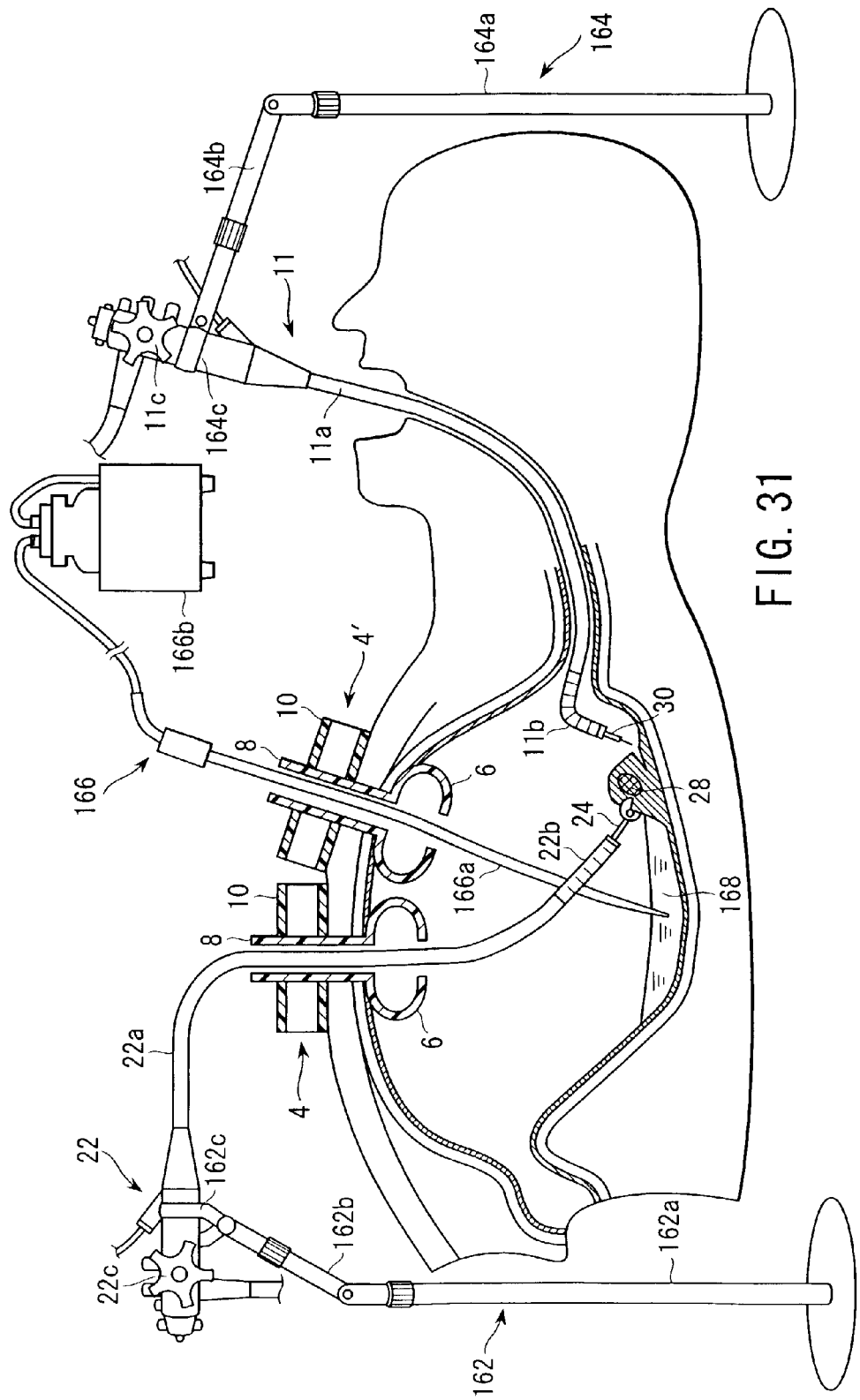
FIG. 31 is a schematic cross-sectional view showing a treatment apparatus which orally leads a first flexible endoscope into an organ, abdominally or transdermally leads a second flexible endoscope into the organ, abdominally or transdermally leads a suction device into the organ from another abdominal cavity, and gives a medical treatment to a lesioned part by using these two flexible endoscopes and one suction device according to a 23rd embodiment.

As shown in FIG. 31, in a treatment apparatus according to this embodiment, the first and second flexible endoscopes 11 and 22 are inserted into the stomach 2. For example, a suction device 166 as a treatment tool (insertion member) is provided to the second gastric fistula formation tube 4'. This suction device 166 includes a drain tube 166a which can be inserted into the stomach 2 through the second gastric fistula formation tube 4'. An end portion of an aspirator 166b is provided at a base end portion of this drain tube 166a. Therefore, a stored liquid 168 such as sordes in the stomach can be sucked and discharged to the outside of the body by driving and operating the aspirator 166b.

When the lesioned part 28 exists on the gastric mucosa in the stomach 2 on the back side, the lesioned part 28 is treated by these two flexible endoscopes 11 and 22 and the suction device 166 as follows.

At first, for example, air is supplied into the stomach 2 through the first gastric fistula formation tube 4, and the stomach 2 is inflated. The first flexible endoscope 11 is orally inserted into the stomach 2. For example, a needle-shaped scalpel 30 is arranged in one channel of the insertion portion 11a of the endoscope 11.

Then, as shown in FIG. 31, the second flexible endoscope 22 is inserted into the stomach 2 through the inner hole of the first gastric fistula formation tube 4. The grasping forceps 24 is inserted into one channel of the insertion portion 22a of this endoscope 22, a part in the vicinity of the lesioned part 28 is grasped. Subsequently, the drain tube 166a of the suction device 166 is inserted through the inner hole of the second gastric fistula formation tube 4'. This drain tube 166a is put into the stored liquid, such as sordes retained in the vicinity of the lesioned part 28 on the back side, the aspirator 166b is driven and operated, and the accumulated liquid is discharged to the outside of the body.

Thereafter, the lesioned part 28 grasped and upraised by the grasping forceps 24 of the second endoscope 22 is cut by using the needle-shaped scalpel 30 of the first endoscope 11. Upon completion of such a treatment, the second endoscope 22 is removed from the living body while grasping the cut part by the grasping forceps 24, the lesioned part 28 is collected, and examination is carried out.

Therefore, the following can be said with respect to this embodiment. Since the lesioned part 28 can be operated after removing the sordes or the like retained in an organ, the lesioned part 28 can be readily confirmed by using the first and second endoscopes 11 and 22, and the possibility of leaving the lesioned part 28 behind can be suppressed.

Incidentally, although description has been given as to the case where the drain tube 166a is inserted through the second gastric fistula formation tube 4' in this embodiment, the drain tube 166a may be inserted from the first gastric fistula formation tube 4 together with the second endoscope 22.

A 24th embodiment will now be described with reference to FIGS. 32A and 32B. This embodiment is a modification of the 22nd embodiment, and like reference numerals denote like or corresponding parts, thereby omitting the detailed explanation.

Figures 32A, 32B:
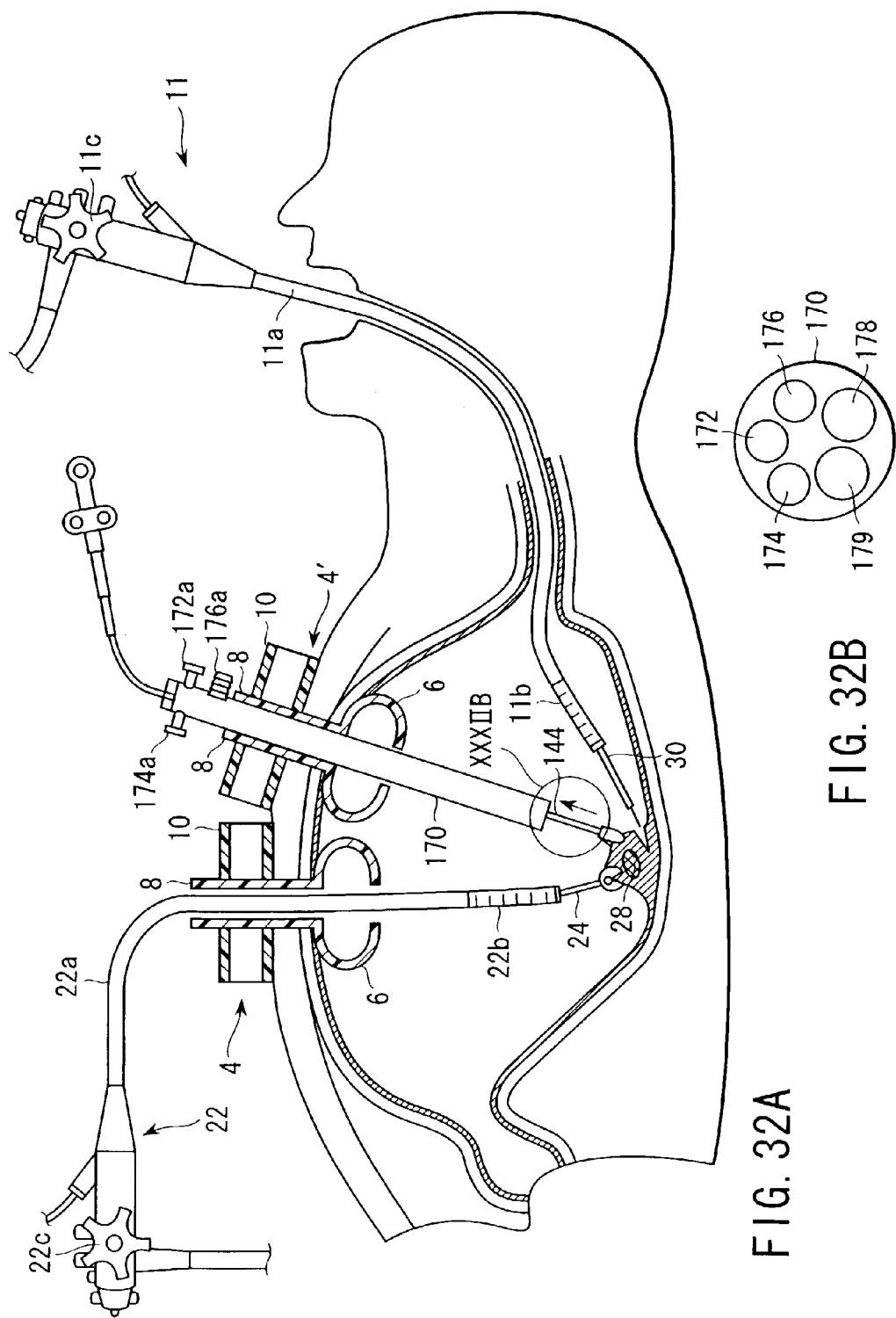
FIG. 32A is a schematic cross-sectional view showing a treatment apparatus which orally leads a first flexible endoscope into an organ, abdominally or transdermally leads a second flexible endoscope into the organ, abdominally or transdermally leads a multi-lumen treatment tube into the organ from another abdominal wall, and gives a medical treatment to a lesioned part by using these two flexible endoscopes and one multi-lumen treatment tube according to a 24th embodiment.
FIG. 32B is a schematic view showing the multi-lumen treatment tube illustrated in FIG. 32A, as seen from a direction indicated by an arrow B.

As shown in FIG. 32A, in a treatment apparatus according to this embodiment, the first and second flexible endoscopes 11 and 22 are inserted. In addition, a treatment tube 170 as a treatment tool (insertion member) having a plurality of lumens (five in this embodiment) is provided to the second gastric fistula formation tube 4'. These five lumens are formed as an air supply port 172, a water supply port 174, a suction port 176 and two forceps channels 178 and 179, respectively. The air supply port 172 includes a syringe air supply port 172a at the upper end portion of the treatment tube 170. Likewise, each of the water supply port 174 and the suction port 176 includes a syringe water supply port 174a and an aspirator duct 176a. The grasping forceps 144 is arranged in the forceps channel 178.

When the lesioned part 28 exists on the gastric mucosa in the stomach 2 on the back side, this lesioned part 28 can be treated by these two flexible endoscopes 11 and 22 and the grasping forceps 144 as follows.

At first, for example, air is supplied into the stomach 2 through the first gastric fistula formation tube 4, and the stomach 2 is inflated. The first flexible endoscope 11 is orally inserted into the stomach 2. For example, a needle-shaped scalpel 30 is arranged in one channel of the insertion portion 11a of this endoscope 11. As shown in FIG. 31, the second flexible endoscope 22 is inserted into the stomach 2 through the inner hole of the first gastric fistula formation tube 4. The grasping forceps 24 is inserted into one channel of the insertion portion 22a of the endoscope 22, and a part in the vicinity of the lesioned part 28 is grasped. The treatment tube 170 is inserted through the inner hole of the second gastric fistula formation tube 4'. For example, the grasping forceps 144 is arranged in the forceps channel 178 of the treatment tube 170.

Thereafter, the lesioned part 28 grasped and upraised by the grasping forcipes 24 and 144 is cut by the needle-shaped scalpel 30 of the first endoscope 11. Upon completion of such a treatment, the second endoscope 22 is removed from the living body while grasping the cut part by grasping forceps 24, the lesioned part 28 is collected, and examination is carried out. Air is supplied from the syringe air supply port 172a, and this air is injected to the cut part and the like from the air supply port 172. A liquid is supplied from the syringe water supply port 174a, and this liquid is injected to the cut part or the like from the water supply port 174. A cut piece obtained from the cut part is sucked from the suction port 176 via the aspirator duct 176a, and the lesioned part 28 and the vicinity thereof in the stomach 2 are cleansed.

Therefore, the following can be said with respect to this embodiment. Since the lesioned part 28 can be operated on after removing the sordes and the like retained in an organ, the lesioned part 28 can be readily confirmed by using the first and second endoscopes 11 and 22, and the possibility of leaving the lesioned part 28 behind can be suppressed.

It is to be noted that the seal member which seals the insertion portion 22a of the endoscope 22 is provided at the upper end portion of the tube 8 of each of the gastric fistula formation tubes 4 and 4' in the fourth, seventh to ninth, 12th, 13th, and 19th to 21st embodiments but the present invention is not restricted to these embodiments, and it is preferable that such a seal member is provided in any other embodiment. By providing such a seal member, the air in the stomach cannot easily leak to the outside, thus the stomach can be maintained in an expanded state.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A medical treatment method comprising:
    orally inserting a first endoscope having a first treatment tool provided thereto into a body cavity;
    inserting a first insertion member insertion support tool from at least one of abdominal and transdermal cavities into the body cavity;
    inserting a second endoscope having a second treatment tool provided thereto into the body cavity through the first insertion member insertion support tool;
    grasping a lesioned part by the second treatment tool inserted into the body cavity by the second endoscope;
    cutting the lesioned part by the first treatment tool inserted into the body cavity by the first endoscope; and
    removing the lesioned part.

2. The medical treatment method according to claim 1, wherein the second endoscope is inserted into the body cavity while supplying air into the body cavity from between the first insertion member insertion support tool and the second endoscope.

3. The medical treatment method according to claim 2, further comprising:
    detecting sliding of the second endoscope with respect to the first insertion member insertion support tool; and
    controlling air supply and stop of air supply into the body cavity in accordance with the detected sliding of the second endoscope.

4. The medical treatment method according to claim 1, further comprising supplying air into the body cavity through the first insertion member insertion support tool.

5. The medical treatment method according to claim 1, further comprising:

inserting a third treatment tool into the body cavity through the first insertion member insertion support tool; and
grasping the lesioned part by the third treatment tool.

6. The medical treatment method according to claim 5, further comprising leading the first endoscope toward the lesioned part by the third treatment tool.

7. The medical treatment method according to claim 4, further comprising leading an end portion of the second endoscope toward the lesioned part by the first endoscope.

8. The medical treatment method according to claim 7, wherein the operation to lead the end portion of the second endoscope toward the lesioned part further includes an operation to grasp a grasping portion provided at the end portion of the second endoscope by the first treatment tool.

9. The medical treatment method according to claim 1, further comprising:
inserting a second insertion member insertion support tool from at least one of abdominal and transdermal cavities into the body cavity;
inserting a third treatment tool into the body cavity through the second insertion member insertion support tool; and
grasping the lesioned part by the third treatment tool.

10. The medical treatment method according to claim 9, wherein the third treatment tool is inserted into the body cavity through a treatment tube having a plurality of lumens provided in an inner hole of the second insertion member insertion support tool.

11. The medical treatment method according to claim 1, further comprising:
inserting a second insertion member insertion support tool from at least one of abdominal and transdermal cavities into the body cavity;
inserting a third endoscope having a third treatment tool provided thereto into the body cavity by the second insertion member insertion support tool; and
grasping the lesioned part by the third treatment tool.

12. The medical treatment method according to claim 1, further comprising discharging accumulated matter in the body cavity to the outside of the body.

13. The medical treatment method according to claim 12, wherein an aspirator, which discharges the accumulated matter to the outside of the body, is inserted from at least one of abdominal and transdermal cavities into the body cavity by the inserted second insertion member insertion support tool.

14. A medical treatment method comprising:
orally inserting a first endoscope having a first treatment tool provided thereto into a body cavity;
inserting an insertion member insertion support tool from at least one of abdominal and transdermal cavities into the body cavity;
inserting a tubular member into the body cavity through an inner hole of the insertion member insertion support tool;
inserting a second treatment tool having a polyarticular arm and a second endoscope into the body cavity through an inner hole of the tubular member;
grasping a lesioned part by the second treatment tool inserted into the body cavity by the tubular member;
cutting the lesioned part by the first treatment tool inserted into the body cavity by the first endoscope; and
removing the lesioned part.

15. A medical treatment method comprising:
orally inserting a first endoscope into a body cavity;
inserting an insertion member insertion support tool from at least one of abdominal and transdermal cavities into the body cavity;
inserting a cover tube into the body cavity through an inner hole of the insertion member insertion support tool;
inserting a treatment tool and a second endoscope into the body cavity through an inner hole of the cover tube;
bringing an end portion of the cover tube into contact with the circumference of a lesioned part;
sucking the lesioned part by a suction apparatus connected to the cover tube;
cutting a lesioned part by the treatment tool; and
removing the lesioned part.

16. A medical treatment method comprising:
orally inserting a first endoscope having a first treatment tool provided thereto into a body cavity;
inserting from at least one of abdominal and transdermal cavities into the body cavity an insertion member insertion support tool having a leading portion which leads to a lesioned part;
providing a second treatment tool and inserting into the body cavity a second endoscope which is led to an abdominal side where the lesioned part exists by the insertion member insertion support tool;
grasping the lesioned part by the second treatment tool inserted into the body cavity by the second endoscope;
cutting the lesioned part by the first treatment tool inserted into the body cavity by the first endoscope; and
removing the lesioned part.

17. A medical treatment method comprising:
orally inserting a first endoscope having a first treatment tool provided thereto into a body cavity;
inserting a first insertion member insertion support tool from at least one of abdominal and transdermal cavities into the body cavity;
inserting a second insertion member insertion support tool from at least one of abdominal and transdermal cavities into the body cavity;
inserting a second endoscope having a second treatment tool provided thereto into the body cavity by the first insertion member insertion support tool;
grasping a lesioned part by the second treatment tool inserted into the body cavity by the second endoscope;
leading to the lesioned part a third treatment tool inserted into the body cavity by the second insertion member insertion support tool by the first treatment tool inserted into the body cavity by the first endoscope;
grasping the lesioned part by the third treatment tool;
cutting the lesioned part by a fourth treatment tool inserted into the body cavity by the first endoscope; and
removing the lesioned part.

18. The medical treatment method according to claim 17, wherein the third treatment tool is fixed to the second insertion portion insertion support tool after grasping the lesioned part by the third treatment tool.

19. The medical treatment method according to claim 17, wherein the first endoscope has a plurality of treatment tool channels.

20. A medical treatment method for a lesioned part existing in an organ of a living body, comprising:
orally inserting an insertion portion of a first flexible endoscope which is inserted into an organ;

inserting an insertion portion of a second flexible endoscope which is inserted from at least one of abdominal and transdermal cavities into the organ; and giving a medical treatment to a lesioned part in the organ in cooperation with the first and second flexible endoscopes.

21. The medical treatment method according to claim 20, wherein an insertion portion of a third flexible endoscope is inserted from at least one of abdominal and transdermal cavities into the organ.

22. The medical treatment method according to claim 20, wherein a medical treatment is given to the inside of the organ by endoscopic mucosal resection (EMR).

23. The medical treatment method according to claim 21, wherein a medical treatment is given to the inside of the organ by endoscopic mucosal resection.

24. The medical treatment method according to claim 20, wherein the lesioned part is lifted up by the second flexible endoscope and the lesioned part is cut by the first flexible endoscope.

25. The medical treatment method according to claim 21, wherein the lesioned part is lifted up by the second and third flexible endoscopes, and the lesioned part is cut by the first flexible endoscope.

26. The medical treatment method according to claim 20, wherein the second flexible endoscope, an observation optical system of which has been eliminated from an insertion portion thereof, is led to a desired position by the first flexible endoscope.

27. The medical treatment method according to claim 20, wherein the organ is a stomach.

28. The medical treatment method according to claim 27, wherein the second flexible endoscope is inserted through a first insertion member insertion support tool which connects the stomach and the outside of the body.

29. The medical treatment method according to claim 28, wherein the first insertion member insertion support tool is formed by percutaneous endoscopic gastrostomy (PEG).

30. The medical treatment method according to claim 29, wherein a catheter is set in an inner hole of the first insertion member insertion support tool and the second flexible endoscope is inserted through this catheter.

31. The medical treatment method according to claim 29, wherein a treatment tool is inserted through a second insertion member insertion support tool provided at a position different from that of the first insertion member insertion support tool.

32. The medical treatment method according to claim 20, wherein the first flexible endoscope orally inserted into the organ is used to observe the lesioned part, and a medical treatment is given by a plurality of flexible endoscopes which are inserted from at least one of abdominal and transdermal cavities.

33. The medical treatment method according to claim 21, wherein the first flexible endoscope orally inserted into the organ is used to observe the lesioned part, and a medical treatment is given by a plurality of flexible endoscopes which are inserted from at least one of abdominal and transdermal cavities.

* * * * *